(12) United States Patent
Callewaert et al.

(10) Patent No.: US 11,098,337 B2
(45) Date of Patent: *Aug. 24, 2021

(54) CELLS PRODUCING GLYCOPROTEINS HAVING ALTERED GLYCOSYLATION PATTERNS AND METHOD AND USE THEREOF

(71) Applicants: VIB VZW, Ghent (BE); UNIVERSITEIT GENT, Ghent (BE)

(72) Inventors: Nico L. M. Callewaert, Nevele (BE); Karen De Pourcq, Ghent (BE); Steven Geysens, Wannegem-Lede (BE); Leander Meuris, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 571 days.

This patent is subject to a terminal disclaimer.

(21) Appl. No.: 14/322,827

(22) Filed: Jul. 2, 2014

(65) Prior Publication Data

US 2014/0345004 A1 Nov. 20, 2014

Related U.S. Application Data

(63) Continuation of application No. 12/737,719, filed as application No. PCT/EP2009/060348 on Aug. 10, 2009, now Pat. No. 8,815,580.

(30) Foreign Application Priority Data

Aug. 8, 2008 (EP) ..................................... 08162059
Aug. 8, 2008 (EP) ..................................... 08162063

(51) Int. Cl.
*C12N 5/00* (2006.01)
*C12N 9/24* (2006.01)
*C12P 21/00* (2006.01)
*A61K 38/00* (2006.01)

(52) U.S. Cl.
CPC .......... *C12P 21/005* (2013.01); *C12N 9/2402* (2013.01); *C12Y 302/01096* (2013.01); *C12Y 302/01113* (2013.01); *C07K 2319/02* (2013.01)

(58) Field of Classification Search
CPC ........................... C12N 9/24; C12Y 302/01096
See application file for complete search history.

(56) References Cited

U.S. PATENT DOCUMENTS

| | | | | | |
|---|---|---|---|---|---|
| 5,260,223 | A | * | 11/1993 | Brenner | C07K 14/7051 435/7.1 |
| 2003/0130317 | A1 | * | 7/2003 | Butters | A61K 31/00 514/328 |
| 2006/0030521 | A1 | * | 2/2006 | DeFrees | C07K 1/006 514/20.9 |
| 2008/0220473 | A1 | * | 9/2008 | Claeyssens | C12N 9/2402 435/69.1 |
| 2010/0113517 | A1 | * | 5/2010 | Palling | A61K 38/47 514/315 |
| 2011/0191913 | A1 | * | 8/2011 | Callewaert | C12Y 302/01096 800/298 |

OTHER PUBLICATIONS

Zhu et al. (1997) beta 1,4 N-Acetylgalactosaminyltransferase (GM2/GD2/GA2 synthase) forms homodimers in the endoplasmic reticulum: a strategy to test for dimerization of Golgi membrane proteins,Glycobiol., vol. 7, pp. 987-996.*
Crispin et al. (2006) Inhibition of hybrid- and complex-type glycosylation reveals the presence of the GlcNAc transferase I-independent fucosylation pathway, Glycobiol., vol. 16, pp. 748-756.*
Rao et al. (1995) Crystal structure of endo-1-N-acetylglucosaminidase H at 1.9 Å resolution: active-site geometry and substrate recognition, Structure, vol. 3, pp. 449-457.*
Uchiyama et al. (2003) Uptake of N,N_-Diacetylchitobiose [(GlcNAc)2] via the Phosphotransferase System is Essential for Chitinase Production by Serratia marcescens 2170, J. Bacteriol., vol. 185, pp. 1776-1782.*
Bickel et al., Biosynthesis of Lipid-linked Oligosaccharides in *Saccharomyces cerevisiae*, Journal of Biological Chemistry, Oct. 14, 2005, pp. 34500-34506, vol. 280, No. 41.
Product Information from Sigma-Aldrich for Endoglycosidase H, from *Streptococcus plicatus* Recombinant, expressed in. *E. coli*, copyrighted 2014, available at www.sigmaaldrich.com.

* cited by examiner

*Primary Examiner* — Manjunath N Rao
*Assistant Examiner* — Samuel W Liu
(74) *Attorney, Agent, or Firm* — Patent Law Works, LLP

(57) ABSTRACT

The disclosure relates to the field of glyco-engineering, more specifically, to eukaryotic cells wherein both an endoglucosaminidase and a glycoprotein are present. These cells can be used to deglycosylate or partly deglycosylate the (exogenous) glycoprotein, in particular, without the need for adding an extra enzyme. Methods are also provided for the application of these cells in protein production. According to one specific aspect, the eukaryotic cells are glyco-engineered yeast cells in which, additionally, at least one exogenous enzyme needed for complex glycosylation is present, e.g., allowing easier separation of differentially glycosylated glycoproteins.

11 Claims, 11 Drawing Sheets

Specification includes a Sequence Listing.

SEQUENCE LISTING

```
<160> NUMBER OF SEQ ID NOS: 33

<210> SEQ ID NO 1
<211> LENGTH: 4
<212> TYPE: PRT
<213> ORGANISM: Artificial Sequence
<220> FEATURE:
<223> OTHER INFORMATION: Consensus sequence

<400> SEQUENCE: 1

Lys Asp Glu Leu
1

<210> SEQ ID NO 2
<211> LENGTH: 4
<212> TYPE: PRT
<213> ORGANISM: Artificial Sequence
<220> FEATURE:
<223> OTHER INFORMATION: Consensus sequence

<400> SEQUENCE: 2

His Asp Glu Leu
1

<210> SEQ ID NO 3
<211> LENGTH: 24
<212> TYPE: DNA
<213> ORGANISM: Artificial Sequence
<220> FEATURE:
<223> OTHER INFORMATION: Synthetic gene

<400> SEQUENCE: 3
ctcgagaaaa gagaggctga agcg                                        24

<210> SEQ ID NO 4
<211> LENGTH: 8
<212> TYPE: PRT
<213> ORGANISM: Artificial Sequence
<220> FEATURE:
<223> OTHER INFORMATION: Kex2p cleavage site

<400> SEQUENCE: 4

Leu Val Lys Arg Glu Ala Glu Ala
1               5

<210> SEQ ID NO 5
<211> LENGTH: 18
<212> TYPE: DNA
<213> ORGANISM: Artificial Sequence
<220> FEATURE:
<223> OTHER INFORMATION: Synthetic gene

<400> SEQUENCE: 5
taaccctaag gtaagctt                                               18

<210> SEQ ID NO 6
<211> LENGTH: 19
```

<212> TYPE: DNA
<213> ORGANISM: Artificial Sequence
<220> FEATURE:
<223> OTHER INFORMATION: Adaptor sequence

<400> SEQUENCE: 6
gccgagccga cggacctgc                                                    19

<210> SEQ ID NO 7
<211> LENGTH: 23
<212> TYPE: DNA
<213> ORGANISM: Artificial Sequence
<220> FEATURE:
<223> OTHER INFORMATION: Adaptor sequence

<400> SEQUENCE: 7
ctaggcaggt ccgtcggctc ggc                                               23

<210> SEQ ID NO 8
<211> LENGTH: 6
<212> TYPE: PRT
<213> ORGANISM: Artificial Sequence
<220> FEATURE:
<223> OTHER INFORMATION: Linker sequence

<400> SEQUENCE: 8

Lys Arg Glu Ala Glu Ala
1               5

<210> SEQ ID NO 9
<211> LENGTH: 18
<212> TYPE: DNA
<213> ORGANISM: Artificial Sequence
<220> FEATURE:
<223> OTHER INFORMATION: linker sequence

<400> SEQUENCE: 9
aagagagagg ctgaggcc                                                     18

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
ggaattcatg tctgcttcaa ctcattcg                                          28

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
cggggtaccg gtattagaat aacaagtaga ac                                     32

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12

-continued

```
cggggtaccg taaattctac tccttcatat agg                                33
```

<210> SEQ ID NO 13
<211> LENGTH: 6
<212> TYPE: PRT
<213> ORGANISM: Artificial Sequence
<220> FEATURE:
<223> OTHER INFORMATION: Kex2 cleavage recognition site

<400> SEQUENCE: 13

Lys Arg Glu Ala Glu Ala
1               5

<210> SEQ ID NO 14
<211> LENGTH: 1339
<212> TYPE: DNA
<213> ORGANISM: Artificial Sequence
<220> FEATURE:
<223> OTHER INFORMATION: Fusion protein
<220> FEATURE:
<221> NAME/KEY: CDS
<222> LOCATION: (7)..(1338)

<400> SEQUENCE: 14

```
ctcgag atg att cac acc aac ctg aag aaa aag ttc agc tgc tgc gtc        48
       Met Ile His Thr Asn Leu Lys Lys Lys Phe Ser Cys Cys Val
       1               5                   10 ctg gtc ttt ctt ctg ttt gca gtc atc tgt gtg tgg aag gaa aag aag       96
Leu Val Phe Leu Leu Phe Ala Val Ile Cys Val Trp Lys Glu Lys Lys
15                  20                  25                  30 aaa ggg agt tac tat gat tcc ttt aaa ttg caa acc aag gaa ttc cag      144
Lys Gly Ser Tyr Tyr Asp Ser Phe Lys Leu Gln Thr Lys Glu Phe Gln
                35                  40                  45 gtg tta aag agt ctg ggg aaa ttg gcc atg ggg tct gat tcc cag tct      192
Val Leu Lys Ser Leu Gly Lys Leu Ala Met Gly Ser Asp Ser Gln Ser
        50                  55                  60 gta tcc tca agc agc acc cag gac ccc cac agg ggc cgc cag acc ctc      240
Val Ser Ser Ser Ser Thr Gln Asp Pro His Arg Gly Arg Gln Thr Leu
65                  70                  75 ggc agt ctc aga ggc cta gcc aag gcc aaa cca gag gcc tcc ttc cag      288
Gly Ser Leu Arg Gly Leu Ala Lys Ala Lys Pro Glu Ala Ser Phe Gln
            80                  85                  90 gtg tgg aac aag gac gta ccc gtt aaa gaa ctg cag ttg aga gct gaa      336
Val Trp Asn Lys Asp Val Pro Val Lys Glu Leu Gln Leu Arg Ala Glu
95                  100                 105                 110 cca act gat ttg cct agg ctt atc gtt tac ttc cag act act cac gac      384
Pro Thr Asp Leu Pro Arg Leu Ile Val Tyr Phe Gln Thr Thr His Asp
                115                 120                 125 tct tcc aac aga cca atc tcc atg ttg cca ttg atc act gag aag ggt      432
Ser Ser Asn Arg Pro Ile Ser Met Leu Pro Leu Ile Thr Glu Lys Gly
            130                 135                 140 atc gct ttg act cac ttg atc gtt tgt tcc ttc cac att aac cag ggt      480
Ile Ala Leu Thr His Leu Ile Val Cys Ser Phe His Ile Asn Gln Gly
        145                 150                 155 ggt gtt gtt cac ttg aac gac ttc cca cca gat gat cca cac ttc tac      528
Gly Val Val His Leu Asn Asp Phe Pro Pro Asp Asp Pro His Phe Tyr
    160                 165                 170 act ttg tgg aac gag act atc act atg aag cag gct ggt gtt aag gtt      576
Thr Leu Trp Asn Glu Thr Ile Thr Met Lys Gln Ala Gly Val Lys Val
175                 180                 185                 190 atg gga atg gtt ggt ggt gct gct cct ggt tct ttc aac act cag act      624
Met Gly Met Val Gly Gly Ala Ala Pro Gly Ser Phe Asn Thr Gln Thr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 195 |     |     |     |     | 200 |     |     |     |     | 205 |     |     |      |
| ttg | gac | tct | cca | gac | tct | gct | act | ttc | gag | cac | tac | tac | ggt | caa | ttg | 672  |
| Leu | Asp | Ser | Pro | Asp | Ser | Ala | Thr | Phe | Glu | His | Tyr | Tyr | Gly | Gln | Leu |      |
|     |     | 210 |     |     |     |     | 215 |     |     |     |     | 220 |     |     |     |      |
| aga | gat | gct | atc | gtt | aac | ttc | cag | ttg | gag | gga | atg | gat | ttg | gac | gtt | 720  |
| Arg | Asp | Ala | Ile | Val | Asn | Phe | Gln | Leu | Glu | Gly | Met | Asp | Leu | Asp | Val |      |
|     |     | 225 |     |     |     |     | 230 |     |     |     |     | 235 |     |     |     |      |
| gag | caa | cca | atg | tcc | caa | caa | ggt | atc | gac | aga | ttg | atc | gct | aga | ttg | 768  |
| Glu | Gln | Pro | Met | Ser | Gln | Gln | Gly | Ile | Asp | Arg | Leu | Ile | Ala | Arg | Leu |      |
|     | 240 |     |     |     |     | 245 |     |     |     |     | 250 |     |     |     |     |      |
| aga | gct | gat | ttc | ggt | cca | gac | ttc | ttg | att | act | ttg | gct | cca | gtt | gct | 816  |
| Arg | Ala | Asp | Phe | Gly | Pro | Asp | Phe | Leu | Ile | Thr | Leu | Ala | Pro | Val | Ala |      |
| 255 |     |     |     |     | 260 |     |     |     |     | 265 |     |     |     |     | 270 |      |
| tct | gct | ttg | gag | gac | tcc | tct | aac | ttg | tct | ggt | ttc | tcc | tac | act | gct | 864  |
| Ser | Ala | Leu | Glu | Asp | Ser | Ser | Asn | Leu | Ser | Gly | Phe | Ser | Tyr | Thr | Ala |      |
|     |     |     |     | 275 |     |     |     |     | 280 |     |     |     |     | 285 |     |      |
| ttg | caa | cag | act | cag | ggt | aac | gac | att | gac | tgg | tac | aac | act | cag | ttc | 912  |
| Leu | Gln | Gln | Thr | Gln | Gly | Asn | Asp | Ile | Asp | Trp | Tyr | Asn | Thr | Gln | Phe |      |
|     |     |     | 290 |     |     |     |     | 295 |     |     |     |     | 300 |     |     |      |
| tac | tct | ggt | ttc | ggt | tct | atg | gct | gac | act | tcc | gac | tac | gac | aga | atc | 960  |
| Tyr | Ser | Gly | Phe | Gly | Ser | Met | Ala | Asp | Thr | Ser | Asp | Tyr | Asp | Arg | Ile |      |
|     |     | 305 |     |     |     |     | 310 |     |     |     |     | 315 |     |     |     |      |
| gtt | gct | aac | ggt | ttc | gct | cca | gct | aaa | gtt | gtt | gct | ggt | cag | ttg | act | 1008 |
| Val | Ala | Asn | Gly | Phe | Ala | Pro | Ala | Lys | Val | Val | Ala | Gly | Gln | Leu | Thr |      |
|     | 320 |     |     |     |     | 325 |     |     |     |     | 330 |     |     |     |     |      |
| act | cct | gaa | ggt | gct | gga | tgg | att | cca | act | tcc | tcc | ttg | aac | aac | act | 1056 |
| Thr | Pro | Glu | Gly | Ala | Gly | Trp | Ile | Pro | Thr | Ser | Ser | Leu | Asn | Asn | Thr |      |
| 335 |     |     |     |     | 340 |     |     |     |     | 345 |     |     |     |     | 350 |      |
| atc | gtt | tcc | ttg | gtt | tcc | gag | tac | ggt | caa | atc | ggt | ggt | gtt | atg | gga | 1104 |
| Ile | Val | Ser | Leu | Val | Ser | Glu | Tyr | Gly | Gln | Ile | Gly | Gly | Val | Met | Gly |      |
|     |     |     |     | 355 |     |     |     |     | 360 |     |     |     |     | 365 |     |      |
| tgg | gag | tac | ttc | aat | tcc | ttg | cca | ggt | ggt | act | gct | gaa | cca | tgg | gag | 1152 |
| Trp | Glu | Tyr | Phe | Asn | Ser | Leu | Pro | Gly | Gly | Thr | Ala | Glu | Pro | Trp | Glu |      |
|     |     |     | 370 |     |     |     |     | 375 |     |     |     |     | 380 |     |     |      |
| tgg | gct | caa | atc | gtt | act | gag | atc | ttg | aga | cca | gga | ttg | gtt | cca | gag | 1200 |
| Trp | Ala | Gln | Ile | Val | Thr | Glu | Ile | Leu | Arg | Pro | Gly | Leu | Val | Pro | Glu |      |
|     |     | 385 |     |     |     |     | 390 |     |     |     |     | 395 |     |     |     |      |
| ctc | aag | att | act | gag | gat | gac | gct | gct | aga | ttg | act | ggt | gct | tac | gaa | 1248 |
| Leu | Lys | Ile | Thr | Glu | Asp | Asp | Ala | Ala | Arg | Leu | Thr | Gly | Ala | Tyr | Glu |      |
|     | 400 |     |     |     |     | 405 |     |     |     |     | 410 |     |     |     |     |      |
| gaa | tcc | gtt | aag | gct | gct | gct | gct | gat | aac | aag | tcc | ttc | gtt | aag | agg | 1296 |
| Glu | Ser | Val | Lys | Ala | Ala | Ala | Ala | Asp | Asn | Lys | Ser | Phe | Val | Lys | Arg |      |
| 415 |     |     |     |     | 420 |     |     |     |     | 425 |     |     |     |     | 430 |      |
| cct | tcc | atc | aac | tac | tac | gct | atg | gtt | aac | gct | taa | cct | cag | g   |     | 1339 |
| Pro | Ser | Ile | Asn | Tyr | Tyr | Ala | Met | Val | Asn | Ala |     | Pro | Gln |     |     |      |
|     |     | 435 |     |     |     |     | 440 |     |     |     |     |     |     |     |     |      |

<210> SEQ ID NO 15
<211> LENGTH: 441
<212> TYPE: PRT
<213> ORGANISM: Artificial Sequence
<220> FEATURE:
<223> OTHER INFORMATION: Synthetic Construct

<400> SEQUENCE: 15

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu

```
            35                  40                  45
Lys Ser Leu Gly Lys Leu Ala Met Gly Ser Asp Ser Gln Ser Val Ser
 50                  55                  60

Ser Ser Ser Thr Gln Asp Pro His Arg Gly Arg Gln Thr Leu Gly Ser
 65                  70                  75                  80

Leu Arg Gly Leu Ala Lys Ala Lys Pro Glu Ala Ser Phe Gln Val Trp
                 85                  90                  95

Asn Lys Asp Val Pro Val Lys Glu Leu Gln Leu Arg Ala Glu Pro Thr
                100                 105                 110

Asp Leu Pro Arg Leu Ile Val Tyr Phe Gln Thr Thr His Asp Ser Ser
            115                 120                 125

Asn Arg Pro Ile Ser Met Leu Pro Leu Ile Thr Glu Lys Gly Ile Ala
        130                 135                 140

Leu Thr His Leu Ile Val Cys Ser Phe His Ile Asn Gln Gly Gly Val
145                 150                 155                 160

Val His Leu Asn Asp Phe Pro Pro Asp Asp Pro His Phe Tyr Thr Leu
                165                 170                 175

Trp Asn Glu Thr Ile Thr Met Lys Gln Ala Gly Val Lys Val Met Gly
                180                 185                 190

Met Val Gly Gly Ala Ala Pro Gly Ser Phe Asn Thr Gln Thr Leu Asp
            195                 200                 205

Ser Pro Asp Ser Ala Thr Phe Glu His Tyr Tyr Gly Gln Leu Arg Asp
        210                 215                 220

Ala Ile Val Asn Phe Gln Leu Glu Gly Met Asp Leu Asp Val Glu Gln
225                 230                 235                 240

Pro Met Ser Gln Gln Gly Ile Asp Arg Leu Ile Ala Arg Leu Arg Ala
                245                 250                 255

Asp Phe Gly Pro Asp Phe Leu Ile Thr Leu Ala Pro Val Ala Ser Ala
                260                 265                 270

Leu Glu Asp Ser Ser Asn Leu Ser Gly Phe Ser Tyr Thr Ala Leu Gln
            275                 280                 285

Gln Thr Gln Gly Asn Asp Ile Asp Trp Tyr Asn Thr Gln Phe Tyr Ser
        290                 295                 300

Gly Phe Gly Ser Met Ala Asp Thr Ser Asp Tyr Asp Arg Ile Val Ala
305                 310                 315                 320

Asn Gly Phe Ala Pro Ala Lys Val Val Ala Gly Gln Leu Thr Thr Pro
                325                 330                 335

Glu Gly Ala Gly Trp Ile Pro Thr Ser Ser Leu Asn Asn Thr Ile Val
            340                 345                 350

Ser Leu Val Ser Glu Tyr Gly Gln Ile Gly Gly Val Met Gly Trp Glu
        355                 360                 365

Tyr Phe Asn Ser Leu Pro Gly Gly Thr Ala Glu Pro Trp Glu Trp Ala
        370                 375                 380

Gln Ile Val Thr Glu Ile Leu Arg Pro Gly Leu Val Pro Glu Leu Lys
385                 390                 395                 400

Ile Thr Glu Asp Asp Ala Ala Arg Leu Thr Gly Ala Tyr Glu Glu Ser
                405                 410                 415

Val Lys Ala Ala Ala Asp Asn Lys Ser Phe Val Lys Arg Pro Ser
            420                 425                 430

Ile Asn Tyr Tyr Ala Met Val Asn Ala
        435                 440

<210> SEQ ID NO 16
```

<211> LENGTH: 1369
<212> TYPE: DNA
<213> ORGANISM: Artificial Sequence
<220> FEATURE:
<223> OTHER INFORMATION: Fusion protein
<220> FEATURE:
<221> NAME/KEY: CDS
<222> LOCATION: (7)..(1359)

<400> SEQUENCE: 16

```
ctcgag atg att cac acc aac ctg aag aaa aag ttc agc tgc tgc gtc          48
       Met Ile His Thr Asn Leu Lys Lys Lys Phe Ser Cys Cys Val
       1               5                   10 ctg gtc ttt ctt ctg ttt gca gtc atc tgt gtg tgg aag gaa aag aag          96
Leu Val Phe Leu Leu Phe Ala Val Ile Cys Val Trp Lys Glu Lys Lys
15                  20                  25                  30 aaa ggg agt tac tat gat tcc ttt aaa ttg caa acc aag gaa ttc cag         144
Lys Gly Ser Tyr Tyr Asp Ser Phe Lys Leu Gln Thr Lys Glu Phe Gln
                35                  40                  45 gtg tta aag agt ctg ggg aaa ttg gcc atg ggg tct gat tcc cag tct         192
Val Leu Lys Ser Leu Gly Lys Leu Ala Met Gly Ser Asp Ser Gln Ser
            50                  55                  60 gta tcc tca agc agc acc cag gac ccc cac agg ggc cgc cag acc ctc         240
Val Ser Ser Ser Ser Thr Gln Asp Pro His Arg Gly Arg Gln Thr Leu
    65                  70                  75 ggc agt ctc aga ggc cta gcc aag gcc aaa cca gag gcc tcc ttc cag         288
Gly Ser Leu Arg Gly Leu Ala Lys Ala Lys Pro Glu Ala Ser Phe Gln
80                  85                  90 gtg tgg aac aag gac gta ccc gtt aaa gaa ctg cag ttg aga gct gaa         336
Val Trp Asn Lys Asp Val Pro Val Lys Glu Leu Gln Leu Arg Ala Glu
95                  100                 105                 110 cca act gat ttg cct agg ctt atc gtt tac ttc cag act act cac gac         384
Pro Thr Asp Leu Pro Arg Leu Ile Val Tyr Phe Gln Thr Thr His Asp
                115                 120                 125 tct tcc aac aga cca atc tcc atg ttg cca ttg atc act gag aag ggt         432
Ser Ser Asn Arg Pro Ile Ser Met Leu Pro Leu Ile Thr Glu Lys Gly
            130                 135                 140 atc gct ttg act cac ttg atc gtt tgt tcc ttc cac att aac cag ggt         480
Ile Ala Leu Thr His Leu Ile Val Cys Ser Phe His Ile Asn Gln Gly
    145                 150                 155 ggt gtt gtt cac ttg aac gac ttc cca cca gat gat cca cac ttc tac         528
Gly Val Val His Leu Asn Asp Phe Pro Pro Asp Asp Pro His Phe Tyr
160                 165                 170 act ttg tgg aac gag act atc act atg aag cag gct ggt gtt aag gtt         576
Thr Leu Trp Asn Glu Thr Ile Thr Met Lys Gln Ala Gly Val Lys Val
175                 180                 185                 190 atg gga atg gtt ggt ggt gct gct cct ggt tct ttc aac act cag act         624
Met Gly Met Val Gly Gly Ala Ala Pro Gly Ser Phe Asn Thr Gln Thr
                195                 200                 205 ttg gac tct cca gac tct gct act ttc gag cac tac tac ggt caa ttg         672
Leu Asp Ser Pro Asp Ser Ala Thr Phe Glu His Tyr Tyr Gly Gln Leu
            210                 215                 220 aga gat gct atc gtt aac ttc cag ttg gag gga atg gat ttg gac gtt         720
Arg Asp Ala Ile Val Asn Phe Gln Leu Glu Gly Met Asp Leu Asp Val
    225                 230                 235 gag caa cca atg tcc caa caa ggt atc gac aga ttg atc gct aga ttg         768
Glu Gln Pro Met Ser Gln Gln Gly Ile Asp Arg Leu Ile Ala Arg Leu
240                 245                 250 aga gct gat ttc ggt cca gac ttc ttg att act ttg gct cca gtt gct         816
Arg Ala Asp Phe Gly Pro Asp Phe Leu Ile Thr Leu Ala Pro Val Ala
255                 260                 265                 270
```

```
tct gct ttg gag gac tcc tct aac ttg tct ggt ttc tcc tac act gct      864
Ser Ala Leu Glu Asp Ser Ser Asn Leu Ser Gly Phe Ser Tyr Thr Ala
            275                 280                 285 ttg caa cag act cag ggt aac gac att gac tgg tac aac act cag ttc      912
Leu Gln Gln Thr Gln Gly Asn Asp Ile Asp Trp Tyr Asn Thr Gln Phe
            290                 295                 300 tac tct ggt ttc ggt tct atg gct gac act tcc gac tac gac aga atc      960
Tyr Ser Gly Phe Gly Ser Met Ala Asp Thr Ser Asp Tyr Asp Arg Ile
        305                 310                 315 gtt gct aac ggt ttc gct cca gct aaa gtt gtt gct ggt cag ttg act     1008
Val Ala Asn Gly Phe Ala Pro Ala Lys Val Val Ala Gly Gln Leu Thr
        320                 325                 330 act cct gaa ggt gct gga tgg att cca act tcc tcc ttg aac aac act     1056
Thr Pro Glu Gly Ala Gly Trp Ile Pro Thr Ser Ser Leu Asn Asn Thr
335                 340                 345                 350 atc gtt tcc ttg gtt tcc gag tac ggt caa atc ggt ggt gtt atg gga     1104
Ile Val Ser Leu Val Ser Glu Tyr Gly Gln Ile Gly Gly Val Met Gly
                355                 360                 365 tgg gag tac ttc aat tcc ttg cca ggt ggt act gct gaa cca tgg gag     1152
Trp Glu Tyr Phe Asn Ser Leu Pro Gly Gly Thr Ala Glu Pro Trp Glu
            370                 375                 380 tgg gct caa atc gtt act gag atc ttg aga cca gga ttg gtt cca gag     1200
Trp Ala Gln Ile Val Thr Glu Ile Leu Arg Pro Gly Leu Val Pro Glu
385                 390                 395 ctc aag att act gag gat gac gct gct aga ttg act ggt gct tac gaa     1248
Leu Lys Ile Thr Glu Asp Asp Ala Ala Arg Leu Thr Gly Ala Tyr Glu
        400                 405                 410 gaa tcc gtt aag gct gct gct gct gat aac aag tcc ttc gtt aag agg     1296
Glu Ser Val Lys Ala Ala Ala Ala Asp Asn Lys Ser Phe Val Lys Arg
415                 420                 425                 430 cct tcc atc aac tac tac gct atg gtt aac gct gaa caa aag ctt att     1344
Pro Ser Ile Asn Tyr Tyr Ala Met Val Asn Ala Glu Gln Lys Leu Ile
                435                 440                 445 tct gaa gaa gat ctg taacctcagg                                       1369
Ser Glu Glu Asp Leu
            450

<210> SEQ ID NO 17
<211> LENGTH: 451
<212> TYPE: PRT
<213> ORGANISM: Artificial Sequence
<220> FEATURE:
<223> OTHER INFORMATION: Synthetic Construct

<400> SEQUENCE: 17

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Val Pro Val Lys Glu Leu Gln Leu Arg Ala Glu Pro Thr
            100                 105                 110
```

```
Asp Leu Pro Arg Leu Ile Val Tyr Phe Gln Thr Thr His Asp Ser Ser
            115                 120                 125

Asn Arg Pro Ile Ser Met Leu Pro Leu Ile Thr Glu Lys Gly Ile Ala
130                 135                 140

Leu Thr His Leu Ile Val Cys Ser Phe His Ile Asn Gln Gly Gly Val
145                 150                 155                 160

Val His Leu Asn Asp Phe Pro Pro Asp Asp Pro His Phe Tyr Thr Leu
                165                 170                 175

Trp Asn Glu Thr Ile Thr Met Lys Gln Ala Gly Val Lys Val Met Gly
            180                 185                 190

Met Val Gly Gly Ala Ala Pro Gly Ser Phe Asn Thr Gln Thr Leu Asp
        195                 200                 205

Ser Pro Asp Ser Ala Thr Phe Glu His Tyr Tyr Gly Gln Leu Arg Asp
    210                 215                 220

Ala Ile Val Asn Phe Gln Leu Glu Gly Met Asp Leu Asp Val Glu Gln
225                 230                 235                 240

Pro Met Ser Gln Gln Gly Ile Asp Arg Leu Ile Ala Arg Leu Arg Ala
                245                 250                 255

Asp Phe Gly Pro Asp Phe Leu Ile Thr Leu Ala Pro Val Ala Ser Ala
            260                 265                 270

Leu Glu Asp Ser Ser Asn Leu Ser Gly Phe Ser Tyr Thr Ala Leu Gln
        275                 280                 285

Gln Thr Gln Gly Asn Asp Ile Asp Trp Tyr Asn Thr Gln Phe Tyr Ser
    290                 295                 300

Gly Phe Gly Ser Met Ala Asp Thr Ser Asp Tyr Asp Arg Ile Val Ala
305                 310                 315                 320

Asn Gly Phe Ala Pro Ala Lys Val Val Ala Gly Gln Leu Thr Thr Pro
                325                 330                 335

Glu Gly Ala Gly Trp Ile Pro Thr Ser Ser Leu Asn Asn Thr Ile Val
            340                 345                 350

Ser Leu Val Ser Glu Tyr Gly Gln Ile Gly Gly Val Met Gly Trp Glu
        355                 360                 365

Tyr Phe Asn Ser Leu Pro Gly Gly Thr Ala Glu Pro Trp Glu Trp Ala
    370                 375                 380

Gln Ile Val Thr Glu Ile Leu Arg Pro Gly Leu Val Pro Glu Leu Lys
385                 390                 395                 400

Ile Thr Glu Asp Asp Ala Ala Arg Leu Thr Gly Ala Tyr Glu Glu Ser
                405                 410                 415

Val Lys Ala Ala Ala Asp Asn Lys Ser Phe Val Lys Arg Pro Ser
            420                 425                 430

Ile Asn Tyr Tyr Ala Met Val Asn Ala Glu Gln Lys Leu Ile Ser Glu
        435                 440                 445

Glu Asp Leu
    450

<210> SEQ ID NO 18
<211> LENGTH: 1123
<212> TYPE: DNA
<213> ORGANISM: Artificial Sequence
<220> FEATURE:
<223> OTHER INFORMATION: Fusion protein
<220> FEATURE:
<221> NAME/KEY: CDS
<222> LOCATION: (7)..(1113)

<400> SEQUENCE: 18
```

```
ctcgag atg tgg ctg ggc cgc cgg gcc ctg tgc gct ctg gtc ctt ctg        48
       Met Trp Leu Gly Arg Arg Ala Leu Cys Ala Leu Val Leu Leu
       1               5                  10 ctc gcc tgc gcc tcg ctg ggg ctc ctg tac gcg agc acc gta ccc gtt        96
Leu Ala Cys Ala Ser Leu Gly Leu Leu Tyr Ala Ser Thr Val Pro Val
15              20                  25                  30 aaa gaa ctg cag ttg aga gct gaa cca act gat ttg cct agg ctt atc       144
Lys Glu Leu Gln Leu Arg Ala Glu Pro Thr Asp Leu Pro Arg Leu Ile
                35                  40                  45 gtt tac ttc cag act act cac gac tct tcc aac aga cca atc tcc atg       192
Val Tyr Phe Gln Thr Thr His Asp Ser Ser Asn Arg Pro Ile Ser Met
        50                  55                  60 ttg cca ttg atc act gag aag ggt atc gct ttg act cac ttg atc gtt       240
Leu Pro Leu Ile Thr Glu Lys Gly Ile Ala Leu Thr His Leu Ile Val
65                  70                  75 tgt tcc ttc cac att aac cag ggt ggt gtt gtt cac ttg aac gac ttc       288
Cys Ser Phe His Ile Asn Gln Gly Gly Val Val His Leu Asn Asp Phe
    80                  85                  90 cca cca gat gat cca cac ttc tac act ttg tgg aac gag act atc act       336
Pro Pro Asp Asp Pro His Phe Tyr Thr Leu Trp Asn Glu Thr Ile Thr
95                  100                 105                 110 atg aag cag gct ggt gtt aag gtt atg gga atg gtt ggt ggt gct gct       384
Met Lys Gln Ala Gly Val Lys Val Met Gly Met Val Gly Gly Ala Ala
                115                 120                 125 cct ggt tct ttc aac act cag act ttg gac tct cca gac tct gct act       432
Pro Gly Ser Phe Asn Thr Gln Thr Leu Asp Ser Pro Asp Ser Ala Thr
        130                 135                 140 ttc gag cac tac tac ggt caa ttg aga gat gct atc gtt aac ttc cag       480
Phe Glu His Tyr Tyr Gly Gln Leu Arg Asp Ala Ile Val Asn Phe Gln
145                 150                 155 ttg gag gga atg gat ttg gac gtt gag caa cca atg tcc caa caa ggt       528
Leu Glu Gly Met Asp Leu Asp Val Glu Gln Pro Met Ser Gln Gln Gly
    160                 165                 170 atc gac aga ttg atc gct aga ttg aga gct gat ttc ggt cca gac ttc       576
Ile Asp Arg Leu Ile Ala Arg Leu Arg Ala Asp Phe Gly Pro Asp Phe
175                 180                 185                 190 ttg att act ttg gct cca gtt gct tct gct ttg gag gac tcc tct aac       624
Leu Ile Thr Leu Ala Pro Val Ala Ser Ala Leu Glu Asp Ser Ser Asn
                195                 200                 205 ttg tct ggt ttc tcc tac act gct ttg caa cag act cag ggt aac gac       672
Leu Ser Gly Phe Ser Tyr Thr Ala Leu Gln Gln Thr Gln Gly Asn Asp
        210                 215                 220 att gac tgg tac aac act cag ttc tac tct ggt ttc ggt tct atg gct       720
Ile Asp Trp Tyr Asn Thr Gln Phe Tyr Ser Gly Phe Gly Ser Met Ala
225                 230                 235 gac act tcc gac tac gac aga atc gtt gct aac ggt ttc gct cca gct       768
Asp Thr Ser Asp Tyr Asp Arg Ile Val Ala Asn Gly Phe Ala Pro Ala
    240                 245                 250 aaa gtt gtt gct ggt cag ttg act act cct gaa ggt gct gga tgg att       816
Lys Val Val Ala Gly Gln Leu Thr Thr Pro Glu Gly Ala Gly Trp Ile
255                 260                 265                 270 cca act tcc tcc ttg aac aac act atc gtt tcc ttg gtt tcc gag tac       864
Pro Thr Ser Ser Leu Asn Asn Thr Ile Val Ser Leu Val Ser Glu Tyr
                275                 280                 285 ggt caa atc ggt ggt gtt atg gga tgg gag tac ttc aat tcc ttg cca       912
Gly Gln Ile Gly Gly Val Met Gly Trp Glu Tyr Phe Asn Ser Leu Pro
        290                 295                 300 ggt ggt act gct gaa cca tgg gag tgg gct caa atc gtt act gag atc       960
Gly Gly Thr Ala Glu Pro Trp Glu Trp Ala Gln Ile Val Thr Glu Ile
305                 310                 315
```

```
ttg aga cca gga ttg gtt cca gag ctc aag att act gag gat gac gct      1008
Leu Arg Pro Gly Leu Val Pro Glu Leu Lys Ile Thr Glu Asp Asp Ala
    320                 325                 330 gct aga ttg act ggt gct tac gaa gaa tcc gtt aag gct gct gct gct      1056
Ala Arg Leu Thr Gly Ala Tyr Glu Glu Ser Val Lys Ala Ala Ala Ala
335                 340                 345                 350 gat aac aag tcc ttc gtt aag agg cct tcc atc aac tac tac gct atg      1104
Asp Asn Lys Ser Phe Val Lys Arg Pro Ser Ile Asn Tyr Tyr Ala Met
                355                 360                 365 gtt aac gct taacctcagg                                               1123
Val Asn Ala <210> SEQ ID NO 19
<211> LENGTH: 369
<212> TYPE: PRT
<213> ORGANISM: Artificial Sequence
<220> FEATURE:
<223> OTHER INFORMATION: Synthetic Construct

<400> SEQUENCE: 19

Met Trp Leu Gly Arg Arg Ala Leu Cys Ala Leu Val Leu Leu Leu Ala
1               5                   10                  15

Cys Ala Ser Leu Gly Leu Leu Tyr Ala Ser Thr Val Pro Val Lys Glu
                20                  25                  30

Leu Gln Leu Arg Ala Glu Pro Thr Asp Leu Pro Arg Leu Ile Val Tyr
            35                  40                  45

Phe Gln Thr Thr His Asp Ser Ser Asn Arg Pro Ile Ser Met Leu Pro
        50                  55                  60

Leu Ile Thr Glu Lys Gly Ile Ala Leu Thr His Leu Ile Val Cys Ser
65                  70                  75                  80

Phe His Ile Asn Gln Gly Val Val His Leu Asn Asp Phe Pro Pro
                85                  90                  95

Asp Asp Pro His Phe Tyr Thr Leu Trp Asn Glu Thr Ile Thr Met Lys
            100                 105                 110

Gln Ala Gly Val Lys Val Met Gly Met Val Gly Gly Ala Ala Pro Gly
        115                 120                 125

Ser Phe Asn Thr Gln Thr Leu Asp Ser Pro Asp Ser Ala Thr Phe Glu
130                 135                 140

His Tyr Tyr Gly Gln Leu Arg Asp Ala Ile Val Asn Phe Gln Leu Glu
145                 150                 155                 160

Gly Met Asp Leu Asp Val Glu Gln Pro Met Ser Gln Gln Gly Ile Asp
                165                 170                 175

Arg Leu Ile Ala Arg Leu Arg Ala Asp Phe Gly Pro Asp Phe Leu Ile
            180                 185                 190

Thr Leu Ala Pro Val Ala Ser Ala Leu Glu Asp Ser Ser Asn Leu Ser
        195                 200                 205

Gly Phe Ser Tyr Thr Ala Leu Gln Gln Thr Gln Gly Asn Asp Ile Asp
    210                 215                 220

Trp Tyr Asn Thr Gln Phe Tyr Ser Gly Phe Gly Ser Met Ala Asp Thr
225                 230                 235                 240

Ser Asp Tyr Asp Arg Ile Val Ala Asn Gly Phe Ala Pro Ala Lys Val
                245                 250                 255

Val Ala Gly Gln Leu Thr Thr Pro Glu Gly Ala Gly Trp Ile Pro Thr
            260                 265                 270

Ser Ser Leu Asn Asn Thr Ile Val Ser Leu Val Ser Glu Tyr Gly Gln
        275                 280                 285
```

```
Ile Gly Gly Val Met Gly Trp Glu Tyr Phe Asn Ser Leu Pro Gly Gly
    290             295                 300

Thr Ala Glu Pro Trp Glu Trp Ala Gln Ile Val Thr Glu Ile Leu Arg
305             310                 315                 320

Pro Gly Leu Val Pro Glu Leu Lys Ile Thr Glu Asp Asp Ala Ala Arg
                325                 330                 335

Leu Thr Gly Ala Tyr Glu Glu Ser Val Lys Ala Ala Ala Asp Asn
            340                 345                 350

Lys Ser Phe Val Lys Arg Pro Ser Ile Asn Tyr Tyr Ala Met Val Asn
        355                 360                 365

Ala

<210> SEQ ID NO 20
<211> LENGTH: 1153
<212> TYPE: DNA
<213> ORGANISM: Artificial Sequence
<220> FEATURE:
<223> OTHER INFORMATION: Fusion protein
<220> FEATURE:
<221> NAME/KEY: CDS
<222> LOCATION: (7)..(1143)

<400> SEQUENCE: 20
```

| | | | | | | | | | | | | | | | | |
|---|---|---|---|---|---|---|---|---|---|---|---|---|---|---|---|---|
| ctcgag | atg | tgg | ctg | ggc | cgc | cgg | gcc | ctg | tgc | gct | ctg | gtc | ctt | ctg | | 48 |
| | Met | Trp | Leu | Gly | Arg | Arg | Ala | Leu | Cys | Ala | Leu | Val | Leu | Leu | | |
| | 1 | | | 5 | | | | | 10 | | | | | | | |
| ctc | gcc | tgc | gcc | tcg | ctg | ggg | ctc | ctg | tac | gcg | agc | acc | gta | ccc | gtt | 96 |
| Leu | Ala | Cys | Ala | Ser | Leu | Gly | Leu | Leu | Tyr | Ala | Ser | Thr | Val | Pro | Val | |
| 15 | | | | 20 | | | | | 25 | | | | | 30 | | |
| aaa | gaa | ctg | cag | ttg | aga | gct | gaa | cca | act | gat | ttg | cct | agg | ctt | atc | 144 |
| Lys | Glu | Leu | Gln | Leu | Arg | Ala | Glu | Pro | Thr | Asp | Leu | Pro | Arg | Leu | Ile | |
| | | | 35 | | | | | 40 | | | | | 45 | | | |
| gtt | tac | ttc | cag | act | act | cac | gac | tct | tcc | aac | aga | cca | atc | tcc | atg | 192 |
| Val | Tyr | Phe | Gln | Thr | Thr | His | Asp | Ser | Ser | Asn | Arg | Pro | Ile | Ser | Met | |
| | | | 50 | | | | | 55 | | | | | 60 | | | |
| ttg | cca | ttg | atc | act | gag | aag | ggt | atc | gct | ttg | act | cac | ttg | atc | gtt | 240 |
| Leu | Pro | Leu | Ile | Thr | Glu | Lys | Gly | Ile | Ala | Leu | Thr | His | Leu | Ile | Val | |
| | | | 65 | | | | | 70 | | | | | 75 | | | |
| tgt | tcc | ttc | cac | att | aac | cag | ggt | ggt | gtt | gtt | cac | ttg | aac | gac | ttc | 288 |
| Cys | Ser | Phe | His | Ile | Asn | Gln | Gly | Gly | Val | Val | His | Leu | Asn | Asp | Phe | |
| 80 | | | | | 85 | | | | | 90 | | | | | | |
| cca | cca | gat | gat | cca | cac | ttc | tac | act | ttg | tgg | aac | gag | act | atc | act | 336 |
| Pro | Pro | Asp | Asp | Pro | His | Phe | Tyr | Thr | Leu | Trp | Asn | Glu | Thr | Ile | Thr | |
| 95 | | | | | 100 | | | | | 105 | | | | | 110 | |
| atg | aag | cag | gct | ggt | gtt | aag | gtt | atg | gga | atg | gtt | ggt | ggt | gct | gct | 384 |
| Met | Lys | Gln | Ala | Gly | Val | Lys | Val | Met | Gly | Met | Val | Gly | Gly | Ala | Ala | |
| | | | | 115 | | | | | 120 | | | | | 125 | | |
| cct | ggt | tct | ttc | aac | act | cag | act | ttg | gac | tct | cca | gac | tct | gct | act | 432 |
| Pro | Gly | Ser | Phe | Asn | Thr | Gln | Thr | Leu | Asp | Ser | Pro | Asp | Ser | Ala | Thr | |
| | | | 130 | | | | | 135 | | | | | 140 | | | |
| ttc | gag | cac | tac | tac | ggt | caa | ttg | aga | gat | gct | atc | gtt | aac | ttc | cag | 480 |
| Phe | Glu | His | Tyr | Tyr | Gly | Gln | Leu | Arg | Asp | Ala | Ile | Val | Asn | Phe | Gln | |
| | | | 145 | | | | | 150 | | | | | 155 | | | |
| ttg | gag | gga | atg | gat | ttg | gac | gtt | gag | caa | cca | atg | tcc | caa | caa | ggt | 528 |
| Leu | Glu | Gly | Met | Asp | Leu | Asp | Val | Glu | Gln | Pro | Met | Ser | Gln | Gln | Gly | |
| | | | 160 | | | | | 165 | | | | | 170 | | | |
| atc | gac | aga | ttg | atc | gct | aga | ttg | aga | gct | gat | ttc | ggt | cca | gac | ttc | 576 |
| Ile | Asp | Arg | Leu | Ile | Ala | Arg | Leu | Arg | Ala | Asp | Phe | Gly | Pro | Asp | Phe | |
| 175 | | | | | 180 | | | | | 185 | | | | | 190 | |

```
ttg att act ttg gct cca gtt gct tct gct ttg gag gac tcc tct aac     624
Leu Ile Thr Leu Ala Pro Val Ala Ser Ala Leu Glu Asp Ser Ser Asn
            195                 200                 205 ttg tct ggt ttc tcc tac act gct ttg caa cag act cag ggt aac gac     672
Leu Ser Gly Phe Ser Tyr Thr Ala Leu Gln Gln Thr Gln Gly Asn Asp
        210                 215                 220 att gac tgg tac aac act cag ttc tac tct ggt ttc ggt tct atg gct     720
Ile Asp Trp Tyr Asn Thr Gln Phe Tyr Ser Gly Phe Gly Ser Met Ala
            225                 230                 235 gac act tcc gac tac gac aga atc gtt gct aac ggt ttc gct cca gct     768
Asp Thr Ser Asp Tyr Asp Arg Ile Val Ala Asn Gly Phe Ala Pro Ala
        240                 245                 250 aaa gtt gtt gct ggt cag ttg act act cct gaa ggt gct gga tgg att     816
Lys Val Val Ala Gly Gln Leu Thr Thr Pro Glu Gly Ala Gly Trp Ile
255                 260                 265                 270 cca act tcc tcc ttg aac aac act atc gtt tcc ttg gtt tcc gag tac     864
Pro Thr Ser Ser Leu Asn Asn Thr Ile Val Ser Leu Val Ser Glu Tyr
            275                 280                 285 ggt caa atc ggt ggt gtt atg gga tgg gag tac ttc aat tcc ttg cca     912
Gly Gln Ile Gly Gly Val Met Gly Trp Glu Tyr Phe Asn Ser Leu Pro
        290                 295                 300 ggt ggt act gct gaa cca tgg gag tgg gct caa atc gtt act gag atc     960
Gly Gly Thr Ala Glu Pro Trp Glu Trp Ala Gln Ile Val Thr Glu Ile
            305                 310                 315 ttg aga cca gga ttg gtt cca gag ctc aag att act gag gat gac gct    1008
Leu Arg Pro Gly Leu Val Pro Glu Leu Lys Ile Thr Glu Asp Asp Ala
        320                 325                 330 gct aga ttg act ggt gct tac gaa gaa tcc gtt aag gct gct gct gct    1056
Ala Arg Leu Thr Gly Ala Tyr Glu Glu Ser Val Lys Ala Ala Ala Ala
335                 340                 345                 350 gat aac aag tcc ttc gtt aag agg cct tcc atc aac tac tac gct atg    1104
Asp Asn Lys Ser Phe Val Lys Arg Pro Ser Ile Asn Tyr Tyr Ala Met
            355                 360                 365 gtt aac gct gaa caa aag ctt att tct gaa gaa gat ctg taacctcagg    1153
Val Asn Ala Glu Gln Lys Leu Ile Ser Glu Glu Asp Leu
        370                 375
```

<210> SEQ ID NO 21
<211> LENGTH: 379
<212> TYPE: PRT
<213> ORGANISM: Artificial Sequence
<220> FEATURE:
<223> OTHER INFORMATION: Synthetic Construct

<400> SEQUENCE: 21

```
Met Trp Leu Gly Arg Arg Ala Leu Cys Ala Leu Val Leu Leu Leu Ala
1               5                   10                  15

Cys Ala Ser Leu Gly Leu Leu Tyr Ala Ser Thr Val Pro Val Lys Glu
            20                  25                  30

Leu Gln Leu Arg Ala Glu Pro Thr Asp Leu Pro Arg Leu Ile Val Tyr
        35                  40                  45

Phe Gln Thr Thr His Asp Ser Ser Asn Arg Pro Ile Ser Met Leu Pro
    50                  55                  60

Leu Ile Thr Glu Lys Gly Ile Ala Leu Thr His Leu Ile Val Cys Ser
65                  70                  75                  80

Phe His Ile Asn Gln Gly Gly Val Val His Leu Asn Asp Phe Pro Pro
                85                  90                  95

Asp Asp Pro His Phe Tyr Thr Leu Trp Asn Glu Thr Ile Thr Met Lys
            100                 105                 110
```

Gln Ala Gly Val Lys Val Met Gly Met Val Gly Ala Ala Pro Gly
          115                 120                 125

Ser Phe Asn Thr Gln Thr Leu Asp Ser Pro Asp Ser Ala Thr Phe Glu
    130                 135                 140

His Tyr Tyr Gly Gln Leu Arg Asp Ala Ile Val Asn Phe Gln Leu Glu
145                 150                 155                 160

Gly Met Asp Leu Asp Val Glu Gln Pro Met Ser Gln Gly Ile Asp
                165                 170                 175

Arg Leu Ile Ala Arg Leu Arg Ala Asp Phe Gly Pro Asp Phe Leu Ile
                180                 185                 190

Thr Leu Ala Pro Val Ala Ser Ala Leu Glu Asp Ser Ser Asn Leu Ser
            195                 200                 205

Gly Phe Ser Tyr Thr Ala Leu Gln Gln Thr Gln Gly Asn Asp Ile Asp
    210                 215                 220

Trp Tyr Asn Thr Gln Phe Tyr Ser Gly Phe Gly Ser Met Ala Asp Thr
225                 230                 235                 240

Ser Asp Tyr Asp Arg Ile Val Ala Asn Gly Phe Ala Pro Ala Lys Val
                245                 250                 255

Val Ala Gly Gln Leu Thr Thr Pro Glu Gly Ala Gly Trp Ile Pro Thr
            260                 265                 270

Ser Ser Leu Asn Asn Thr Ile Val Ser Leu Val Ser Glu Tyr Gly Gln
    275                 280                 285

Ile Gly Gly Val Met Gly Trp Glu Tyr Phe Asn Ser Leu Pro Gly Gly
    290                 295                 300

Thr Ala Glu Pro Trp Glu Trp Ala Gln Ile Val Thr Glu Ile Leu Arg
305                 310                 315                 320

Pro Gly Leu Val Pro Glu Leu Lys Ile Thr Glu Asp Asp Ala Ala Arg
                325                 330                 335

Leu Thr Gly Ala Tyr Glu Glu Ser Val Lys Ala Ala Ala Asp Asn
            340                 345                 350

Lys Ser Phe Val Lys Arg Pro Ser Ile Asn Tyr Tyr Ala Met Val Asn
    355                 360                 365

Ala Glu Gln Lys Leu Ile Ser Glu Glu Asp Leu
370                 375

<210> SEQ ID NO 22
<211> LENGTH: 31
<212> TYPE: DNA
<213> ORGANISM: Artificial Sequence
<220> FEATURE:
<223> OTHER INFORMATION: Amplification fragment

<400> SEQUENCE: 22
gcactcgaga tgattcacac caacctgaag a                              31

<210> SEQ ID NO 23
<211> LENGTH: 29
<212> TYPE: DNA
<213> ORGANISM: Artificial Sequence
<220> FEATURE:
<223> OTHER INFORMATION: Amplification fragment

<400> SEQUENCE: 23
ttaacgggta cgtccttgtt ccacacctg                                 29

<210> SEQ ID NO 24
<211> LENGTH: 28
<212> TYPE: DNA

<213> ORGANISM: Artificial Sequence
<220> FEATURE:
<223> OTHER INFORMATION: Amplification fragment

<400> SEQUENCE: 24
gcactcgaga tgtggctggg ccgccggg         28

<210> SEQ ID NO 25
<211> LENGTH: 31
<212> TYPE: DNA
<213> ORGANISM: Artificial Sequence
<220> FEATURE:
<223> OTHER INFORMATION: Amplification fragment

<400> SEQUENCE: 25
ttaacgggta cggtgctcgc gtacaggagc c      31

<210> SEQ ID NO 26
<211> LENGTH: 30
<212> TYPE: DNA
<213> ORGANISM: Artificial Sequence
<220> FEATURE:
<223> OTHER INFORMATION: Amplification fragment

<400> SEQUENCE: 26
gaacaaggac gtacccgtta aagaactgca        30

<210> SEQ ID NO 27
<211> LENGTH: 30
<212> TYPE: DNA
<213> ORGANISM: Artificial Sequence
<220> FEATURE:
<223> OTHER INFORMATION: Amplification fragment

<400> SEQUENCE: 27
cgcgagcacc gtacccgtta aagaactgca        30

<210> SEQ ID NO 28
<211> LENGTH: 32
<212> TYPE: DNA
<213> ORGANISM: Artificial Sequence
<220> FEATURE:
<223> OTHER INFORMATION: Amplification fragment

<400> SEQUENCE: 28
gcacctgagg ttaagcgtta accatagcgt ag     32

<210> SEQ ID NO 29
<211> LENGTH: 72
<212> TYPE: DNA
<213> ORGANISM: Artificial Sequence
<220> FEATURE:
<223> OTHER INFORMATION: Amplification fragment

<400> SEQUENCE: 29
gcacctgagg ttacagatct tcttcagaaa taagcttttg ttcagcgtta accatagcgt    60
agtagttgat gg        72

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30

```
acgtgctggt tattgtgctg                                            20

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
gccagaagtc agatgctcaa gg                                         22

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
atttaggtga cactatag                                              18

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
aatacgactc actataggg                                             19
```

CELLS PRODUCING GLYCOPROTEINS HAVING ALTERED GLYCOSYLATION PATTERNS AND METHOD AND USE THEREOF

CROSS-REFERENCE TO RELATED APPLICATIONS

This application is a continuation of U.S. patent application Ser. No. 12/737,719, filed Apr. 8, 2011, now U.S. Pat. No. 8,815,580, which application is a national phase entry under 35 U.S.C. § 371 of International Patent Application PCT/EP2009/060348, filed Aug. 10, 2009, designating the United States of America and published in English as International Patent Publication WO2010/015722 A1 on Feb. 11, 2010, which claims the benefit under Article 8 of the Patent Cooperation Treaty to European Patent Application Serial Nos. 08162059.3 and 08162063.5, both filed Aug. 8, 2008, the disclosure of each of which is hereby incorporated herein in its entirety by this reference.

TECHNICAL FIELD

The disclosure relates generally to the field of biotechnology and glyco-engineering, more specifically to eukaryotic cells, wherein both an endoglucosaminidase and a glycoprotein are present. These cells can be used to deglycosylate or partly deglycosylate the (exogenous) glycoprotein, in particular, without the need for adding an extra enzyme. Methods are also provided for the application of these cells in protein production. Also envisaged herein is the particular subset of glyco-engineered yeast cells, i.e., yeast cells having at least one exogenous enzyme needed for complex glycosylation in addition to the endoglucosaminidase and the glycoprotein. These cells are particularly useful in providing more homogeneous or easily separable populations of the glycoprotein, which helps considerably in isolating only glycosylated proteins with the desired properties.

BACKGROUND

Glycoproteins are an important class of biomolecules that play crucial roles in many biological events such as cell adhesion, tumor metastasis, pathogen infection, and immune response. Most mammalian cell surface proteins and human serum proteins are glycoproteins and it is not surprising then that therapeutic glycoproteins are an important class of biotechnology products. These include, amongst many others, granulocyte macrophage colony-stimulating factor, tissue plasminogen activator, interleukin-2, erythropoietin (EPO), and antibodies. Both natural and recombinant glycoproteins are typically produced as a mixture of glycoforms that differ only in the structure of the pendent oligosaccharides. This heterogeneity in glycosylation is a major problem in structural and functional studies of glycoproteins (e.g., crystallization studies), as well as in development of glycoprotein drugs. The attached sugar chains may, for instance, have profound effects on protein folding, stability, action, pharmacokinetics, and serum half-life of the glycoprotein, and some sugar chains are very immunogenic.

Glycosylation is one of the most common post-translational modifications of proteins in eukaryotes. N-glycosylation is a highly conserved metabolic process, which in eukaryotes is essential for viability. Protein N-glycosylation originates in the endoplasmic reticulum (ER), where an N-linked oligosaccharide ($Glc_3Man_9GlcNAc_2$) assembled on dolichol (a lipid carrier intermediate) is transferred to the appropriate asparagines residue (Asn) of a nascent protein. This is a co-translational event largely common to all eukaryotic organisms. The three glucose residues and one specific α-1,2-linked mannose residue are removed by specific glucosidases and an α-1,2-mannosidase in the ER, resulting in the core oligosaccharide structure, $Man_8GlcNAc_2$. Proteins with this core sugar structure are transported to the Golgi apparatus where the sugar moiety undergoes various modifications. Glycosyltransferases and mannosidases line the inner (luminal) surface of the ER and Golgi apparatus and thereby provide a catalytic surface that allows for the sequential processing of glycoproteins as they proceed through the ER and Golgi network. The multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases, such that a specific N-glycan structure may be synthesized. There are significant differences in the modifications of the sugar chain in the Golgi apparatus between lower and higher eukaryotes.

In higher eukaryotes, the N-linked oligosaccharides are typically high mannose, complex and mixed (hybrid) types of structures that vary significantly from those produced in yeast (Kornfeld et al., *Ann. Rev. Biochem.* 54:631-664 (1985)). In mammalian cells, the modification of the sugar chain can follow three different pathways depending on the protein moiety to which it is added. That is: (1) the core sugar chain does not change; (2) the core sugar chain is changed by adding the N-acetylglucosamine-1-phosphate moiety (GlcNAc-1-P) in UDP-N-acetyl glucosamine (UDP-GlcNAc) to the 6-position of mannose in the core sugar chain, followed by removal of the GlcNAc moiety to form an acidic sugar chain in the glycoprotein; and (3) the core sugar chain is first converted into $Man_5GlcNAc_2$ by removing three mannose residues with Golgi α-Mannosidase I; $Man_5GlcNAc_2$ is then further modified by adding GlcNAc and removing two more mannose residues, followed by sequentially adding GlcNAc, galactose (Gal), GalNAc, fucose and N-acetylneuraminic acid (also called sialic acid (NeuNAc)) to form various hybrid or complex sugar chains (R. Kornfeld and S. Kornfeld, 1985; Chiba et al., 1998). Different organisms provide different glycosylation enzymes (glycosyltransferases and glycosidases) and different glycosyl substrates, so that the final composition of a sugar side chain may vary markedly depending upon the higher eukaryotic host. Typically, the protein N glycans of animal glycoproteins have bi-, tri-, or tetra-antennary structures. These branched structures are synthesized by the GlcNAc transferase-catalyzed addition of GlcNAc to regions of the oligosaccharide residue. Subsequent to their formation, the antennary structures are terminated with different sugars including Gal, GalNAc, GlcNAc, fucose (Fuc) and sialic acid residues.

In yeast and filamentous fungi (lower eukaryotes), only a part of the $Man_{8(9)}GlcNAc_2$ structures are (partially) trimmed down to $Man_5GlcNAc_2$. These oligosaccharides can then be further modified to fungal-specific glycans through the addition of mannose and/or mannosephosphate residues in a diester linkage. The resulting glycans are known as "high-mannose" type glycans or mannans. For example, yeast glycopeptides include oligosaccharide structures that consist of a high mannose core of 9-13 mannose residues, or extended branched mannan outer chains consisting of up to 200 residues (Ballou et al., *Dev. Biol.* 166:363-379 (1992); Trimble et al., *Glycobiology* 2:57-75 (1992)).

Considerable effort has been directed toward the identification and optimization of new strategies for the preparation of glycopeptides and glycoproteins for therapeutic application. Probably the most documented approach amongst the many promising methods is the engineering of cellular hosts that produce glycopeptides having a desired glycosylation pattern. For a recent review on how this can be achieved, in particular in yeast, see Wildt et al., *Nature Reviews* 2005, 119-28; and Hamilton et al., *Curr. Opin. Biotechnol.* 2007, 18(5):387-92. Other exemplary methods include chemical synthesis, enzymatic synthesis, enzymatic remodeling of formed glycopeptides and, of course, methods that are hybrids or combinations of one or more of these techniques.

Regarding cell host systems, in principle, mammalian, insect, yeast, fungal, plant or prokaryotic cell culture systems, can be used for production of most therapeutic and other glycopeptides in commercially feasible quantities. In practice, however, a desired glycosylation pattern on a recombinantly produced protein is difficult to achieve. For example, bacteria do not N-glycosylate via the dolichol pathway, and yeast only produces oligomannose-type N-glycans, which are not generally found in large quantities in humans. Similarly, plant cells do not produce sialylated oligosaccharides, a common constituent of human glycopeptides. In addition, plants add xylose and/or α-1,3-linked fucose to protein N-glycans, resulting in glycoproteins that differ in structure from animals and are immunogenic in mammals (Lerouge et al., *Plant Mol. Biol.* 1998, 38(1-2): 31-48; Betenbaugh et al., *Curr. Opin. Struct. Biol.* 2004, 14(5):601-6; Altmann, *Int. Arch. Allergy Immunol.* 2007, 142(2):99-115). As recently reviewed, none of the insect cell systems presently available for the production of recombinant mammalian glycopeptides will produce glycopeptides with the same glycans normally found when they are produced in mammals (Harrison and Jarvis, 2006, 159). Moreover, glycosylation patterns of recombinant glycopeptides may also differ when produced under different cell culture conditions (Watson et al., *Biotechnol. Prog.* 10:39-44 (1994); and Gawlitzek et al., *Biotechnol. J.* 42:117-131 (1995)) or even between glycopeptides produced under nominally identical cell culture conditions in two different bioreactors (Kunkel et al., *Biotechnol. Prog.* 2000:462-470 (2000)).

Thus, despite significant advances in this field, heterogeneity of glycosylation remains an issue. Heterogeneity in the glycosylation of recombinantly produced glycopeptides arises because the cellular machinery (e.g., glycosyltransferases and glycosidases) may vary from species to species, cell to cell, or even from individual to individual. The substrates recognized by the various enzymes may be sufficiently different that glycosylation may not occur at some sites or may be vastly modified from that of the native protein. Glycosylation of recombinant proteins produced in heterologous eukaryotic hosts will often differ from the native protein. Therapeutic glycoproteins are typically produced in cell culture systems as a mixture of glycoforms that possess the same peptide backbone but differ in both the nature and site of glycosylation. The heterogeneity in glycosylation poses significant difficulty for the purification, efficacy, as well as therapeutic safety of glycoproteins. Cell and/or glyco-engineering and some biochemical modifications may have yielded cells or (e.g., yeast) strains that produce recombinant glycoproteins with predominant glycoforms but, in most cases, as with natively expressed glycoproteins, the structures that have been obtained remain heterogeneous. Notably, different glycosylation forms can exert significantly different effects on the properties of a given protein, and some glycoforms can even cause allergy problems and undesired immune responses. This is, e.g., particularly true for the high-mannose-type glycoproteins normally produced in yeast. Isolation of a glycoprotein having a particular glycosylation state from such a mixture of glycosylation forms is extremely difficult. However, as small amounts of impurities can dramatically interfere with the desired activities of the glycoprotein of interest, such inhibition is also highly desirable.

In addition to preparing properly glycosylated glycopeptides by engineering the host cell to include the necessary compliment of enzymes, efforts have been directed to the development of both de novo synthesis of glycopeptides and the in vitro enzymatic methods of tailoring the glycosylation of glycopeptides. Although great advances have been made in recent years in both carbohydrate chemistry and the synthesis of glycopeptides (Arsequell et al., *Tetrahedron: Assymetry* 10:3045 (1999)), there are still substantial difficulties associated with chemical synthesis of glycopeptides, particularly with the formation of the ubiquitous β-1,2-cis-mannoside linkage found in mammalian oligosaccharides. Moreover, regio- and stereo-chemical obstacles must be resolved at each step of the de novo synthesis of a carbohydrate.

As enzyme-based syntheses have the advantages of regioselectivity and stereoselectivity, the use of enzymes to synthesize the carbohydrate portions of glycopeptides is a promising approach to preparing glycopeptides. Moreover, enzymatic syntheses can be performed using unprotected substrates. Three principal classes of enzymes are used in the synthesis of carbohydrates, glycosyltransferases (e.g., N-acetylglucosaminyltransferases, oligosaccharyltransferases, sialyltransferases), glycoaminidases (e.g., PNGase F) and glycosidases. The glycosidases are further classified as exoglycosidases (e.g., p-mannosidase, p-glucosidase), and endoglycosidases (e.g., Endo-A, Endo-M). Each of these classes of enzymes has been successfully used synthetically to prepare carbohydrates and glycoproteins. As an example, RNase B has been synthesized as a high-mannose glycosylated protein, after which the oligosaccharide was enzymatically removed (apart from a single GlcNAc) and the correct glycoform was produced in subsequent transglycosylation reactions using different enzymes (Witte et al., *J. Am. Chem. Soc.*, 119:(9)2114-2118, 1997). More examples of how transglycosylation may be used in glycoprotein synthesis are reviewed and described in Crout et al., *Curr. Opin. Chem. Biol.* 2:98-111 (1998); Arsequell, *Tetrahedron:Assymetry* 10:3045 (1999); Murata et al., 1059 (1997); Murata et al., 1049 (2006); WO2003/046150; WO2007/133855; and Koeller et al., *Nature Biotechnology* 18:835-841 (2000). However, for efficient transglycosylation by enzymes, a starting population having a uniform glycosylation profile is still highly desirable (cf., e.g., the single GlcNAc population used by Witte et al., *J. Am. Chem. Soc.* 119:(9)2114-2118, 1997).

A special situation presents itself in crystallization studies of glycoproteins. Here, N-glycosylation often poses a problem. Indeed, when attempting to crystallize a glycoprotein, the results can be improved when using de-N-glycosylated forms of the target protein. However, mutation of the glycosylation site is mostly not an option, since N-glycosylation is needed for protein folding and quality control. At present, endoH-type endoglycosidases are often used for the post-purification deglycosylation of high-mannose type glycoproteins. This approach is successful in many cases but contributes to the complexity of the downstream processing of these often labile proteins. Therefore, it would be advantageous to be able to eliminate downstream processing steps and still obtain a population that can be used for crystallization purposes. A similar situation is observed in glycoproteins that are produced in cells that modify them with immunogenic glycans.

Despite the many advantages of the enzymatic synthesis methods set forth above, in some cases, deficiencies remain. The preparation of properly glycosylated glycopeptides is an exemplary situation in which additional effort is required and effort is being directed to improving both the synthesis of glycopeptides and methods of remodeling biologically or chemically produced glycopeptides that are not properly glycosylated. Thus, there is a need to have a cell system or synthesis method providing homogeneous (uniform) glycosylation on a population of glycoproteins, either already with a correct glycoprofile or as a starting point for subsequent transglycosylation. Alternatively, it would be advantageous to have a cell system or synthesis method providing the possibility of easier isolation of the correctly modified population of glycoproteins from a mixed population of glycoproteins. Particularly also for yeast, it would be advantageous to be able to eliminate downstream processing steps, while still being able to easily separate the desired (complex type) glycoproteins from the undesired, possibly immunogenic glycoforms; or even to obtain yeast cells that no longer produce immunogenic glycoproteins.

DISCLOSURE

Provided are systems and methods for obtaining desired glycosylation profiles of a glycoprotein that are economical in both cost and time. The methods can be cheaper and faster than existing methods because there is no need for adding an enzyme to the produced glycoprotein in order to remove the undesired glycosylation products. Correct glycosylation of the glycoprotein (or an essentially homogeneous glycosylated population of an intermediate glycoform of the glycoprotein) is achieved by producing the glycoprotein and an endoglucosaminidase enzyme in the same cellular system. Also particularly envisaged are glyco-engineered yeast cells and methods with these cells that allow easier isolation of the desired glycoforms of the glycoprotein by selectively deglycosylating the undesired glycoforms, thus allowing easier separation of different glycoforms of secreted proteins. Alternatively, the yeast cells only secrete glycoproteins with the desired (typically complex) glycosylation pattern.

Thus, according to a first aspect, eukaryotic cells are provided with a first exogenous nucleic acid sequence ("polynucleotide") encoding an endoglucosaminidase enzyme and a second exogenous nucleic acid sequence encoding a glycoprotein. According to particular embodiments, the eukaryotic cells do not express an endogenous endoglucosaminidase enzyme. According to alternative particular embodiments, the eukaryotic cells do not express an enzyme with functional endoglucosaminidase activity other than the endoglucosaminidase enzyme encoded by the first exogenous nucleic acid sequence.

That such a strategy works is particularly surprising, since a too strong deglycosylation of cell membrane components by the exogenous endoglucosaminidase would be expected to lead to cell membrane weakening, ultimately leading to cell lysis. This is particularly true for deglycosylation of mannoproteins of the yeast cell wall.

Eukaryotic cells can be of any eukaryotic organism, but in particular, yeast, plant, mammalian and insect cells are envisaged. According to further particular embodiments, the yeast is a *Saccharomyces* species, a *Hansenula* species, a *Yarrowia* species or a *Pichia* species. According to a specific embodiment, the eukaryotic cells are *Pichia* cells. According to an alternative specific embodiment, the mammalian cells are HEK293 cells. According to a very particular embodiment, the eukaryotic cells are not yeast cells.

According to particular embodiments, the cells possess a third exogenous nucleic acid sequence encoding a glycosyltransferase enzyme. According to specific alternative embodiments, the endoglucosaminidase and glycosyltransferase activity are performed by the same enzyme and thus encoded by the same polynucleotide.

According to very specific embodiments, the eukaryotic cells are glyco-engineered yeast cells, i.e., a yeast cell having inactivated endogenous glycosylation enzymes and/or comprising at least a third exogenous nucleic acid sequence encoding at least one enzyme needed for complex glycosylation. Endogenous glycosylation enzymes that could be inactivated include the alpha-1,6-mannosyltransferase Och1p, Alg3p, alpha-1,3-mannosyltransferase of the Mnn1p family, beta-1,2-mannosyltransferases. Enzymes needed for complex glycosylation include, but are not limited to: N-acetylglucosaminyl transferase I, N-acetylglucosaminyl transferase II, mannosidase II, galactosyltransferase, fucosyltransferase and sialyltransferase, and enzymes that are involved in donor sugar nucleotide synthesis or transport. According to particular embodiments, the glyco-engineered yeast cell may be characterized in that at least one enzyme involved in the production of high mannose structures (high mannose-type glycans) is not expressed. Enzymes involved in the production of high mannose structures typically are mannosyltransferases. In particular, alpha-1,6-mannosyltransferase Och1p, Alg3p, alpha-1,3-mannosyltransferase of the Mnn1p family, beta-1,2-mannosyltransferases may not be expressed.

According to particular embodiments, the endoglucosaminidase enzyme encoded by the first exogenous nucleic acid sequence is a mannosyl-glycoprotein endo-beta-N-acetylglucosaminidase, i.e., it has the activity of E.C. 3.2.1.96 in the IUBMB nomenclature. According to further particular embodiments, the endoglucosaminidase is EndoH or EndoT. According to yet further particular embodiments, the endoglucosaminidase is EndoT.

Provided are efficient and easy-to-implement systems for glycoprotein production. Thus, the glycoprotein that is produced by the cell will typically be easily recovered. It may, for instance, be produced in inclusion bodies, membrane-bound organelles or similar structures in the cell. In particular circumstances, recovery may be achieved by cell lysis if the glycoprotein accumulates intracellularly. When cells are part of an organism that is used for production (e.g., a plant instead of a plant cell culture), the glycoprotein may be produced in or transported to specific organs or tissues of the organism from which it can be recovered (e.g., glands or trichomes). According to particular embodiments, however, the glycoprotein is secreted by the cell. This takes away the need for possible refolding or re-activating steps needed when the protein is inactive in inclusion bodies. According to further specific embodiments, the endoglucosaminidase is also secreted by the cell.

Although the endoglucosaminidase may be secreted by the cells described herein, it can be a particular advantage that it remains in the cell. Indeed, this takes away the need for separation of the endoglucosaminidase and the glycoprotein, e.g., when both are secreted. Most particularly, the endoglucosaminidase remains in the cell where it is fully active and, moreover, active at the right place and time. According to a particular embodiment, the endoglucosaminidase is operably linked to an ER or Golgi localization signal. This ensures localization of the endoglucosaminidase to the ER or Golgi, respectively, where it remains in the cell and is in the correct intracellular location to modify the glycosylation of the glycoprotein. Such localization signals are known in the art and may be derived from proteins that are normally localized in the ER or Golgi for their function. According to particular embodiments, the ER or Golgi localization signal is from a protein selected from the group of Ste13p, GM2-synthase, and α-2,6-sialyltransferase. Of note, in the glyco-engineered yeast cells described herein, the at least one enzyme needed for complex glycosylation is/are also localized in the ER or Golgi, to ensure that they successfully modify the glycosylation pathway. This has extensively been described in the art.

The glycosylation status of the produced glycoprotein will depend both from the cellular system used and the specificity of the endoglucosaminidase. In the case of the glyco-engineered yeast cells, this will typically also depend on the enzymes for complex glycosylation present in the cells. Moreover, the time and place where these enzymes act is then also important (e.g., which enzyme acts first in the ER→Golgi pathway).

Thus, it possible that cells will express solely non-glycosylated proteins or proteins having only single GlcNAc residues (e.g., in the case of yeast cells and an endoglucosaminidase capable of hydrolyzing high-mannose and hybrid-type glycans). These proteins can serve as the basis for, e.g., crystallization studies or non-immunogenic glycoproteins. Another (or a further) possibility is that such proteins are further modified, e.g., by treatment with glycosyltransferases, resulting in proteins with the desired glycan moieties.

Alternatively, cells can be used capable of achieving the desired (typically complex) glycosylations. For instance, yeast can be used wherein the endoglucosaminidase acts after the enzymes needed for complex glycosylation (either intracellularly, e.g., in the trans Golgi or trans-Golgi network, or extracellularly). A prerequisite in this scenario is that the endoglucosaminidase does not hydrolyze the desired sugar chains on the glycoproteins. Typically, such cells will produce two populations of glycoproteins: the correctly glycosylated form and a non-glycosylated or single GlcNAc-modified form (obtained, e.g., from deglycosylation of glycoproteins with hybrid-type or mannose-type glycan modifications). Although such mixed population still requires a separation step before a uniformly glycosylated population is obtained, this separation step is much easier than with traditional production methods, as the (e.g., weight) difference between proteins with complex glycosylation and non-glycosylated proteins is much larger than between differently glycosylated proteins.

Alternatively, it is envisaged that the cells produce and/or secrete only correctly glycosylated proteins, e.g., by recycling the non-glycosylated proteins. This may, for instance, be achieved by redirecting non-glycosylated proteins to the ER-Golgi machinery, while glycoproteins with complex glycosylation are secreted. In glyco-engineered yeast cells, the secretion of correctly glycosylated proteins may be achieved, e.g., by targeting the endoglucosaminidase enzyme just before the at least one enzyme for complex glycosylation in the ER→Golgi pathway, in such a way that all glycoproteins are first (at least partly) deglycosylated by the endoglucosaminidase, after which they are modified by the at least one enzyme for complex glycosylation. Using the latter approach, the produced glycoproteins may have non-naturally occurring carbohydrate chains, as the endoglucosaminidase typically will remove the core $Man_5GlcNAc_2$ structure, or at least part thereof, so that the sugar chain added on the glycoprotein by the enzymes for complex glycosylation will be added on shortened base structures, such as a single GlcNAc residue. Although not naturally occurring, such complex sugar chains often also are non-immunogenic and may have other desirable properties, such as, e.g., increased stability, longer half-life, etc.

However, it is understood that, especially in cells other than specific glyco-engineered yeast cells described herein, further (complex) glycosylation may also be inhibited, e.g., in order to retain solely single GlcNAc-modified proteins. This may have advantages with regard to immunogenicity or downstream handling (e.g., for crystallization or for providing a uniform population of glycoproteins). Thus, according to a particular embodiment, the eukaryotic cells described herein do not comprise at least one functional enzyme needed for complex glycosylation, such as ER-mannosidase I, Glucosidase I, Glucosidase II, N-acetylglucosaminyl transferase I, mannosidase II, N-acetylglucosaminyl transferase II. Such cells are not capable of complex glycosylation of glycoproteins. Absence of enzyme activity may be obtained through genetic inactivation strategies such as homology-based knockout, insertion mutagenesis, random mutagenesis, or through transcriptional and/or translational silencing as may be obtained through, for example, siRNA strategies, or through inhibition of the enzyme with chemical inhibitors (e.g., kifunensine for ER-mannosidase-I, castanospermine for glucosidases, or swainsonine for mannosidase II).

Whereas cells for the production of glycoproteins as described herein will typically be provided in the form of a cell culture, this need not necessarily be the case. Indeed, the cells producing the glycoproteins may be part of an organism, e.g., a transgenic animal or plant. According to a particular embodiment, plants comprising the cells containing a glycoprotein and an endoglucosaminidase, as described in the application, are also envisaged.

Also provided in the application are methods using the cells described herein. Particularly, methods are provided for producing single GlcNac-modified glycoproteins in a eukaryotic cell, comprising the steps of:

providing a eukaryotic cell comprising a first exogenous nucleic acid sequence encoding an endoglucosaminidase enzyme and a second exogenous nucleic acid sequence encoding a glycoprotein in conditions suitable for expressing the endoglucosaminidase enzyme and the glycoprotein; and recovering the glycoprotein after it has been intracellularly or extracellularly contacted with the endoglucosaminidase.

The glycoproteins with a single GlcNAc residue may be the only glycoform of the glycoprotein produced by the cell, i.e., a uniform glycopopulation is produced. Alternatively, several glycoforms of the glycoprotein may be produced, but these typically can be easily separated (e.g., proteins with complex glycosylation as well as proteins with single GlcNAc residues). Typically, these several glycoforms will be limited in number (e.g., two glycoforms), as a more or less uniform glycoprofile is desirable. According to particular embodiments, the eukaryotic cells used in the methods described herein are not capable of complex glycosylation of glycoproteins.

Particularly for the specific glyco-engineered yeast cells described herein, methods are provided for producing proteins in a glyco-engineered yeast cell while depleting proteins with high mannose-type glycosylation and/or hybrid-type glycosylation, comprising the steps of:

providing a glyco-engineered yeast cell comprising a first exogenous nucleic acid sequence encoding an endoglucosaminidase enzyme, a second exogenous nucleic acid sequence encoding a glycoprotein, and at least a third exogenous nucleic acid sequence encoding at least one enzyme needed for complex glycosylation, selected from the group consisting of mannosidases and glycosyltransferases other than mannosyltransferases and phosphomannosyltransferases, in conditions suitable for expressing these enzymes and the glycoprotein; and recovering the glycoprotein after it has been intracellularly contacted with the at least one enzyme needed for complex glycosylation and intracellularly or extracellularly contacted with the endoglucosaminidase.

Depleting proteins with high mannose-type glycosylation and/or hybrid-type glycosylation in these yeast cells may result in yeast cells producing glycoproteins as a uniform and homogeneous, typically complex, glycopopulation. Alternatively, several glycoforms of the glycoprotein may be produced, but these typically can be easily separated as no glycoproteins with sugar chains of comparable size to the complex glycans are produced. An example of mixed glycoforms that are produced are proteins with complex glycosylation as well as proteins with single GlcNAc residues.

For all methods, it is true that to ensure that the contact with the endoglucosaminidase occurs under optimal circumstances (i.e., to ensure optimal activity of the endoglucosaminidase on the glycoprotein), the methods may be optimized to suit the desired purpose. For instance, when the contact occurs intracellularly, the endoglucosaminidase may be targeted to the (right place in the) Golgi or ER where it exerts its function on the glycoprotein. According to a particular embodiment, the intracellular contact occurs in the Golgi or ER.

Of note, for the specific glyco-engineered yeast cells, the at least one enzyme needed for complex glycosylation will typically also be localized in (i.e., targeted to) the Golgi or ER, as these are the organelles where the process of glycosylation typically occurs. According to further particular embodiments, the respective targeting signals of the endoglucosaminidase and the enzyme needed for complex glycosylation are chosen in such a way that the enzymes are targeted to different functional regions (endoplasmic reticulum, cis-Golgi network, cis-Golgi, medial Golgi, trans-Golgi, trans-Golgi network) so that they act sequentially. According to yet further particular embodiments, the enzymes are targeted in such a way that they act immediately after each other, e.g., they may be targeted to adjacent compartments in the Golgi apparatus.

When the enzymes are targeted to act sequentially, the glycoprotein may first be contacted with the at least one enzyme needed for complex glycosylation or alternatively with the endoglucosaminidase. According to particular embodiments, the intracellular contact with the endoglucosaminidase occurs in the Golgi or ER, after contact with the at least one enzyme needed for complex glycosylation.

Although the endoglucosaminidase, like the at least one enzyme needed for complex glycosylation, may be retained in the cell (and, in particular, within the ER→Golgi region where glycosylation occurs), in case the glycoprotein is secreted, it is also possible for the endoglucosaminidase to be secreted and the contact between glycoprotein may happen extracellularly. In this case, the (intracellular) contact with the at least one enzyme needed for complex glycosylation takes place before the (extracellular) contact with the endoglucosaminidase.

For all of the cells described herein, methods may imply that both proteins may also be secreted and the contact may happen extracellularly. Depending on the cells and endoglucosaminidase that are used, however, the optimal growth conditions for the cells (e.g., pH, temperature, nature of medium) may differ from the optimal conditions for enzymatic activity. Thus, the medium where the extracellular contact between the glycoprotein and the endoglucosaminidase takes place may be adjusted for optimal enzymatic activity of the endoglucosaminidase. According to a particular embodiment, the conditions of the medium wherein the extracellular contact takes place are adjusted for optimal enzymatic endoglucosaminidase activity. According to a further particular embodiment, the pH of the medium wherein the extracellular contact takes place is adjusted for optimal enzymatic endoglucosaminidase activity. Typically, this may be done by a pH shift of the medium after the cells have been allowed to produce and secrete both glycoproteins and endoglucosaminidases. In general, such pH shift will be a downshift, as endoglucosaminidases usually are physiologically active in an acidic environment (e.g., the Golgi apparatus within a cell). Alternatively, the cells may be grown in a medium with a pH that is both permissive for growth and enzymatic activity, so that no pH shift is necessary. According to another particular embodiment, the temperature of the medium is adjusted for optimal enzymatic activity. According to yet another particular embodiment, the nature of the medium (e.g., salt or ion content and/or concentration) is adjusted for optimal enzymatic activity.

According to a particular aspect, the protein modified with the single GlcNAc residues is not the end-point. Methods according to this aspect will include at least one additional glycosylation step. According to this embodiment, before the final recovery of the glycoprotein, the methods further involve a step of contacting the enzyme with a glycosyltransferase after it has been intracellularly or extracellularly contacted with the endoglucosaminidase. Optionally, this contacting with a glycosyltransferase may occur in the presence of specific glycosyl donors (e.g., sugar nucleotide donors) to ensure efficient and correct glycosylation. This will especially be the case when the glycosylation takes place extracellularly.

If the transglycosylation step takes place intracellularly, it will be understood by the skilled person that, when both the endoglucosaminidase enzyme and the glycosyltransferase enzyme are targeted to the ER or Golgi, it is ensured that the glycosyltransferase activity occurs after the endoglucosaminidase activity. Typically, this may be ensured by targeting both enzymes to different compartments of the ER or Golgi, as there is a fixed order in which proteins follow the ER→Golgi route. In the event both enzymes are targeted to the same compartment, or that both activities are performed by the same enzyme, it typically will be ensured that the protein after the transglycosylation step is no longer recognized as substrate for the endoglucosaminidase enzyme. Thus, separation of the enzymatic activities in time may involve spatial separation and/or a different substrate specificity. According to a particular embodiment, both the endoglucosaminidase and the glycosyltransferase are produced by the same cell, but only the glycosyltransferase is secreted, to ensure transglycosylation takes place after the endoglucosaminidase activity.

Depending on how the method is performed, the glycosyltransferase enzyme may be added extracellularly (i.e., is not produced by the same cells), is also produced and secreted by the cells producing the glycoprotein and endoglucosaminidase, or is also produced by the cells and retained within the ER or Golgi apparatus. The glycosyltransferase may be encoded by an exogenous sequence, or may be an enzyme that is endogenous in the cells having a first exogenous nucleic acid sequence encoding an endoglucosaminidase enzyme and a second exogenous nucleic acid sequence encoding a glycoprotein.

BRIEF DESCRIPTION OF THE FIGURES

FIG. 4A, Glycan profiles of wild-type GS115 or FIG. 4B, Man5-glyco-engineered *Pichia* strains not expressing EndoT (panels 2) or soluble overexpressing different EndoT forms (N-terminal truncated, C-terminal truncated, both N- and C-terminal truncated or full size). The vertical axis is presented in values of Relative Fluorescence Units.

FIG. 5A, Gal2GlNAc2Man3 strain; FIG. 5B, Gal-GlcNacMan3 strain; FIG. 5C, GalGlcNAcMan5 strain; FIG. 5D, GlcNAcMan5 strain; FIG. 5E, Man5 strain; and FIG. 5F, WT GS115 strain. Panel 2, PNGase F treatments; Panel 3, EndoH treatment; Panel 4, EndoT treatment; Panel 5, EndoH treatment followed by PNGase F treatment; Panel 6, EndoT treatment followed by PNGase F treatment; Panel 7, RNase B treatment. In panel 5 of FIG. 5F a contaminating polymer is present. The vertical axis is presented in values of Relative Fluorescence Units.

DETAILED DESCRIPTION

Definitions

Figure 1:
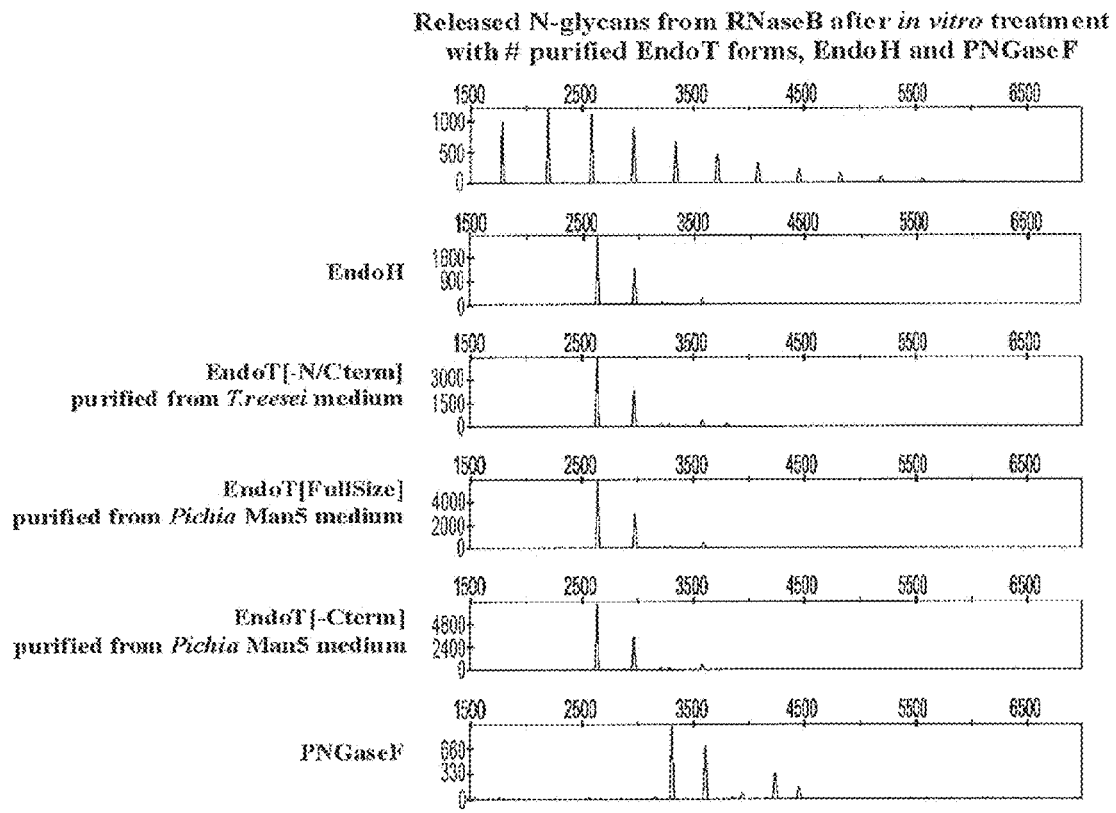
FIG. 1: Released N-glycans from RNase B after in vitro treatment with EndoH (second panel), different purified forms of EndoT (as indicated) (panels 3-5) and PNGase F (panel 6).

The disclosure will be described with respect to particular embodiments and with reference to certain drawings but the disclosure is not limited thereto; only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present disclosure, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third" and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of the present disclosure. Practitioners are particularly directed to Sambrook et al., *Molecular Cloning: A Laboratory Manual*, $2^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

"Glyco-engineered yeast cells," as used in the application, are yeast cells that express at least one exogenous nucleic acid sequence encoding an enzyme needed for complex glycosylation that is not expressed in the wild-type yeast, and/or that do not express at least one enzyme involved in the production of high-mannose type structures that is normally expressed in the wild-type yeast.

An "endoglucosaminidase," as used herein, refers to enzymes that hydrolyze the bond between the anomeric carbon of a non-terminal beta-linked N-acetylglucosamine residue in an oligosaccharide of a glycoprotein or a glycolipid, and its aglycon, thereby releasing mono- or oligosaccharides from glycoproteins or glycolipids or sugar polymers. Endoglucosaminidases are a subset of the glycosidases, and may or may not have other enzymatic activities (such as, e.g., glycosyltransferase activity). A particular class of endoglucosaminidases is formed by the endo-β-N-acetylglucosaminidases or mannosyl-glycoprotein endo-β-N-acetylglucosaminidases, indicated as EC 3.2.1.96 in the International Union of Biochemistry and Molecular Biology (IUBMB) nomenclature. This particular class of enzymes are capable of catalyzing the endohydrolysis of the N,N'-diacetylchitobiosyl unit in high-mannose glycopeptides and glycoproteins containing the -[Man (GlcNAc)$_2$]Asn- structure. One N-acetyl-D-glucosamine (GlcNAc) residue remains attached to the protein; the rest of the oligosaccharide is released intact. Thus, the result is a single GlcNAc-modified glycoprotein. Of note, the remaining GlcNAc residue may be either unmodified or still be modified with other sugar residues in other positions than that of the hydrolyzed bond, for instance, the GlcNAc residue may carry a fucose on position 3 or 6. Nevertheless, glycoproteins with a modified GlcNAc residue will still be referred to as single GlcNAc-modified proteins, as there is no second sugar residue on position 4 of the GlcNAc residue (i.e., there is no typical sugar chain). A particular advantage of endoglucosaminidases as compared to exoglycosidases is that they allow discrimination between N-linked and O-linked glycans and between classes of glycans. A non-limiting list of endoglucosaminidases is provided in the application.

Particularly with regard to the glyco-engineered yeast cells, an "enzyme needed for complex glycosylation," as used herein, refers to any enzyme not naturally occurring in the host yeast cell that may be involved in the synthesis of complex glycans as found in higher eukaryotes, in particular, as found in mammals, more in particular, as found in humans. Most particularly, such enzymes are enzymes that remove mannose residues from the sugar chain (i.e., mannosidases) or glycosyltransferases, in particular, glycosyltransferases other than mannosyltransferases (i.e., glycosyltransferases that transfer monosaccharides that are not found in high-mannose glycans) and/or phosphomannosyltransferases.

A "glycosyltransferase" as used in the application is any of a group of enzymes that catalyze the transfer of glycosyl groups in biochemical reactions, in particular, glycosyl transfer to asparagine-linked sugar residues to give N-linked glycoproteins. Glycosyltransferases fall under EC 2.4 in the IUBMB nomenclature, a particular class of glycosyltransferases are hexosyltransferases (EC 2.4.1). Among the wide variety of these post-translational enzymes that process peptides into glycoproteins are enzymes such as, but not limited to, N-acetylglucosaminyl transferases, N-acetylgalactosaminyltransferases, sialyltransferases, fucosyltransferases, galactosyltransferases, and mannosyltransferases.

Note that exogenous mannosyltransferases are excluded for specific embodiments of glyco-engineered yeast cells described in the application. "Mannosyltransferases" as used in the application refers to enzymes that catalyze the transfer of a mannosyl group to an acceptor molecule, typically another carbohydrate, in the Golgi apparatus. Mannosyltransferases are typically endogenous enzymes in yeast and involved in the synthesis of high-mannose type glycans.

Of note, an enzyme may possess both endoglucosaminidase and glycosyltransferase activity. Although it may be possible to use one enzyme to exert these two activities, typically, the enzymes used will fulfill only one function. Thus, it is envisaged to use enzymes that have been modified or mutated to make sure they perform only one function, or that have been modified or mutated to ensure they carry out a specific function more efficiently. Such modified enzymes are known in the art.

"Glycoproteins" as used in the application refers to proteins that, in their normal physiological context and/or their functional form, contain oligosaccharide chains (glycans) covalently attached to their polypeptide side-chains. The carbohydrate may be attached to the protein in a co-translational or post-translational modification. In particular, "glycoproteins" as used herein are proteins that show N-glycosylation in their physiologically active form. Thus, glycoproteins typically contain a sugar chain at least on one asparagine residue. A non-limiting list of glycoproteins is provided in the specification. The term "glycoproteins" is not intended to refer to the length of the amino acid chain, "glycopeptides" are included within the definition of "glycoproteins."

The terms "(glyco)protein" and "enzyme" (e.g., endoglucosaminidase, glycosyltransferase, mannosidase, mannosyltransferase) as used in the application are also intended to cover functionally active fragments and variants of the naturally occurring proteins. Indeed, for many (e.g., therapeutic) proteins, part of the protein may be sufficient to achieve an (e.g., therapeutic, enzymatic) effect. The same applies for variants (i.e., proteins in which one or more amino acids have been substituted with other amino acids, but which retain functionality or even show improved functionality), in particular, for variants of the enzymes optimized for enzymatic activity.

In the context of the application, a glycoprotein refers to the protein itself; a glycoprotein may be either in its glycosylated or non-glycosylated form. A "glycosylated" protein is a (glyco)protein that carries at least one oligosaccharide chain.

A "sugar chain," "oligosaccharide chain" or "carbohydrate chain," as used herein, is a chain of two or more monosaccharides. As a consequence, a protein carrying only a single monosaccharide (e.g., a single GlcNAc residue) will usually, unless specified otherwise, not be referred to as a glycosylated protein, but as a protein that carries a monosaccharide, or a monosaccharide (e.g., GlcNAc)-modified protein. Typical monosaccharides that may be included in an oligosaccharide chain of a glycoprotein include, but are not limited to, glucose (Glu), galactose (Gal), mannose (Man), fucose (Fuc), N-acetylneuraminic acid (NeuAc) or another sialic acid, N-acetylglucosamine (GlcNAc), N-acetylgalactosamine (GalNAc), xylose (Xyl) and derivatives thereof (e.g., phosphoderivatives). Sugar chains may be branched or not, and may comprise one or more types of oligosaccharide. In general, sugar chains in N-linked glycosylation may be divided in three types: high-mannose, complex and hybrid type glycosylation. These terms are well known to the skilled person and defined in the literature. Briefly, high-mannose type glycosylation typically refers to oligosaccharide chains comprising two N-acetylglucosamines with (possibly many) mannose and/or mannosylphosphate residues (but typically no other monosaccharides).

Complex glycosylation typically refers to structures with typically one, two or more (e.g., up to six) outer branches with a sialyllactosamine sequence, most often linked to an inner core structure $Man_3GlcNAc_2$. For instance, a complex N-glycan may have at least one branch, or at least two, of alternating GlcNAc and galactose (Gal) residues that may terminate in a variety of oligosaccharides but typically will not terminate with a mannose residue.

Hybrid type glycosylation covers the intermediate forms, i.e., those glycosylated proteins carrying both terminal mannose and terminal non-mannose residues in addition to the two N-acetylglucosamine residues. In contrast to complex glycosylation, at least one branch of hybrid type glycosylation structures ends in a mannose residue.

Although this classification is most often used to describe naturally occurring glycans on proteins, it is evident that synthetic and/or non-naturally occurring sugars can also be classified this way, even if their structures diverge from the classical example. For instance, a sugar chain consisting of a single branch of a galactose and a sialic acid residue linked to a single GlcNAc would be a complex sugar, even though it lacks the inner core $Man_3GlcNAc_2$.

An "ER localization signal" or a "Golgi localization signal" is a molecule, typically a peptide that directs localization of the polypeptide or protein to which it is conjugated to the ER or Golgi apparatus, respectively. Localization thus also implies retention in the ER or Golgi apparatus, respectively. Typically, these localization (or retention) sequences are peptide sequences derived from (pre)proteins that are situated in the ER or Golgi when functionally active as a mature protein.

The disclosure aims to provide cells producing glycoproteins with an altered glycosylation pattern, in particular, a more homogeneous glycosylation pattern, that makes them more amenable for further use, e.g., therapeutic use, or use in crystallization studies. This is achieved, according to a first aspect, by providing eukaryotic cells with a first exogenous nucleic acid sequence encoding an endoglucosaminidase enzyme and a second exogenous nucleic acid sequence encoding a glycoprotein. The nature of the glycoprotein is not critical, but glycoproteins will typically be proteins relevant for medicine and/or industry for which correct N-glycosylation is important for their function. Non-limiting examples include many hormones, growth factors, cytokines and their corresponding receptors, such as follicle-stimulating hormone (FSH), luteinizing hormone (LH), thyroid-stimulating hormone (TSH), epidermal growth factor (EGF), human epidermal growth factor receptor-2 (HER-2), fibroblast growth factor-alpha (FGF-α), fibroblast growth factor-beta (FGF-β), transforming growth factor-alpha (TGF-α), transforming growth factor-beta (TGF-β), platelet-derived growth factor (PDGF), insulin-like growth factor-1 (IGF-1), insulin-like growth factor-2 (IGF-2), nerve growth factor (NGF), nerve growth factor-beta (NGF-β); receptors of the aforementioned, growth hormones (e.g., human growth hormone, bovine growth hormone); insulin (e.g., insulin A chain and insulin B chain), proinsulin; erythropoietin (EPO); colony-stimulating factors (e.g., granulocyte colony-stimulating factor (G-CSF), granulocyte macrophage colony-stimulating factor (GM-CSF), macrophage colony-stimulating factor (M-CSF)); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; calcitonin; CD proteins (e.g., CD3, CD4, CD8, CD28, CD19, etc.); CTLA proteins (e.g., CTLA4); T-cell and B-cell receptor proteins; bone morphogenic proteins (BMPs, e.g., BMP-1, BMP-2, BMP-3, etc.); neurotrophic factors, e.g., bone-derived neurotrophic factor (BDNF); neurotrophins, e.g., 3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; alkaline phosphatase; lectins; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art, including fusion or chimeric proteins of the above. Fragments or portions, or mutants, variants, or analogues of any of the aforementioned proteins and polypeptides are also included among the suitable proteins, polypeptides and peptides that can be produced by the cells and methods presented herein.

The nature of the endoglucosaminidase will depend on the desired glycopopulation of the glycoproteins. For instance, endoglucosaminidases may be selected for their substrate specificity. Some endoglucosaminidases, e.g., EndoH and EndoT, hydrolyze high-mannose type sugar chains and hybrid type sugars, but leave complex carbohydrate structures intact. Such enzymes are ideal, e.g., for obtaining single GlcNAc-modified glycoproteins from cells incapable of complex glycosylation, or for removing contaminating high-mannose and/or hybrid type sugars in cells producing complex glycosylated proteins as well as other glycoforms (such as most glyco-engineered yeast strains). According to particular embodiments, the endoglucosaminidase hydrolyzes high mannose-type sugar chains and hybrid-type glycans, but not complex-type glycans.

Endoglucosaminidases may also have substrate specificity with regard to the glycoprotein (instead of only the sugar chain), some endoglucosaminidases are, e.g., more successful in hydrolyzing sugar chains from (particularly compactly folded) proteins than other endoglucosaminidases (e.g., EndoT); others may (also) be particularly successful in hydrolyzing sugar chains from glycopeptides or not-compactly folded proteins (e.g., EndoH, EndoT). Importantly, as this typically has to do with access to or availability of the substrate rather than with the specificity of the endoglucosaminidase, this does not exclude the use of certain enzymes for specific proteins, but some endoglucosaminidases may require more time to complete the hydrolysis of all N-linked sugar structures.

The choice of endoglucosaminidases may also depend on the resulting product(s). For instance, when different glycopopulations are secreted (e.g., complex-type glycosylated proteins that are not hydrolyzed and other types that are hydrolyzed), it may be important that the resulting proteins can be easily separated. As another example, when further transglycosylation is envisaged, endoglucosaminidases leaving single GlcNAc-modified proteins (e.g., EndoH, EndoT) are particularly envisaged, as the single GlcNAc residue on the protein offers a suitable substrate for the glycosyltransferase to attach the sugar modification. This is a significant advantage of the eukaryotic cells described herein as compared to bacterial expression systems, as the bacteria cannot produce single GlcNAc-modified glycoproteins, which makes it much more difficult to use proteins produced in bacteria as starting point for transglycosylation. Alternatively, single GlcNAc-modified proteins can be used in crystallization studies, although this is also true for non-glycosylated proteins. Thus, endoglucosaminidases removing the whole sugar chain without leaving a monosaccharide on the protein (such as peptide-N-glycosidase F) may be envisaged when using the produced glycoproteins for crystallization. Another consideration may be the presence or absence of other enzymatic activities, such as glycosyltransferase activity. EndoA, EndoBH and EndoM, for instance, are known to possess such glycosyltransferase activity, and it may for some embodiments be desirable to work with mutants that no longer possess this activity.

A particular class of endoglucosaminidases is formed by the mannosyl-glycoprotein endo-β-N-acetylglucosaminidases, indicated as EC 3.2.1.96 in the IUBMB nomenclature. These enzymes can remove sugar chains while leaving one GlcNAc residue on the protein. Examples of these include, but are not limited to, EndoA, EndoBH, EndoCE, EndoD, EndoF1, EndoF2, EndoF3, EndoH, EndoM, EndoT (see, also WO2006/050584), AcmA, and ENGase. Other examples are known to the skilled person and can, for instance, be found on the World Wide Web at cazy.org, in particular, under the Glycoside Hydrolase Families 85 and 18. Particularly envisaged is the use of the EndoT enzyme from *Hypocrea jecorina* (formerly known as *Trichoderma reesei*) that is described in WO2006/050584 (see, e.g., SEQ ID NOS:9-12 therein).

According to particular embodiments, the eukaryotic cells do not express an endogenous endoglucosaminidase enzyme, in particular, no mannosyl-glycoprotein endo-β-N-acetylglucosaminidase. According to alternative particular embodiments, the eukaryotic cells do not express an enzyme with functional endoglucosaminidase activity other than the endoglucosaminidase enzyme encoded by the first exogenous nucleic acid sequence. That is, they may, for instance, express another endoglucosaminidase, but an endoglucosaminidase that is modified to no longer have its hydrolase activity (but, e.g., only its glycosyltransferase activity, so that it can function in the synthesis of complex glycosylation structures).

The eukaryotic cells as described herein may produce uniformly, single GlcNAc-modified glycoproteins that are ready to use (e.g., for crystallization studies), or that may be used as a starting point for further glycomodification reactions, e.g., by glycosyltransferases. Alternatively, the eukaryotic cells may produce two populations of easily separable, differentially glycosylated glycoproteins, one population of which is typically single GlcNAc-modified. The other will in such case typically have a complex glycosylation pattern, although this is not strictly required.

Glycosyltransferases have been used to modify the oligosaccharide structures on glycopeptides, and have been shown to be very effective for producing specific products with good stereochemical and regiochemical control. Glycosyltransferases may be used to prepare oligosaccharides and to modify terminal N- and O-linked carbohydrate structures on glycopeptides produced in eukaryotic cells. For example, the terminal oligosaccharides may be completely sialylated and/or fucosylated to create sugar structures that improve glycoprotein (or glycopeptides) pharmacodynamics and a variety of other biological properties, such as, e.g., immunogenicity. Such glycosyltransferases may be used in natural or synthetic pathways, for instance, fucosyltransferases have been used in synthetic pathways to transfer a fucose unit from guanosine-5'-diphosphofucose to a specific hydroxyl of a saccharide acceptor (Ichikawa et al., *J. Am. Chem. Soc.* 114:9283-9298 (1992)).

Under appropriate conditions, both exoglycosidases and endoglycosidases have been shown to possess glycosyl transferase activity. Methods based on the use of endoglycosidases have the advantage that an oligosaccharide, rather than a monosaccharide, is transferred. The above enzymes can be utilized in the generation of carbohydrates (that are, e.g., to be conjugated to glycoproteins) as well as glycosylated glycoproteins themselves. For examples of how glycosyltransferases may be used in the further processing of, e.g., single GlcNAc-modified glycoproteins, see, e.g., Takegawa *JBC* 3094, Koeller et al., 835, *Nat. Biotech.* 2000; WO03/046150, and WO07/133855.

However, instead of delivering the intermediary glycoprotein product that is to be used in further transglycosylation steps with a glycosyltransferase that needs to be added, it is also envisaged that the cells described herein may themselves produce the glycosyltransferase(s). Indeed, it is envisaged that the glycosyltransferase(s) of the cells perform a glycosylation reaction on the glycoproteins, either within the cells or in the extracellular environment, thereby yielding a uniform population of glycoproteins with the desired (typically complex) glycosylation profile.

Thus, according to particular embodiments, the cells possess a third exogenous nucleic acid sequence encoding a glycosyltransferase enzyme. According to specific alternative embodiments, the endoglucosaminidase and glycosyltransferase activity are performed by the same enzyme. This may be because there is only one enzyme and both activities are thus encoded by the same sequence (although it is also possible that the enzyme sequence is identical, but the localization or secretion sequence differs). Alternatively, it is envisaged that two versions of the same enzyme are expressed in the cell (e.g., EndoT, EndoM), one that has endoglucosaminidase activity but (preferably) no glycosyltransferase activity, and one that has only glycosyltransferase activity. If an enzyme is used that still has both activities, it is important to control (spatiotemporal) access to its substrate, in order to avoid interference of the two enzymatic activities. For instance, when the enzyme and glycoprotein are secreted, the endoglucosaminidase activity may be activated first (e.g., by adapting pH), after which substrates for transglycosylation can be added to the medium. Even so, it should be ensured that the endoglucosaminidase is not able to hydrolyze the glycoprotein after it has been modified with a sugar chain by the glycosyltransferase activity.

According to particular embodiments, however, the glycosyltransferase is not encoded by the same sequence as the endoglucosaminidase. According to further particular embodiments, one or more glycosyltransferases different from the endoglucosaminidases are used. Examples include, but are not limited to, sialyltransferases such as α-sialyltransferases, galactosyltransferases such as β-1,4-galactosyltransferase, and fucosyltransferases.

According to alternative, but not necessarily exclusive, particular embodiments, the cells are glyco-engineered yeast cells, i.e., yeast cells that also possess at least a third exogenous nucleic acid sequence encoding at least one enzyme needed for complex glycosylation, and/or are deficient in the activity of at least one endogenous glycosyltransferase. According to particular embodiments, the enzyme needed for complex glycosylation is a mannosidase or a glycosyltransferase other than a mannosyltransferase. According to further particular embodiments, the at least one enzyme needed for complex glycosylation is selected from the group consisting of N-acetylglucosaminyl transferase I, N-acetylglucosaminyl transferase II, mannosidase II, galactosyltransferase, and sialyltransferase.

According to particular embodiments, the glyco-engineered yeast cell may be characterized in that at least one enzyme involved in the production of high mannose structures (high mannose-type glycans) is not expressed (or is not functionally active in the cell). According to further particular embodiments, at least one mannosyltransferase is not expressed in the glyco-engineered yeast cell. Typically, the mannosyltransferase that is not expressed in the glyco-engineered yeast cell is expressed in the wild-type counterpart of the yeast cell. According to yet further particular embodiments, the mannosyltransferase is a α-1,2-mannosyltransferase, α-1,3-mannosyltransferase, α-1,6-mannosyltransferase, or β-1,4-mannosyltransferase. These proteins often have specific names in yeast (e.g., Alg, Och, Mnn), but their activities are well known in the art. Alternatively or additionally, at least one mannosylphosphate transferase is not functionally active in the glyco-engineered yeast cell.

In the eukaryotic cells described herein, the glycosyltransferase may, just like the endoglucosaminidase, be secreted or be retained in the cell, in particular, targeted to the ER or Golgi. In the latter case, it will typically be targeted to a later stage of the ER→Golgi assembly pathway for glycosylated proteins, to ensure that the proteins are (partly) deglycosylated by the endoglucosaminidase first, after which they are subject to transglycosylation by the glycosyltransferase. This way, depending on the combinations of endoglucosaminidase(s) and glycosyltransferase(s), naturally occurring as well as synthetic glycans can be added to the glycoproteins.

Eukaryotic cells can be of any eukaryotic organism, but, in particular embodiments, yeast, plant, mammalian and insect cells are envisaged. The nature of the cells used will typically depend on the desired glycosylation properties and/or the ease and cost of producing the glycoprotein. Mammalian cells may, for instance, be used for achieving complex glycosylation and avoiding problems with immunogenicity, but it may not be cost-effective to produce proteins in mammalian cell systems. Plant and insect cells, as well as yeast, typically achieve high production levels and are more cost-effective, but additional modifications may be needed to mimic the complex glycosylation patterns of mammalian proteins, or to reduce problems with immunogenicity. Eukaryotic cell lines for protein production are well known in the art, including cell lines with modified glycosylation pathways. Nonlimiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, *Som. Cell Molec. Genet.*, 12:555-556; and Kolkekar et al., 1997, *Biochemistry*, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, *Proc. Natl. Acad. Sci. USA*, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, *J. Gen. Virol.*, 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals N. Y. Acad. Sci.*, 383:44-68); MCR 5 cells; FS4 cells. Exemplary non-mammalian cell lines include, but are not limited to, Sf9 cells, baculovirus-insect cell systems (e.g., review Jarvis, *Virology Volume* 310, Issue 1, 25 May 2003, pages 1-7), plant cells such as tobacco cells, tomato cells, maize cells, algae cells, or yeasts such as *Saccharomyces* species, *Hansenula* species, *Yarrowia* species or *Pichia* species. According to particular embodiments, the eukaryotic cells are yeast cells from a *Saccharomyces* species (e.g., *Saccharomyces cerevisiae*), a *Hansenula* species (e.g., *Hansenula polymorpha*), a *Yarrowia* species (e.g., *Yarrowia lipolytica*), a *Kluyveromyces* species (e.g., *Kluyveromyces lactis*) or a *Pichia* species (e.g., *Pichia pastoris*). According to a specific embodiment, the eukaryotic cells are *Pichia* cells, and in a most particular embodiment, *Pichia pastoris* cells. *Pichia pastoris* has been shown to have a secretory pathway with distinct Golgi stacks similar to those found in mammalian cells.

According to an alternative particular embodiment, the cells are mammalian cells selected from Hek293 cells or COS cells.

The eukaryotic (or specifically yeast) cells as described herein may produce uniformly, complex-type glycosylated glycoproteins that are ready to use. Alternatively, the eukaryotic cells may produce two populations of easily separable, differentially glycosylated glycoproteins, one population of which typically shows complex type glycosylation, the other typically (though not necessarily) is single GlcNAc-modified.

According to particular embodiments, the endoglucosaminidase enzyme encoded by the first exogenous nucleic acid sequence is a mannosyl-glycoprotein endo-beta-N-acetylglucosaminidase, i.e., it has the activity of E.C. 3.2.1.96 in the IUBMB nomenclature, implying that it can remove sugar chains while leaving one GlcNAc residue on the protein. According to alternative embodiments, the endoglucosaminidase encoded by the first exogenous nucleic acid sequence has different affinities toward different types of glycosylation structures. Typical examples of the latter are endoglucosaminidases that are able to hydrolyze hybrid type sugars and/or high-mannose sugars, but are not capable of cleaving complex type glycans. According to further particular embodiments, the endoglucosaminidase is a mannosyl-glycoprotein endo-beta-N-acetylglucosaminidase that has different affinities toward different types of glycosylation structures. According to yet further particular embodiments, the endo-beta-N-acetylglucosaminidase is able to cleave hybrid type sugars and/or high-mannose sugars, but not complex type glycans. According to even more particular embodiments, the endoglucosaminidase is EndoH or EndoT. According to most particular embodiments, the endoglucosaminidase is EndoT.

The glycoproteins produced by the cells described herein typically should be easily recovered. This will particularly be achieved by secretion of the glycoprotein. This can be after contact with the endoglucosaminidase (e.g., when the endoglucosaminidase remains in the cell), or before the contact with the endoglucosaminidase (e.g., when both are secreted). Secretion signals will in general be similar for both glycoproteins and endoglucosaminidases (or optionally also glycosyltransferases), if the latter are secreted. The nature of the secretion signal will indeed typically not depend on the protein to be secreted, but on the type of eukaryotic cells used. As long as the secretion signal is functional in the cell type in which it is used (i.e., it results in secretion to the extracellular environment of the protein or peptide to which it is fused), this feature is not critical to the invention. Thus, secretion signals from other organisms may be used, as long as these signals lead to secretion in the eukaryotic cells used. Secretion signals are well known in the art and may be derived from—typically the N-terminus of—proteins that are secreted, or may be made synthetically (e.g., Tan et al., *Protein Engineering* 2002, vol. 15, no. 4, pp. 337-345). Alternatively, they can be derived from genomic sequences using computational methods (Klee et al., *BMC Bioinformatics* 2005, 6:256). Also, bacterial secretion signals can be used. Further examples of signal peptides that can be used are described in WO2002/048187 (eukaryotic cells), Schaaf et al. (*BMC Biotechnol.* 2005; 5:30) (moss cells), EP549062. Specific secretion signals used in yeast include, e.g., α-factor secretory peptide, the PH05 secretory peptide, and the BAR1 secretion signal.

Although secretion is particularly envisaged for easy recovery of glycoproteins, alternative options exist. The produced glycoproteins may, for instance, be deposited in inclusion bodies in the cell, or in membrane-bound organelles or in structures with similar functions. When cells are part of an organism that is used for production (e.g., a plant instead of a plant cell culture), the glycoprotein may be produced in or transported to specific organs or tissues of the organism from which it can be recovered (e.g., glands or trichomes). It should be noted that, particularly in cases where the protein is not secreted, it is possible that the protein is deposited in an inactive form. Thus, additional refolding or re-activating steps may be needed in order to obtain a physiologically relevant form of the glycoprotein.

Although, in addition to the glycoprotein, the endoglucosaminidase may also be secreted by the cell (using identical or similar secretion signals—i.e., the remarks on secretion signals for glycoproteins also apply for endoglucosaminidases), it can be a particular advantage that the endoglucosaminidase remains in the cell. This takes away the need for separation of the endoglucosaminidase and the glycoprotein, which arises when both proteins are secreted. Most particularly, the endoglucosaminidase not only remains in the cell, but is also fully active. Its activity should be regulated spatiotemporally in order to ensure that the desired hydrolysis takes place. To this end, the endoglucosaminidase may be operably linked to an ER or Golgi localization signal. Such signal directs the endoglucosaminidase to the ER or Golgi, respectively, where it is retained. As the ER and Golgi apparatus are the intracellular locations where glycosylation of proteins takes place, targeting to these organelles ensures that the endoglucosaminidase is in the correct intracellular position to modify the glycosylation of the glycoprotein.

This is particularly also true for the glyco-engineered yeast cells described herein, as the at least one enzyme needed for complex glycosylation is also targeted to function in the ER→Golgi secretory pathway, the endoglucosaminidase can be targeted in such a way that these enzymes act cooperatively on the glycoprotein.

Indeed, in yeast—as in humans—the luminal surface of the ER and Golgi apparatus provides catalytic surfaces that allow the sequential processing of glycoproteins as they proceed from the ER through the Golgi network into the medium. As a glycoprotein proceeds from the ER through the secretory pathway, it is sequentially exposed to different mannosidases and glycosyltransferases. Several processing steps rely on previous reactions because some N-glycosylation enzymes depend on a particular substrate that is created by the previous enzyme. N-glycosylation enzymes, in particular, exogenous enzymes such as the endoglucosaminidase and the at least one enzyme needed for complex glycosylation, must therefore, be arranged in a predetermined sequence to allow for the synthesis of specific N-glycan structures.

Establishing the sequential processing environments of the secretory pathway requires the proper localization of N-glycosylation enzymes. The mechanisms by which secreted proteins can be transported through the secretory pathway (from the ER to the cis-, medial- and trans-Golgi compartments and into the medium), while each compartment maintains a specific set of resident (for example, N-glycosylation) enzymes, has been the subject of extensive study. Two well-established mechanisms that localize proteins to the various compartments of the secretory pathway are retrieval and retention (van Vliet et al., *PBMB* 1 2003; Teasdale et al., 27 1996).

Retrieval is a process by which proteins are localized to certain organelles through interaction with other proteins. Several ER-residing proteins contain a carboxy-terminal tetrapeptide with the consensus sequence KDEL (SEQ ID NO:1) (or HDEL (SEQ ID NO:2) in yeast), which has been shown to be required for efficient localization to the ER.

Several ER- and Golgi-residing enzymes are type II membrane proteins. These proteins have a common domain structure comprising a short cytoplasmic tail at the amino terminus, a hydrophobic transmembrane domain, a luminal stem and a C-terminal catalytic domain. Deletion studies as well as fusions to non-Golgi-residing proteins have identified the N-terminus and, in particular, the transmembrane region, as containing the targeting information of many type II membrane proteins. Although it is clear that N-terminal domains are involved in targeting, the extent to which their targeting ability is transferable between different species is not yet totally clear. Nevertheless, considerable advances have been made, such as the design of genetic libraries of known type II membrane protein domains that encode peptides that are associated with proteins that naturally localize to the ER and Golgi of *S. cerevisiae* or *P. pastoris* (Choi et al., 5022 2003; Hamilton et al., *Science* 1244) confirming the suitability of, e.g., the leader sequence from *S. cerevisiae* Sec12 (ER localization), MNN2 (Golgi localization), and MNN9 (Golgi localization). Sequences listed in table 5 of WO02/000879 include HDEL and the leader sequences from MnsI for ER localization, and leader sequences from Och1 and Mnt1 (Golgi-cis localization), from Mnn2 (Golgi medial localization), from Mnn1 (Golgi trans localization), from alpha-2,6-sialyltransferase (trans-Golgi network) and from beta-1,4-galactosyltransferase I (Golgi localization).

Localization signals thus are well known in the art and may be derived from proteins that are normally localized in the ER or Golgi for their function. Moreover, localization sequences from one organism may function in other organisms. For example, the membrane-spanning region of α-2,6-sialyltransferase from rats, an enzyme known to localize in the rat trans Golgi, was shown to also localize a reporter gene (invertase) in the yeast Golgi (Schwientek, et al., 1995). Schwientek and co-workers have also shown that fusing 28 amino acids of a yeast mannosyltransferase (Mnt1), a region containing an N-terminal cytoplasmic tail, a transmembrane region and eight amino acids of the stem region, to the catalytic domain of human GalT are sufficient for Golgi localization of an active GalT (Schwientek et al. 1995 *J. Biol. Chem.* 270 (10):5483-5489). Other well-documented motifs are the KDEL and HDEL motif for retention in the ER. According to particular embodiments, the ER or Golgi localization signal is from a protein that is itself localized in the ER or Golgi when functionally active. Examples of such proteins include, but are not limited to, *S. cerevisiae* dipeptidyl aminopeptidase A (Ste13p), human β-galactoside-α-2,6-sialyltransferase (ST6GalI) and the human ganglioside-$GM_2$-synthase. According to further embodiments, the localization sequence is derived from one of the following proteins: Ste13p, GL2-synthase, ganglioside-$GM_2$-synthase, and α-2,6-glycosyltransferase, in particular α-2,6-sialyltransferase, most particularly, β-galactoside-α-2,6-sialyltransferase.

Importantly, the Golgi apparatus is not just one homogeneous region, but has five functional regions: the cis-Golgi network, cis-Golgi, medial-Golgi, trans-Golgi, and trans-Golgi network. Vesicles from the endoplasmic reticulum (via the vesicular-tubular cluster) fuse with the cis-Golgi network and subsequently progress through the stack of cisternae that make up the Golgi apparatus to the trans-Golgi network, where they are packaged and sent to the required destination. Each region contains different enzymes that selectively modify the contents, e.g., depending on where they are destined to reside. Thus, depending on the exact targeting of the endoglucosaminidase within cells, glycosylation pathways may be modified in different ways.

For instance, the endoglucosaminidase may be targeted late in the Golgi, after sugar structures have already been added to the glycoprotein. This may, for instance, be particularly envisaged as a kind of "proofreading" or "in vivo clean-up," i.e., in situations where the desired complex glycosylation pattern is produced on the glycoproteins as well as hybrid type and/or high mannose structures (a situation often observed in yeasts modified for human-type glycosylation). There, a late-Golgi targeting of an endoglucosaminidase specific for hybrid-type and high-mannose glycosylation structures (e.g., EndoT, EndoH) ensures that the aberrantly glycosylated glycoproteins are deglycosylated (particularly to a single GlcNAc), while the glycoproteins with complex glycosylation are secreted as such. Thus, two easily separable glycopopulations are obtained. An alternative option is the late targeting of an endoglucosaminidase that hydrolyzes all glycosylation structures made in the cell (which notably need not be endoglucosaminidases with broad specificity, as some eukaryotic cells have only a limited glycodiversity, or as the eukaryotic cells may be modified to produce glycoproteins with limited glycodiversity, e.g., by deficiency of an enzymatic activity needed for complex glycosylation). This way, a uniform glycosylation pattern may be obtained in the population of glycoproteins, e.g., only non-glycosylated or only single monosaccharide-modified glycoproteins. Another option would be to target the endoglucosaminidases to an earlier stage in the ER→Golgi glycosylation pathway, while a glycosyltransferase (e.g., an additional exogenous glycosyltransferase that is targeted to later in the pathway) is active further downstream. This way, a uniform glycopopulation (e.g., of single GlcNAc-modified glycoproteins) is presented as substrate to the glycosyltransferases. This results in a uniform population of glycosylated glycoproteins. Note that this uniform glycopopulation may particularly be a uniform population of non-naturally occurring glycoforms, as typical endoglucosaminidases will also remove the inner $Man_3GlcNAc_2$ core structure typical of natural glycostructures. However, such structures are often less immunogenic in mammals than particular glycans produced in plant, yeast or insect cells.

It will be clear that statements made here on the targeting of endoglucosaminidases, of course, also apply to the targeting of other enzymes within the cell, in particular, to glycosyltransferases and/or to the at least one enzyme needed for complex glycosylation used in particular embodiments. Indeed, as these enzymes are active in the ER→Golgi pathway and act sequentially, these enzymes should be carefully targeted. According to particular embodiments, the at least one enzyme needed for complex glycosylation is more than one enzyme. More particularly, the at least one enzyme is the number of enzymes needed to form a pathway for complex glycosylation. Most particularly, each of these enzymes needed for complex glycosylation is targeted so that they act sequentially and in the right order (typically, one enzyme will modify the sugar chain to a substrate for the next enzyme). According to a particular embodiment, the at least one enzyme needed for complex glycosylation is at least one N-acetylglucosaminyl transferase (e.g., GnT I, GnT II, GnT III, GnT IV, GnT V, GnT VI), at least one mannosidase (in particular mannosidase II), at least one fucosyltransferase, at least one galactosyltransferase, at least one sialyltransferase, or any combination of these enzymes.

Examples of glyco-engineered yeasts wherein complex glycosylation pathways have been engineered are extensively described in the art (see, e.g., Choi et al., 5022 2003; Hamilton et al.; Science 1244; Wildt et al., 119 2005; Hamilton et al., 387 2007; EP1211310; WO02/000879; US2006148039). Note that the enzyme(s) needed for complex glycosylation is/are all targeted to compartments of the secretory ER→Golgi pathway and, thus, are not secreted.

In addition, a number of other genes may also be transformed in the glyco-engineered yeast cells described herein to ensure optimal production of complex-type glycosylated glycoproteins, such as ER and Golgi-specific transporters (e.g., sym- and antiport transporters for UDP-galactose and other precursors), or enzymes involved in the synthesis of activated oligosaccharide precursors such as UDP-galactose and CMP-N-acetylneuraminic acid. Indeed, the contacting with the at least one enzyme needed for complex glycosylation may occur in the presence of specific glycosyl donors (e.g., sugar nucleotide donors) to ensure efficient and correct glycosylation.

The glycosylation status of the produced glycoprotein will depend both on the cellular system used (e.g., which enzymes are present therein) and the specificity of the endoglucosaminidase. Moreover, the time and place where these enzymes act is also important (e.g., which enzyme acts first in the ER→Golgi pathway). Thus, it is possible that cells will express solely non-glycosylated proteins, or proteins having only single GlcNAc residues (e.g., in the case of yeast cells and an endoglucosaminidase capable of hydrolyzing high-mannose and hybrid type glycans). These proteins can serve as the basis for, e.g., crystallization studies. Another possibility is that such proteins are further modified, e.g., by treatment with glycosyltransferases, resulting in proteins with the desired glycan moieties.

Alternatively, cells can be used capable of achieving the desired (typically complex) glycosylation (e.g., glyco-engineered yeast wherein the endoglucosaminidase acts after the enzymes needed for complex glycosylation (either intracellularly, e.g., in the trans Golgi or trans-Golgi network, or extracellularly)). A prerequisite in this scenario is that the endoglucosaminidase does not hydrolyze the desired sugar chains (e.g., because of its specificity, because the endoglucosaminidase is spatially and/or temporally separated from the glycosylated protein, or because the endoglucosaminidase is rendered inactive after it has removed undesired glycans). Typically, such cells will produce two populations of glycoproteins: the correctly glycosylated form and a non-glycosylated or single GlcNAc-modified form (obtained, e.g., from deglycosylation of glycoproteins with hybrid-type or mannose-type glycan modifications). Although such mixed population still requires a separation step before a uniformly glycosylated population is obtained, this separation step is much easier than with traditional production methods, as the (e.g., weight, hydrodynamic properties) difference between proteins with complex glycosylation and non-glycosylated proteins is much larger than between differently glycosylated proteins.

Alternatively, it can be envisaged that the cells produce and/or secrete only correctly glycosylated proteins. For, e.g., glyco-engineered yeast, this can be achieved by targeting the endoglucosaminidase enzyme just before the at least one enzyme for complex glycosylation in the ER→Golgi pathway, in such a way that all glycoproteins are first (at least partly) deglycosylated by the endoglucosaminidase, after which they are modified by the at least one enzyme for complex glycosylation. Using the latter approach, the produced glycoproteins may have non-naturally occurring carbohydrate chains, as the endoglucosaminidase typically will remove the core $Man_5GlcNAc_2$ structure, or at least part thereof, so that the sugar chain added on the glycoprotein by the enzymes for complex glycosylation will be added on shortened base structures, such as a single GlcNAc residue. Although not naturally occurring, such complex sugar chains often also are non-immunogenic and may have other desirable properties, such as, e.g., increased stability, longer half-life, etc. Always important, but particularly in the generation of such new, synthetic pathways, is that the glycoprotein after modification by a first enzyme (e.g., an endoglucosaminidase) is a suitable substrate for the next enzyme (e.g., an enzyme needed for complex glycosylation).

However, it is understood that further (complex) glycosylation may also be inhibited, e.g., in order to retain solely non-glycosylated proteins or single-monosaccharide-modified proteins. Thus, according to a particular embodiment, the eukaryotic cells described herein do not comprise at least one enzyme needed for complex glycosylation, such as ER-mannosidase I, glucosidase I, glucosidase II, galactosyltransferase, sialyltransferase, mannosidase II, N-acetylglucosaminyl transferase I, and N-acetylglucosaminyl transferase II. Such cells are not capable of complex glycosylation of glycoproteins. Nevertheless, even though (complete) complex glycosylation is normally not achieved in such cells, it may be possible to target an endoglucosaminidase with a particular specificity to a place in the ER→Golgi glycosylation pathway where it ensures that the glycoprotein after it has been contacted with the endoglucosaminidase is again a target for the following enzymes. This way, new synthetic pathways may be generated. It may, for instance, be possible in a cell that lacks N-acetylglucosaminyl transferase I to target an endoglucosaminidase just before the galactosyltransferase and sialyltransferase. This way, only the galactosyltransferase and sialyltransferase will act on the (partially) deglycosylated protein (e.g., a single-GlcNAc-modified protein), thus yielding a protein with non-naturally occurring complex glycosylation.

Whereas cells for the production of glycoproteins as described herein will typically be provided in the form of a cell culture, this need not necessarily be the case. Indeed, the cells producing the glycoproteins may be part of an organism, e.g., a transgenic animal or plant. According to a particular embodiment, plants comprising the glycoprotein and endoglucosaminidase-containing cells as described in the application are also envisaged. Typically, plants will have multiple of these cells, particularly also in different organs and/or tissues.

The eukaryotic cells described herein are particularly well suited for glycoprotein production. According to particular embodiments, the glycoproteins are enriched for a specific glycoform, particularly single GlcNAc-modified glycoproteins. Thus, methods are provided for producing glycoproteins modified with a single GlcNac moiety in a eukaryotic cell, comprising the steps of:
  providing a eukaryotic cell comprising a first exogenous nucleic acid sequence encoding an endoglucosaminidase enzyme and a second exogenous nucleic acid sequence encoding a glycoprotein in conditions suitable for expressing the endoglucosaminidase enzyme and the glycoprotein; and
  recovering the glycoprotein after it has been intracellularly or extracellularly contacted with the endoglucosaminidase.

Although the glycoproteins with a single GlcNAc residue may be the only glycoform of the glycoprotein produced by the cell (i.e., a uniform glycopopulation is produced), the methods may also be used to enrich single GlcNAc-modified proteins in a mixed population, or rather, to remove the glycoproteins with undesired glycosylation patterns by converting them to single GlcNAc-modified proteins. Since single GlcNAc-modified proteins are both easier to separate from a mixed glycopopulation as an easier starting point for further transglycosylation reaction, this is a considerable advantage. So even though several glycoforms of the glycoprotein may be produced, these typically can be easily separated (e.g., proteins with complex glycosylation as well as proteins with single GlcNAc residues). According to particular embodiments, the eukaryotic cells used in the methods described herein are not capable of complex glycosylation of glycoproteins, or at least not of naturally occurring complex glycosylation of glycoproteins (i.e., with the inner $Man_3GlcNAc_2$ core).

The methods as described herein may be further adapted to ensure that the contact between glycoprotein and endoglucosaminidase occurs under optimal circumstances (i.e., to ensure optimal activity of the endoglucosaminidase on the glycoprotein). For instance, when the contact occurs intracellularly, the endoglucosaminidase may be targeted to the (desired place in the) Golgi or ER where it exerts its function on the glycoprotein. Depending on, e.g., further transglycosylation envisaged in or outside the cell, the desired place may vary, as described above. According to particular embodiments, the intracellular contact occurs in the Golgi or ER.

Both the endoglucosaminidase and the glycoprotein may also be secreted and the contact may happen extracellularly. Depending on the cells and endoglucosaminidase that are used, however, the optimal growth and production conditions for the cells (e.g., pH, temperature) may differ from the optimal conditions for enzymatic activity. Thus, the medium where the extracellular contact between the glycoprotein and the endoglucosaminidase takes place may be adjusted for optimal enzymatic activity of the endoglucosaminidase. According to a particular embodiment, the conditions of the medium wherein the extracellular contact takes place are adjusted for optimal enzymatic endoglucosaminidase activity. According to a further particular embodiment, the pH of the medium wherein the extracellular contact takes place is adjusted for optimal enzymatic endoglucosaminidase activity. Typically, this may be done by a pH shift of the medium after the cells have been allowed to produce and secrete both glycoproteins and endoglucosaminidases. In general, such pH shift will be a downshift, as endoglucosaminidases usually are physiologically active in an acidic environment. According to another particular embodiment, the temperature of the medium is adjusted for optimal enzymatic activity. Note that the adjustment of growth and production conditions may be done just before endoglucosaminidase activity, or that the conditions may already been adapted during cell growth. For instance, Pichia cells can grow and produce proteins in a fairly acidic medium, which thus is already adjusted for optimal activity of particular endoglucosaminidases. However, as some eukaryotic cells are dependent on N-glycosylation for their integrity, it might be beneficial to buffer the pH of the growth medium to a pH at which the endoglucosaminidase is not active, and downshift the pH only after the protein production is finished.

According to a particular aspect, the protein modified with the single GlcNAc residue is only an intermediary product. Methods according to this aspect will include at least one additional transglycosylation step, which can occur both extracellularly (via an added enzyme, or via an enzyme also produced by the cells) or intracellularly. According to these embodiments, before the final recovery of the glycoprotein, the methods further involve a step of contacting the enzyme with a glycosyltransferase after it has been intracellularly or extracellularly contacted with the endoglucosaminidase. Optionally, this contacting with a glycosyltransferase may occur in the presence of (potentially extra added) specific glycosyl donors (e.g., sugar nucleotide donors) to ensure efficient and correct glycosylation. This will especially be the case when the transglycosylation takes place extracellularly.

If the transglycosylation step takes place intracellularly, it will be understood by the skilled person that, when both the endoglucosaminidase enzyme and the glycosyltransferase enzyme are targeted to the ER or Golgi, it is ensured that the glycosyltransferase activity occurs after the endoglucosaminidase activity. Typically, this may be ensured by targeting both enzymes to different compartments of the ER or Golgi, as there is a fixed order in which proteins follow the ER→Golgi route. In the event both enzymes are targeted to the same compartment, or that both activities are performed by the same enzyme, it typically will be ensured that the protein after the transglycosylation step is no longer recognized as substrate for the endoglucosaminidase enzyme. Thus, separation of the enzymatic activities in time may also involve spatial separation and/or a different substrate specificity and/or inactivation of the enzyme. According to a particular embodiment, both the endoglucosaminidase and the glycosyltransferase are produced by the same cell, but only the glycosyltransferase is secreted, to ensure transglycosylation takes place after the endoglucosaminidase activity.

Depending on how the method is performed, the glycosyltransferase enzyme may be added extracellularly (i.e., is not produced by the same cells), is also produced and secreted by the cells producing the glycoprotein and endoglucosaminidase, or is also produced by the cells and retained within the ER or Golgi apparatus. The glycosyltransferase may be encoded by an exogenous sequence, or may be an enzyme that is endogenous in the cells having a first exogenous nucleic acid sequence encoding an endoglucosaminidase enzyme and a second exogenous nucleic acid sequence encoding a glycoprotein.

According to particular embodiments using glyco-engineered yeast as described herein, the glycoproteins are enriched for a specific (complex-type) glycoform, while proteins with high-mannose type and hybrid-type glycosylation are depleted by hydrolyzing the glycans to simpler forms (e.g., a single GlcNAc residue). Thus, methods are provided for producing glycoproteins in a glyco-engineered yeast cell while depleting proteins with high mannose-type glycosylation and/or hybrid-type glycosylation, comprising the steps of:
  providing a glyco-engineered yeast cell comprising a first exogenous nucleic acid sequence encoding an endoglucosaminidase enzyme, a second exogenous nucleic acid sequence encoding a glycoprotein, and at least a third exogenous nucleic acid sequence encoding at least one enzyme needed for complex glycosylation, selected from the group consisting of N-acetylglucosaminyl transferase I, N-acetylglucosaminyl transferase II, mannosidase II, galactosyltransferase, and sialyltransferase, in conditions allowing expression of the at least three nucleic acid sequences; and
  recovering the glycoprotein after it has been intracellularly contacted with the at least one enzyme needed for complex glycosylation and intracellularly or extracellularly contacted with the endoglucosaminidase.

"Contacted" as used herein does not only refer to physical proximity, but specifically implies that the enzyme with which the glycoprotein is contacted has the opportunity to exert its enzymatic function on the glycoprotein. Thus, physical proximity to an inactive, temporally inactive or inactivated enzyme does not constitute "contact" as defined herein—this requires contact with an active enzyme in both a conformation (i.e., spatial orientation and distance between the proteins) and time-frame that are sufficient for enzymatic activity.

Depleting proteins with high mannose-type glycosylation and/or hybrid-type glycosylation in yeast cells (by selectively converting these glycoforms to, e.g., single GlcNAc-modified proteins) may result in yeast cells producing glycoproteins as a uniform and homogeneous, typically complex, glycopopulation. Alternatively, several glycoforms of the glycoprotein may be produced, but these typically can be easily separated as no glycoproteins with sugar chains of comparable size to the complex glycans are produced. An example of mixed glycoforms that are produced are proteins with complex glycosylation as well as proteins with single GlcNAc residues. The single GlcNAc-modified proteins themselves can be used, e.g., as starting point for further transglycosylation reactions, to result in proteins with complex glycosylation, or can be used as such in crystallization studies.

The methods as described herein may be further adapted to ensure that the contact between glycoprotein and endoglucosaminidase occurs under optimal circumstances (i.e., to ensure optimal activity of the endoglucosaminidase on the glycoprotein). For instance, when the contact occurs intracellularly, the endoglucosaminidase may be targeted to the (desired place in the) Golgi or ER where it exerts its function on the glycoprotein. The same, of course, applies for the contact between the glycoprotein and the at least one enzyme for complex glycosylation. Depending on the specific order envisaged (in particular, whether the endoglucosaminidase is contacted with the glycoprotein before or after the contact with the enzyme(s) needed for complex glycosylation), the desired place within the ER or Golgi (e.g., cis-Golgi network, cis-Golgi, medial-Golgi, trans-Golgi, and trans-Golgi network) may vary, as described above. According to particular embodiments, the intracellular contact with the at least one enzyme needed for complex glycosylation occurs in the Golgi or ER. According to particular embodiments, the intracellular contact with the endoglucosaminidase occurs in the Golgi or ER. According to further particular embodiments, the glycoprotein is contacted with the endoglucosaminidase before it is contacted with the at least one enzyme needed for complex glycosylation in the ER→Golgi secretory pathway. According to alternative further particular embodiments, the contact between glycoprotein and endoglucosaminidase occurs in the ER or Golgi, but after the contact with the at least one enzyme needed for complex glycosylation. According to yet further particular embodiments, the respective targeting signals of the endoglucosaminidase and the enzyme needed for complex glycosylation are chosen in such a way that the enzymes are targeted to different functional regions (ER, cis-Golgi network, cis-Golgi, medial-Golgi, trans-Golgi, and trans-Golgi network) so that they act sequentially. According to still further particular embodiments, the enzymes are targeted in such a way that they act immediately after each other, e.g., they may be targeted to adjacent compartments in the Golgi apparatus.

Unlike the at least one enzyme needed for complex glycosylation, the endoglucosaminidase may also be secreted. This may be the case when the glycoprotein is also secreted and the contact between glycoprotein and endoglucosaminidase happens extracellularly (after the intracellular contact with the at least one enzyme needed for complex glycosylation). Depending on the cells and endoglucosaminidase that are used, however, the optimal growth, production and secretion conditions for the cells (e.g., pH, temperature) may differ from the optimal conditions for enzymatic activity. Typically, the culturing of yeast cells happens at more or less neutral pH (i.e., around pH 7), while the pH optimum of several glycosidases is acidic (typical examples include enzymes with optimum around pH 5 or a pH optimum of about 6). Thus, the medium where the extracellular contact between the glycoprotein and the endoglucosaminidase takes place may be adjusted for optimal enzymatic activity of the endoglucosaminidase. According to a particular embodiment, the conditions of the medium wherein the extracellular contact takes place are adjusted for optimal enzymatic endoglucosaminidase activity. According to a further particular embodiment, the pH of the medium wherein the extracellular contact takes place is adjusted for optimal enzymatic endoglucosaminidase activity. Typically, this may be done by a pH shift of the medium after the cells have been allowed to produce and secrete both glycoproteins and endoglucosaminidases. In general, such pH shift will be a downshift, as endoglucosaminidases usually are physiologically active in an acidic environment. According to particular embodiments, the culturing of the yeast cells and production and secretion of the glycoprotein occur at a more or less neutral pH, in particular between pH 6 and 8, more in particular between pH 6.5 and pH 7.5, even more in particular between pH 6.7 and 7.3, most in particular at pH 7. According to specific embodiments, the extracellular contact between glycoprotein and endoglucosaminidase occurs at a pH of between 4 and 6, more in particular between pH 4.5 and pH 5.5, even more in particular between pH 4.7 and pH 5.3, most in particular at pH 5. According to an alternative embodiment, the contacting occurs between pH 4 and 5, pH 4.5 and 5 or between pH 4.7 and 5.

According to a specific combination of embodiments, the pH of the medium is adjusted after the growth and production/secretion phase to provide optimal conditions for the endoglucosaminidase. According to particular embodiments, the pH is downshifted. According to further particular embodiments, the pH shift is at least 0.5 units, at least 1 unit, at least 1.5 units or at least 2 units. According to specific embodiments, the pH is shifted from between pH 6 and 8 for growing conditions between pH 4 and 6 for the contacting with the enzyme and enzymatic activity. According to alternative embodiments, however, cells are grown in conditions that are permissive for both growth/production and enzymatic activity. For instance, the yeast *Pichia pastoris* is able to grow and produce proteins at lower pH (e.g., pH 5), which is the pH optimum for enzymes such as endoH or, in particular, endoT. Similarly, if yeast cells are chosen that have limiting conditions for optimal growth, it is possible to choose an endoglucosaminidase enzyme with a broad optimum range.

According to another particular embodiment, the temperature of the medium is adjusted for optimal enzymatic activity. Note that the adjustment of growth and production conditions may be done just before endoglucosaminidase activity, or that the conditions may already been adapted during cell growth. As already mentioned, *Pichia* cells can grow and produce proteins in a fairly acidic medium, which, thus, is already adjusted for optimal activity of particular endoglucosaminidases.

It is to be understood that although particular embodiments, specific configurations as well as materials and/or molecules, have been discussed herein for cells and methods according to the disclosure, various changes or modifications in form and detail may be made without departing from the scope and spirit of the disclosure. The following examples are provided to better illustrate particular embodiments, and they should not be considered limiting the application. The application is limited only by the claims.

EXAMPLES

Example 1

Intracellular and Soluble Expression of a *Trichoderma reesei* endo-N-acetyl-β-D-glucosaminidase (EndoT)) in *Pichia pastoris*

Introduction and Strategy

Saprophytic filamentous fungi produce and secrete a variety of hydrolases needed for the degradation of organic material. In particular, organisms secreting cellulases and hemicellulases are of great interest to the biotechnological industry and can be used in degradation of biomass for, e.g., bio-fuel production. One of the best producers of such enzymes is *Trichoderma reesei*.

It was shown previously that the glycosylation pattern on *T. reesei* secreted proteins varies considerably depending on the environmental conditions. Many of the differences in glycosylation are attributable to post-secretory trimming events by extracellular hydrolases, either becoming post-translationally activated or being differentially regulated on transcription level because of the applied growth conditions. Very peculiar in this sense, is the presence of only a single GlcNAc-residue onto the Asn of known N-glycosylation sites. However, recent findings clearly indicate that this is the result of an endo-N-acetylglucosaminidase-like activity, here called EndoT, which has now been successfully purified from the *T. reesei* growth medium (see, WO2006/050584).

Enzymes acting on the chitobiose part of N-linked glycans, like endo-N-acetyl-β-D-glucosaminidases (e.g., EndoH) and N-linked-glycopeptide-(N-acetyl-beta-D-glucosaminyl)-L-asparagine amidohydrolases (e.g., PNGase F) are important tools in the isolation and analysis of oligosaccharides from glycoproteins. Moreover, glycosidases that are able to deploy deglycosylation activities on a native protein (such as EndoH) have proven to be invaluable for the elucidation of the crystal structure from several glycoproteins. Purified *T. reesei* EndoT was proven to be able to act upon high-mannose and hybrid, but not on complex N-glycans from native proteins.

Based on internal peptide sequence information, the gene encoding EndoT could be deduced in silico. However, when comparing results from N- and C-terminal sequence analysis, SDS-PAGE and iso-electric focusing on the one hand and in silico ORF translation, and following MW/pI calculations on the other hand, it was clear that—apart from the cleavage of a predicted 17 amino acid signal peptide—further proteolysis occurs at both the N- and C-terminus of the protein. At the time it was not known whether this happens intracellularly and/or extracellularly, and whether these proteolytic steps are important for protein maturation and maximal enzyme activity.

Therefore, soluble expression of several forms of processed EndoT, i.e., the mature protein (EndoT[FullSize]), the mature protein missing nine extra N-terminal amino acids (EndoT[-Nterm]), the mature protein missing 43 C-terminal amino acids (EndoT[-Cterm]) and the mature protein missing both the N- and C-terminal amino acids (EndoT[-N/Cterm])—was established in the methylotrophic yeast *Pichia pastoris*. The four forms were purified from the medium and their specific activity was determined. Moreover, the EndoT activity was also locally expressed in the late compartments of the *Pichia* secretion pathway by fusing EndoT[FullSize] to the localization signal of *S. cerevisiae* dipeptidyl aminopeptidase A (Ste13p), a protein known to reside within the yeast trans-Golgi network (Nothwehr et al., 1993). With this, we envisage the clean-up of non-complex N-glycans produced within a glyco-engineered expression strain of *Pichia pastoris*, before secretion of the recombinant glycoproteins into the cultivation broth.

Materials and Methods:

Strains and Growth Conditions

Plasmid construction and propagation was performed using chemocompetent *Escherichia coli* MC1061 cells (hsdR2 hsdM$^+$ hsdS$^+$ araD139 Δ(ara leu)$_{7697}$Δlac$_{X74}$ galE15 galK16 rpsL (St$^r$r) mcrA mcrB1) (Casadaban and Cohen, 1980). Growth and transformation of *E. coli* was done via standard procedures (Sambrook et al., 1989).

The following *Pichia* strains were used during the experimental set-up: GS115 (his4) (Invitrogen), GS115-Man5 (his4) and GS115-hIFNβ (HIS4). GS115-Man5 is a derivative of GS115, transformed with pGlycoSwitch-M5 and mainly synthesizing Man$_5$GlcNAc$_2$ N-glycans on its secreted proteins (Vervecken et al., 2004; Vervecken et al., 2007). GS115-hIFNβ (HIS4) is a derivative of GS115, transformed with pPIC9hIFNβ and secreting human interferon beta (hIFNβ). For protein production purposes, yeast strains were pregrown in BMGY medium (1% yeast extract, 2% peptone, 1% glycerol, 1.34% yeast nitrogen base w/o amino acids and 100 mM potassium phosphate pH 6.0) for 48 hours at 30° C. and 250 rpm while protein expression was induced after transfer of the cells into BMMY (1% yeast extract, 2% peptone, 1% methanol, 1.34% yeast nitrogen base w/o amino acids and 100 mM potassium phosphate pH 6.0) and further cultivation at 30° C. and 250 rpm.

The *S. cerevisiae* strain INVSc1 (α, leu2-3, 112 his3Δ1, trp1-289, ura3-52) (Invitrogen) was used to prepare genomic DNA as a template for the amplification of specific STE13 gene fragments (see, below). General maintenance of strain INVSc1 as well as the different *Pichia* strains and transformants was done on YPD (1% yeast extract, 2% pepton, 2% dextrose).

Plasmid Construction

A custom-made, codon-optimized synthetic gene was ordered at GeneArt AG (Regensburg, Germany) for the expression of mature EndoT in *Pichia pastoris*. At the 5' site, an EcoRI restriction site followed by the sequence CTC GAG AAA AGA GAG GCT GAA GCG (SEQ ID NO:3)—encoding the C-terminal part of the *S. cerevisiae* alpha-mating factor pro-region and the Kex2p cleavage site (Leu-Val-Lys-Arg-Glu-Ala-Glu-Ala) (SEQ ID NO:4)—were introduced for easy downstream cloning purposes. A few exceptions to the optimal *Pichia* codon usage were requested for the introduction of specific unique restriction sites: Ala8-Val9-Pro10 (counting starts from the first codon of the alpha-mating factor pro-region part (CTC encoding Leu)) is encoded by GCGGTACCC for the introduction of a KpnI site (underlined); Leu14-Gln15 is encoded by CTG CAG for the introduction of a PstI site; Pro24-Arg25 is encoded by CCT AGG for the introduction of an AvrII site; Glu307-Leu308 is encoded by GAG CTC for the introduction of an Ecl136II site and Arg339-Pro340 is encoded by AGG CCT for the introduction of a StuI site. The last codon of the mature EndoT (GCT encoding Ala350) is followed by the sequence TAA C*CCTAAGGT* AAGCTT (SEQ ID NO:5), containing two stop codons (in italics) and the unique restriction sites Bsu36I respectively HindIII (underlined). The synthetic gene was provided as an AscI/PacI fragment within the pGA18 vector backbone. From there, it was transferred as an EcoRI/HindIII fragment into pUC19, digested with the same enzymes, to result into pUC19EndoT [FullSize]. Vector pUC19EndoT[-Nterm] was generated by treating pUC19EndoT[FullSize] sequentially with KpnI, T4 polymerase and AvrII to allow the integration of a blunt/AvrII-sticky adaptor sequence consisting of the sense oligonucleotide 5'-GCCGAGCCGACGGACCTGC-3' (SEQ ID NO:6) and the antisense oligonucleotide 5'-CTAGGCAGGTCCGTCGGCTCGGC-3' (SEQ ID NO:7). Vector pUC19EndoT[-Cterm] was constructed by treating pUC19EndoT[FullSize] sequentially with Bsu36I, Klenow polymerase and Ecl136II, and closing of the corresponding vector fragment using T4 DNA ligase.

To obtain *Pichia* plasmids for the soluble expression of the different EndoT variants, the three pUC19-derived vectors were used to isolate EndoT[FullSize], EndoT[-Nterm] and EndoT[-Cterm] as a XhoI/NotI fragment. These fragments were introduced into a XhoI/NotI digested pPIC9 vector, resulting in the *Pichia* expression plasmids pPIC9EndoT[FullSize], pPIC9EndoT[-Nterm] and pPIC9EndoT[-Cterm] respectively, in which the EndoT variants are cloned in-frame with the complete prepro-region of the *S. cerevisiae* alpha-mating factor. To generate vector pPIC9EndoT[-N/Cterm], an AvrII/NotI fragment of plasmid pPIC9EndoT[-Cterm] was isolated and cloned into an AvrII/NotI opened vector fragment of pPIC9EndoT[-Nterm]. Finally, pUC19EndoT[FullSize] was used as a template to construct an expression plasmid for EndoT, containing an internal Kex2 cleavage site. First, pUC19EndoT[FullSize] was digested with Ecl136II and a phosphorylated double-stranded linker sequence encoding for Lys-Arg-Glu-Ala-Glu-Ala (SEQ ID NO:8) (5'-AAGAGAGAGGCTGAGGCC-3' (SEQ ID NO:9)) was introduced. Then, the resulting EndoT[FullSize+Kex2] sequence was isolated from the pUC19 backbone as a XhoI/NotI fragment and ligated into a XhoI/NotI opened pPIC9 template to generate pPIC9EndoT[FullSize+Kex2].

Plasmids for the intracellular expression of EndoT[FullSize] were generated by exchanging the prepro-region of the alpha mating factor for the coding sequence of the first 140 or 240 N-terminal amino acids of *S. cerevisiae* Ste13p (dipeptidyl aminopeptidase A). These sequences were PCR-amplified using genomic DNA (gDNA) from strain INVSc1 as a template. The gDNA was prepared from an overnight yeast culture, grown in YPD at 30° C. and 250 rpm, using the Nucleon Kit for extraction of yeast gDNA (GE Healthcare). Sense primer 5'-G GAATTCATGTCTGCTTCAACTCATTCG-3' (SEQ ID NO:10) (underlined: EcoRI site) and antisense primer 5'-CGGGGTACCGGTATTAGAATAACAAGTAGAAC-3' (SEQ ID NO:11) (underlined: KpnI site; in italics: codon for Pro140 of Ste13p) were used to amplify the gene fragment encoding the first 140 N-terminal Ste13p amino acids (i.e., the cytoplasmic and transmembrane regions of Ste13p), while the same sense primer and antisense primer 5'-CGG GGTACCGTAAATTCTACTCCTTCATATAGG-3' (SEQ ID NO:12) (underlined: KpnI site; in italics: codon for Thr240 of Ste13p) were used to generate a gene fragment encoding the first 240 N-terminal Ste13p amino acids (thus containing 100 extra amino acids of the luminal domain of Ste13p). The PCR reactions were performed using TaKaRa Ex Taq™ polymerase (TaKaRa Bio Inc.) at an annealing temperature of 56° C. The generated fragment were digested with KpnI and EcoRI and cloned into the EcoRI/KpnI opened plasmid pUC19EndoT[FullSize], resulting in pUC19Ste13(140Aa)EndoT[FullSize] and pUC19Ste13 (240Aa)EndoT[FullSize]. After sequencing to check for PCR errors, these vectors were cut with EcoRI and NotI to isolate the Ste13p-EndoT fusion constructs. The obtained fragments were cloned into an EcoRI/NotI digested pPICZA backbone, resulting in the plasmids pPICZSte13(140Aa) EndoT[FullSize] and pPICZSte13(240Aa)EndoT[FullSize] respectively.

*Pichia* Transformation

Plasmids pPIC9EndoT[Full Size], pPIC9EndoT[-Nterm], pPIC9EndoT[-Cterm] and pPIC9EndoT[-N/Cterm] were linearized in the HIS4 selection marker using SalI and transformed to *P. pastoris* GS115 (his4) (Invitrogen) and GS115-Man5 (his4) via electroporation (Cregg and Russell, 1998). Transformants were selected on minimal medium without histidine (2% dextrose, 0.67% yeast nitrogen base w/o amino acids, 1 M sorbitol, 0.77 g/l CSM-His (Bio101)).

Plasmids pPICZSte13(140Aa)EndoT[FullSize] and pPICZSte13(240Aa)EndoT [FullSize] were linearized in the 5'AOX1 promoter region and transformed to *P. pastoris* GS115-hIFNβ (HIS4). Transformants were selected on YPD containing 100 µg/ml of zeocin (Invitrogen).

Protein Analysis

Expression of secreted proteins was checked via standard SDS-PAGE analysis and Coomassie staining Strains were pregrown in BMGY and protein production was induced after transfer of the cells into BMMY, as indicated in the results section. Proteins were precipitated from the medium via the standard DOC/TCA procedure and the resulting protein pellet was resuspended in 2× Laemmli buffer. The protein samples were incubated for 5 minutes at 100° C. before loading on gel.

PNGaseF treatment of glycoproteins and the analysis of the deglycosylated proteins were done as follows. Proteins from the induction medium were precipitated with 2 volumes of ice-cold aceton. After incubation on ice for 20 minutes and centrifugation (14,000 rpm, 5 minutes), the supernatant was removed and the protein pellet was resuspended in 100 µl 50 mM Tris.HCl pH 8. SDS and β-mercaptoethanol were added to a final concentration of 0.5 and 1% respectively. Samples were incubated for 5 minutes at 100° C., after which G7 buffer (10× buffer, New England Biolabs), NP-40 (final concentration of 1%), complete protease inhibitor (Roche) and in-house produced PNGaseF (1000 units) were added. After overnight incubation at 37° C., proteins were precipitated via the DOC/TCA procedure, resuspended in 2× Laemmli buffer and analyzed via SDS-PAGE.

Enzymatic activity of EndoT was checked via a gel-shift analysis using SDS-PAGE. *Pichia* medium containing one of the EndoT forms is incubated at 30° C. in 50 mM NaOAc pH 5 in the presence of a glycoprotein. After different time points, the proteins in the reaction mixture were precipitated by addition of 3 volumes of ice-cold 100% ethanol and a 1-hour incubation on ice. After centrifugation (5 minutes, 14,000 rpm), the protein pellet was resuspended in 2× Laemmli buffer. The protein samples were incubated for 5 minutes at 100° C. before loading on gel. Higher mobility of the test glycoprotein serves as an indication for the deglycosylation capacity of the produced EndoT. The enzymatic activity of the soluble EndoT forms was checked using either RNaseB (Sigma), fetuin from fetal calf serum (Sigma) or in-house produced *T. reesei* α-1,2-mannosidase as test glycoproteins. Intracellular activity was checked via co-expression of EndoT in a *Pichia* strain that secretes human IFNβ or *T. reesei* α-1,2-mannosidase.

N-Glycan Analysis

N-linked oligosaccharides were analyzed via DNA sequencer-assisted (DSA) fluorophore-assisted carbohydrate electrophoresis (FACE) using an ABI 3130 capillary DNA sequencer (Laroy et al., 2006). N-glycans were obtained by incubation of the EndoT forms with a glycoprotein, as described for the enzymatic assay (see, above). After the reaction, the proteins are precipitated with 3 volumes of ice-cold 100% ethanol. The supernatant containing the N-glycans is separated from the protein pellet and evaporated. The thus-obtained dried oligosaccharides are further treated (labeling with APTS and clean-up) and analyzed as described (Laroy et al., 2006).

Results on Soluble Expression:

A *Pichia* expression construct was made for the soluble expression of the four EndoT forms. For this, the coding sequences of the EndoT forms, fused in-frame to the prepro region of the *S. cerevisiae* alpha mating factor, were placed under the transcriptional control of the methanol-inducible AOX1 promoter. The resulting plasmids were transformed to *P. pastoris* GS115 (his4) and a glyco-engineered strain (Man5 strain) (his4) mainly synthesizing Man$_5$GlcNAc$_2$ N-glycans on its secreted glycoproteins, and transformants were selected via their ability to grow on minimal medium without histidine. Expression levels of EndoT were checked after falcon cultivation of several transformants: selected single clones were grown for 48 hours on BMGY (buffered glycerol medium) to high cell density, after which protein expression was induced for 40 hours upon a transfer to BMMY (buffered medium containing methanol as sole carbon source). Proteins were DOC/TCA precipitated from 0.5 to 1 ml of the harvested growth medium, resuspended in 2× Laemmli loading buffer and analyzed via SDS-PAGE. Very strong expression was observed for EndoT[FullSize] and EndoT[-Nterm], whereas the secreted levels of the forms lacking the 43 C-terminal amino acids were significantly lower (data not shown). Expected MWs for the protein backbone are 37.4 kDa for EndoT[FullSize], 36.4 kDa for EndoT[-Nterm], 32.7 kDa for EndoT[-Cterm] and 31.7 kDa for EndoT[-N/Cterm].

The lower expression levels of the C-terminally truncated EndoT forms might be due to inefficient folding in the ER. In an attempt to improve the secretion of these EndoT forms, an expression construct was generated where a Kex2 cleavage recognition site (Lys-Arg-Glu-Ala-Glu-Ala (SEQ ID NO: 13)) was introduced after the codon for the last amino acid of the C-terminally truncated EndoT. In this way, a full-size version of the EndoT (now containing an internal Kex2 site) gets translated and folded within the ER lumen. We assume, based on the large expression of EndoT[FullSize], that this would be an efficient process. Once completely folded, truncation of EndoT can occur via Kex2 cleavage in the late Golgi compartment of the *Pichia* cells. Since truncation of EndoT by *Trichoderma reesei* proteases is a natural process, we assume that the introduced protease cleavage site will also be accessible for *Pichia* Kex2p. After introduction of the expression plasmid into *P. pastoris* GS115 (his4) and the glyco-engineered strain (Man5 strain)

(his4), transformants were selected via their ability to grow on minimal medium without histidine. Expression levels of truncated EndoT were checked after falcon cultivation of several transformants as described above. Proteins were DOC/TCA precipitated from 1 ml of the harvested growth medium and analyzed via SDS-PAGE. However, this strategy did not result in a significant increase of production of C-terminally truncated EndoT by *Pichia* (data not shown). This could indicate that the introduction of six extra amino acids might as well result into folding problems for the full-size version of the EndoT.

The enzymatic activity was initially checked for EndoT [FullSize] via an SDS-PAGE gel-shift analysis: a glycoprotein was incubated at 30° C. with *Pichia* Man5 medium containing soluble EndoT[FullSize] in a NaOAc pH 5.0 buffer and the degree of deglycosylation was checked on gel. The glycoproteins under investigation were *Pichia* secreted in-house produced *T. reesei* α-1,2-mannosidase carrying high mannose core and hyperglycosyl structures, fetuin carrying complex N-glycans and RNaseB carrying high mannose ($Man_{5-9}GlcNAc_2$) structures. Incubations were performed with increasing amounts of EndoT (1, 5 and 10 µl medium) and increasing amounts of time (1 hour, 3 hours and 20 hours).

Deglycosylation could be observed via SDS-PAGE analysis in the case of α-1,2-mannosidase and RNaseB, but not fetuin. Trimming of the mannosidase basically depends on the amount of EndoT added: treatment with 10 µl medium results in efficient deglycosylation after even 1 hour of incubation, whereas prolonged incubation with only 1 µl of medium does not increase the efficiency of N-glycan trimming. In contrast, deglycosylation of RNaseB happens more in a time-dependent rather than a concentration-dependent way. All together, the results indicate that the *Pichia* produced EndoT[FullSize] is secreted as an active protein, acting on high-mannose but not on complex N-glycan structures. Moreover, the mode of action on high-mannose N-glycans can differ, either depending on the protein substrate (RNaseB versus α-1,2-mannosidase) or the type of high-mannose N-glycans (core type versus hypermannosylation).

When expressed by *Pichia*, EndoT can deglycosylate itself. This was clearly observed when analyzing GS115 and Man5 produced EndoT[FullSize] on the same gel, with and without preceding in vitro PNGaseF treatment (data not shown). Whereas glycosylated endoT was observed when secreted from wild-type *Pichia pastoris*, different glycoforms were observed in the Man5 strain, which is the result of a partial deglycosylation event, importantly demonstrating that endoT can deglycosylate proteins co-secreted in the growth medium (in this case, other endoT protein molecules).

The activity of the other forms of EndoT (expressed by the Man5 strain) was also monitored via a gel-shift analysis on α-1,2-mannosidase. Samples were incubated overnight with *Pichia* medium in NaOAc pH 5. This showed that the truncated forms also have the potential to deglycosylate a given glycoprotein, albeit that the EndoT[-N/Cterm] protein is somewhat less effective (data not shown).

The analyses above strongly indicates that the N- and C-terminal amino acids are not necessary for (at the very least basal) deglycosylation activity. The low expression levels of the EndoT forms lacking the C-terminal amino acids, suggest that these amino acids might be important though for efficient protein folding upon translocation into the ER.

The N-glycans, liberated from RNaseB after treatment with different purified forms of EndoT, were APTS-labeled and analyzed via capillary electrophoresis. The results were compared with those obtained after RNaseB deglycosylation using EndoH and PNGaseF. The data show that $Man_{5-9}GlcNAc$ N-glycans were released from RNaseB using EndoH and the different EndoT forms, while $Man_{5-9}GlcNAc_2$ structures were obtained using PNGaseF (FIG. 1). Thus, the specificity of EndoT resembles that of EndoH.

Results on Intracellular Expression:

Two constructs, based on the localization signal of yeast Ste13p, were generated for the expression of Golgi-resident EndoT[FullSize]. In a first construct, the 140 N-terminal amino acids of Ste13p, comprising the transmembrane region and the cytosolic domain known to contain signals for Golgi-localization, were fused to the first amino acid of Endo[FullSize] (=fusion construct 1). A second construct was generated as well where the first 240 N-terminal amino acids from Ste13p, so also comprising 100 amino acids of the Ste13p luminal domain, were fused to EndoT[FullSize] (=fusion construct 2).

The coding sequences of the fusion proteins were put under the transcriptional control of the methanol-inducible *Pichia* AOX1 promoter and the resulting plasmids were transformed to *Pichia* GS115, expressing human interferon-beta (hIFNβ) or *T. reesei* α-1,2-mannosidase. Transformants were selected by their ability to grow on zeocin. Human IFNβ contains one N-glycosylation site and is produced by *Pichia pastoris* as a mixture of a glycosylated and a non-glycosylated form, which are easily distinguishable from one another on a 15% poly-acrylamide gel. For each construct, eight single clones were grown for two days in 100 ml shake flasks containing 30 ml BMGY. Once high cell densities were reached, the expression of soluble hIFNβ and intracellular EndoT was induced upon transfer to BMMY medium. Proteins from 0.5 ml medium, taken after 24 and 40 hours of induction, were DOC/TCA precipitated, resuspended into 2× Laemmli loading buffer and analyzed on SDS-PAGE.

The efficiency of intracellular EndoT processing was determined by comparing the ratio between secreted glycosylated and non-glycosylated (or single GlcNAC-modified) hIFNβ observed for the transformants on the one hand and for the untransformed hIFNβ-producing strain on the other hand (data not shown). Introduction of the fusion construct with the 240 N-terminal Ste13p amino acids (fusion construct 2) did not result in a change in the ratio of glycosylated versus non-glycosylated hIFNβ. However, the expression of the fusion construct only containing the cytoplasmic and transmembrane domain of Ste13p (fusion construct 1), did result in a change in the ratio: the amount of non-glycosylated (or single GlcNAc-modified) hIFNβ increased significantly when compared to the untransformed hIFNβ production strain.

From the gel, it is also clear that there is some clonal variation (data not shown): the least amount of glycosylated hIFNβ after 24 hours of induction was observed for clones 1, 4 and 7. Interestingly, at 48 hours of induction, the gel pattern observed for these clones indicates increased cell lysis. Indeed, too high intracellular (Golgi) expression of EndoT might result in serious cell stress due to severe deglycosylation of mannoproteins, thus weakening the cell wall. Growth of these clones in BMMY medium with 1 M of sorbitol as osmotic stabilizer, did not improve this result. These data indicate that several clones can be checked in order to have a transformant with a nice equilibrium between in vivo protein deglycosylation on the one hand and resistance to lysis on the other hand.

Figure 2:
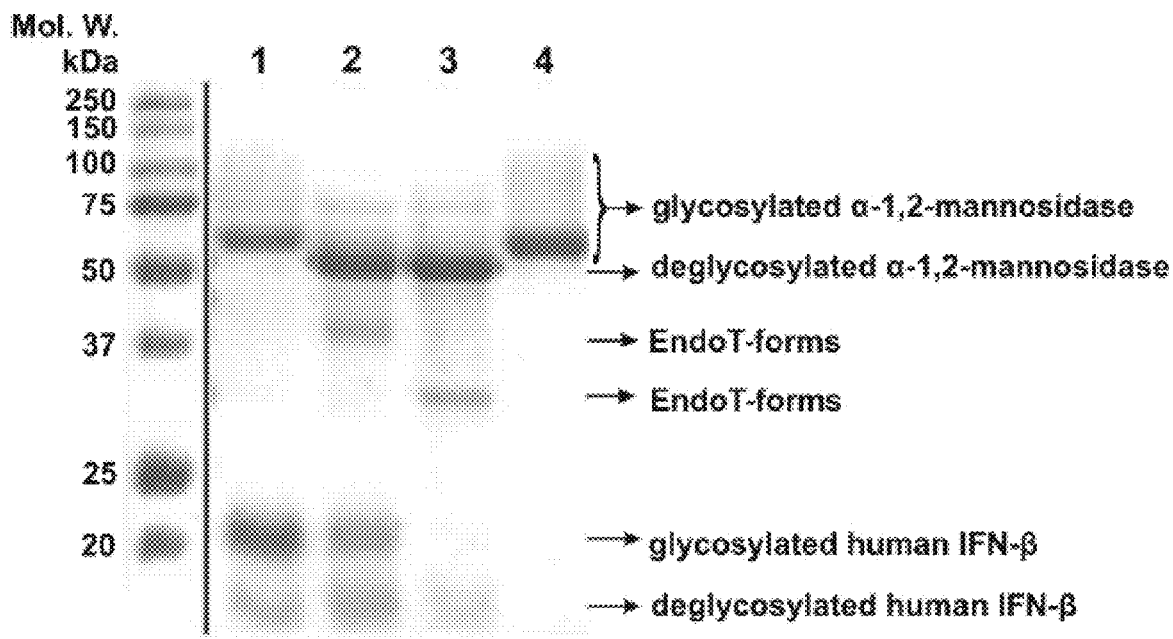
FIG. 2: Proteolytic activity of different EndoT fusion constructs. Lane 1: medium of hIFNβ strain; lane 2: medium of hIFNβ strain transformed with fusion construct 2; lane 3: medium of hIFNβ strain transformed with fusion construct 1; lane 4: no medium added.

Intracellular EndoT expression, however, also results in an extra band on gel that is not present in the untransformed strain. This could indicate that a fraction of the EndoT is released into the medium due to a proteolytic cleavage somewhere in the luminal domain, detaching it from the Ste13p localization signal. Activity of these proteolytic forms (both for fusion construct 1 and 2) was checked via a gel-shift analysis after overnight incubation of some medium in NaOAc pH 5 with hyperglycosylated α-1,2-mannosidase as a test protein. The result of this analysis is shown in FIG. 2.

In lanes 1 and 4, no deglycosylation is observed on the α-1,2-mannosidase. The gel-shift analysis, however, indicates that both proteolytic forms are active on α-1,2-mannosidase when incubated in the NaOAc buffer (whereas they only partially deglycosylate the co-expressed hIFNβ, still present in the medium that was used as EndoT enzyme source). So, although the proteolytic EndoT form derived from fusion construct 2 is active in the NaOAc buffer, no in vitro processing of hIFNβ was observed in the medium itself (less efficient conditions). This, together with the tendency of the transformants of fusion construct 1 to undergo more cell lysis, indicates that the fusion protein of EndoT with the first 140 amino acids of Ste13p is very likely acting in vivo on the soluble hIFNβ and not in vitro in a post-secretorial way. Thus, it is possible to create viable cells that produce, deglycosylate and secrete proteins in vivo.

Moreover, although the in vitro activity of the proteolytic form is low in the medium, this may primarily be due to two factors: the pH and the substrate. Indeed, the pH of the NaOAc buffer (5) is considerably lower than that of the medium (6.7). Furthermore, the assay also indicates that hIFNβ is a difficult substrate for EndoT, likely due to its compact fold and difficult accessibility of the glycans.

A subsequent test indeed indicated that EndoT is as efficient as EndoH in deglycosylating α-1,2-mannosidase in vitro. The deglycosylation capacity of fusion construct 1 was also checked in a *Pichia* strain expressing the soluble *T. reesei* (or *H. jecorina*) α-1,2-mannosidase. The α-1,2-mannosidase is hyperglycosylated when produced by *Pichia*; hence, deglycosylation and the resulting higher mobility of the protein can be easily evaluated via SDS-PAGE. Transformation of the expression construct and selection and analysis of transformants was done as described for the hIFNβ co-expression study (results not shown). Again, significant variation in between clones is observed when comparing different EndoT transformants with the control sample (a *Pichia* strain secreting the mannosidase without intracellular EndoT). After 24 hours of induction, hyperglycosylation on the mannosidase is no longer present. Thus, if the conditions are suitable, glycoproteins may be deglycosylated by EndoT, both in vivo and in vitro, in a post-secretorial way.

Conclusions:

Four forms of soluble EndoT were expressed in *Pichia pastoris*. Deletion of the 43 C-terminal amino acids results in a sharp decrease in secretion efficiency. Nevertheless, all four forms have the capacity to deglycosylate proteins after overnight incubation in NaOAc pH 5. EndoT is active on high-mannose but not on complex N-glycans and the efficiency of deglycosylation depends on the protein backbone to which the sugars are attached.

Expression of functional EndoT[FullSize] into the *Pichia* secretion pathway was successful when fusing the enzyme to the cytosolic and transmembrane domain (first 140 N-terminal amino acids) of *S. cerevisiae* Ste13p, known to be localized in the yeast trans-Golgi network. A partial in vivo deglycosylation of co-expressed hIFNβ (a difficult substrate for EndoT) and *T. reesei* α-1,2-mannosidase was observed while a fraction of the EndoT is also secreted into the medium as result of intracellular proteolysis.

These results demonstrate that, e.g., *Pichia pastoris* can be used as a production platform for EndoT, which is an alternative for the commercially available EndoH endoglucosaminidase. Moreover, EndoT can be a valuable tool for native deglycosylation of glycoproteins, e.g., before crystallography or to remove undesired or immunogenic oligosaccharide chains, either via in vitro treatment with the enzyme or in vivo when co-expressed in a *Pichia* strain containing Golgi-localized (or possibly co-secreted) EndoT.

Since EndoT is able to trim high-mannose and hybrid N-glycans, its expression at the end of the *Pichia* secretion pathway should enable in vivo clean-up of only partially humanized N-glycans (so not yet of the complex type) on recombinant proteins produced in a glyco-engineered strain. These non-complex glycans that are produced together with complex glycans in glyco-engineered strains are a known problem, especially because they are difficult to isolate from the glycoproteins with complex glycosylation and may interfere with glycoprotein function or immunogenicity. Since the amount of non-complex N-glycans is only a fraction of the total modified N-glycan pool, moderate intracellular EndoT expression might already be sufficient to obtain a complete in vivo clean-up of residual high-mannose and hybrid oligosaccharides.

Example 2

Production of Single GlcNAc-Modified Proteins in an Engineered Yeast Strain

*Pichia pastoris* strains are available, which have been extensively engineered to produce complex-type human bi- and multiantennary N-glycans. These glycans can, moreover, be sialylated through incorporation of a CMP-N-acetylneuraminic acid synthesis pathway in the yeast cell, together with a transporter for CMP-NANA from the cytoplasm to the Golgi lumen, and α-2,6-sialyltransferase.

As an example, we work with *Pichia pastoris*-expressing human interferon-beta as described in Example 1, in which the OCH1 gene has been inactivated and in which *Trichoderma reesei* α-1,2-mannosidase, fused to a C-terminal HDEL-tag has been overexpressed, and in which also human N-acetylglucosaminyltransferase I catalytic domain fused to the N-terminal region of *S. cerevisiae* Kre2p, *Drosophila melanogaster* Mannosidase II catalytic domain fused to the N-terminal region of *S. cerevisiae* Mnn2p, human N-acetylglucosaminyltransferase II catalytic domain fused to the N-terminal region of *S. cerevisiae* Mnn2p and a fusion protein of *S. cerevisiae* Gal10p and the catalytic domain of human beta-1,4-galactosyltransferase, fused to the N-terminal region of *S. cerevisiae* Mnn2p, are all overexpressed. This strain produces biantennary, bigalactosylated N-glycans, but also the intermediates formed within this heterologously reconstructed pathway, i.e., some high-mannose glycans (including Man5GlcNAc2), and some hybrid glycans (including GalGlcNAcMan3-5) (PhD thesis Pieter Jacobs, Faculty of Sciences, Ghent University, 2008).

As described in Example 1, the 140 N-terminal amino acids of Ste13p, comprising the transmembrane region and the cytosolic domain known to contain signals for Golgi-localization, were fused to the first amino acid of Endo

[FullSize] (=fusion construct 1), and this fusion construct is transformed to the glyco-engineered hIFNβ-producing strain described in the previous paragraph. In this way, the large majority of EndoT is retained intracellularly in a late Golgi compartment and is active on the N-glycans that pass this compartment. As the Kre2p and the Mnn2p proteins from which targeting signals used for localizing the glyco-engineering enzymes were derived, are known to localize to medial Golgi compartments in yeasts, these glyco-engineering enzymes have already encountered the secreted glycoproteins before these glycoproteins reach the endoT compartment and have thus converted the glycans on these secreted glycoproteins to complex-type biantennary, bigalactosylated structures, which are resistant to endoT hydrolysis. Nevertheless, the high-mannose and hybrid-type rest-products, intermediates of the built-in pathway, encounter endoT and are hydrolyzed, leaving only 1 GlcNAc residue on the protein per N-glycosylation site thus modified, and this happens before the glycoprotein is finally secreted from the cell.

Human IFNβ contains one N-glycosylation site and is produced by *Pichia pastoris* as a mixture of a glycosylated and a non-glycosylated form, which are easily distinguishable from one another on a 15% poly-acrylamide gel. For each construct, eight single clones are grown for two days in 100 ml shake flasks containing 30 ml BMGY. Once high cell densities are reached, the expression of soluble hIFNβ and intracellular EndoT is transferred to BMMY medium. Proteins from 0.5 ml medium, taken after 24 and 40 hours of induction, are DOC/TCA precipitated, resuspended into 2× Laemmli loading buffer and analyzed on SDS-PAGE.

Comparing the ratio between secreted glycosylated and non-glycosylated (or single GlcNAc-modified) hIFNβ observed for the endoT transformants on the one hand and for the untransformed hIFNβ complex-type glyco-engineered producing strain on the other hand, shows an increase in the non-glycosylated band when endoT was expressed, but this increase is not as big as in Example 1, where high-mannose hIFNβ strains were used, of which all N-glycans are sensitive to endoT.

The glycans remaining on secreted proteins, of which the major fraction is hIFNβ, are analyzed through deglycosylation of the proteins with peptide-N-glycosidase F, labeling of the released glycans with APTS and profiling of the glycans using capillary electrophoresis on a DNA-sequencer. As expected, the peaks corresponding to high-mannose and hybrid-type N-glycan structures add up to a significantly lower percentage of the total N-glycan mixture in the proteins secreted by endoT-engineered strain as compared to the non-endoT engineered strain, demonstrating that endoT engineering is efficient in removing these high-mannose and hybrid-type glycans in vivo, thus improving the homogeneity of glycosylation of therapeutic glycoproteins produced in these glyco-engineered strains.

Example 3

Co-Secretion of Endoglucosaminidase and Glycoprotein by Glyco-Engineered Yeast

In this example, the setup of the experiment is entirely parallel to the one of Example 2, except that now we engineer the complex-type glyco-engineered hIFNβ-producing strain with an expression construct for the secretion of endoT protein, as detailed in Example 1 (where it was done in non-glyco-engineered yeast). In this fashion, endoT enzyme and hIFNβ are cosecreted in the culture medium of the yeast. As we buffer the medium at pH=6.7 and as the pH optimum for endoT enzymatic activity is around 5.0, endoT is only very poorly active during the cultivation period, thus not affecting the physiology of the yeast. Upon completion of the hIFNβ production, the culture medium is harvested and the pH is shifted to 5.0 through double dialysis to NaAc pH=5.0 through a 3000 Da MWCO dialysis membrane. The preparation is subsequently incubated at 30° C. and samples are taken after 1 hour, 2 hours, 4 hours and 16 hours for protein-linked N-glycan analysis through the method described above and for SDS-PAGE analysis. The N-glycan analysis results demonstrate that high-mannose and hybrid-type N-glycans are progressively lost with increasing incubation time, and the SDS-PAGE analysis concomitantly shows an increase in the non-glycosylated hIFNbeta band, thus demonstrating that cosecreted endoT can improve the homogeneity of hIFNbeta toward complex-type N-glycans.

Example 4

Alternative Glycosylation Using Early Targeting of Endoglucosaminidase

A *Pichia pastoris* strain expressing hIFNβ is used that is engineered with the medial-Golgi targeted fusion protein between the N-terminal targeting signal of *S. cerevisiae* Mnn2p, the Gal10p catalytic domain and the human beta-1,4-galactosyltransferase catalytic domain, as described in Example 2.

EndoT is fused to the N-terminal targeting signal of Kre2p and the above strain is transformed with the expression construct for the Kre2p-EndoT fusion protein. In published studies, N-acetylglucosaminyltransferase I was targeted with this Kre2p targeting signal, and it was demonstrated that this targeting puts the enzyme fused to it in a location so that the enzyme can convert its Man5GlcNAc2-glycoprotein substrate to GlcNAcMan5GlcNAc2-glycoprotein product before the glycoprotein reaches the secretory system compartment where Mnn2p-fusion proteins are localized. Consequently, as hIFNβ leave the ER, it encounters the Kre2p-EndoT fusion protein and its N-glycans are efficiently removed, resulting in hIFNβ being created that carries a single GlcNAc residue per N-glycosylation site. hIFNβ then moves on to the Mnn2p-Gal10GalT-containing Golgi compartment, where the single GlcNAc residues are recognized and modified with a β-1,4-Galactose residue, thus resulting in the formation of LacNAc structures, which are not a substrate for any further endogenous yeast glycosyltransferases. Thus, hIFNβ modified with LacNAc N-glycans is secreted.

Using Western blotting of the secreted glycoproteins with the lectin RCA120, it is detected that the "differentially glycosylated" low-MW hIFNβ band is modified with terminal beta-galactose residues, whereas this is not the case in the non-Kre2pEndoT-engineered control strain. This result is further confirmed to pre-treatment of the secreted proteins with β-1,4-galactosidase isolated from bovine kidney, resulting in a loss of the RCA120 lectin blotting signal.

As well-established in the art, LacNAc structures are excellent substrates for human alpha-2,6-sialyltransferase, and the sialylation pathway has been functionally incorporated in glyco-engineered *Pichia* strains, which generated LacNAc structures using Mnn2p-targeted beta-galactosyltransferase, as is also the case here. It is thus obvious to one skilled in the art that building in the published sialylation pathway in the LacNAc-N-glycan-producing Kre2pEndoT/Mnn2pGal10GalT strain described above, will result in the secretion of glycoproteins modified with alpha2,6-sialylated LacNAc N-glycans. Therapeutic glycoproteins modified in this way are expected to be both very homogenous and have a long circulation time in vivo, as they would not be recognized by hepatic and myeloid GlcNAc/Man or Gal/GalNAc receptors.

Alternatively, sialylation can be accomplished in vitro post-secretion through contacting of the LacNAc-N-glycan-modified glycoproteins with recombinant alpha-2,6-sialyltransferase and CMP-NANA, using methods well known to those skilled in the art.

Example 5

Avoidance of Cell Lysis Upon Endoglucosaminidase Expression and Glycan Profiles of Glyco-Engineered Yeast Strains Pichia strains that overexpress both the test protein hIFNβ and EndoT coupled to the cytoplasmic and transmembrane domain of Ste13p for intracellular expression were seen to give, after 48 hours of induction, a gel pattern, typical for cell lysis.

To avoid this cell lysis, probably due to weakening of the cell wall, resulting from too strong deglycosylation of its mannoproteins, an alternative EndoT overexpressing strategy was used. Instead of the strong AOX1 promoter, the AOX2 promoter was used to control the expression of EndoT. AOX2 encodes a second AOX gene with 90% homology to the AOX1 gene but is driven by a less active methanol-inducible AOX2 promoter.

A new construct was made from pPICZSTE13CytoTMEndoT where the PAOX1 was exchanged with the PAOX2 from pAOX2ZB from Invitrogen. GS115 strains overexpressing hIFNβ were transformed with the resulting plasmid. However, upon induction of these strains, no visible effect was seen from this EndoT expression, i.e., the ratio of glycosylated versus non-glycosylated hIFNβ did not change (not shown; the efficiency of intracellular EndoT processing was determined by comparing the ratio between secreted glycosylated and non-glycosylated hIFNβ observed for the transformants on the one hand and for the untransformed hIFNβ-producing strain on the other hand).

Another approach is to overexpress EndoT extracellulary in the medium together with the test protein. Therefore, another plasmid was made where the EndoT, fused to the pre-pro region of the S. cerevisiae alpha mating factor for extracellular expression, was placed under transcriptional control of the AOX2 promoter. Again, GS115 strains overexpressing hIFNβ were transformed with the resulting plasmid. Upon induction of these strains, no visible effect was seen from this EndoT expression, i.e., the ratio of glycosylated versus non-glycosylated hIFNβ did not change (not shown).

This could be explained by the suboptimal pH for EndoT of the medium buffered to a pH 7. Therefore, the induced medium containing soluble EndoT and the hIFNβ test protein was incubated in a NaOAc pH 5 buffer at 30° C. respectively for 1 hour, 3 hours and ON and compared to the untreated medium of the eight different clones, as well as to the parent GS115 strain expressing hIFNβ, i.e., without EndoT (results not shown).

From these gels, we can conclude the soluble extracellular expressed EndoT indeed acts on the high mannose glycosylated hIFNβ, when the pH is lowered to 5. Prolongation of the treatment results in a better deglycosylation. However, full deglycosylation appeared hard to achieve; this indicates again that hIFNβ is a difficult substrate for EndoT.

Figure 3:
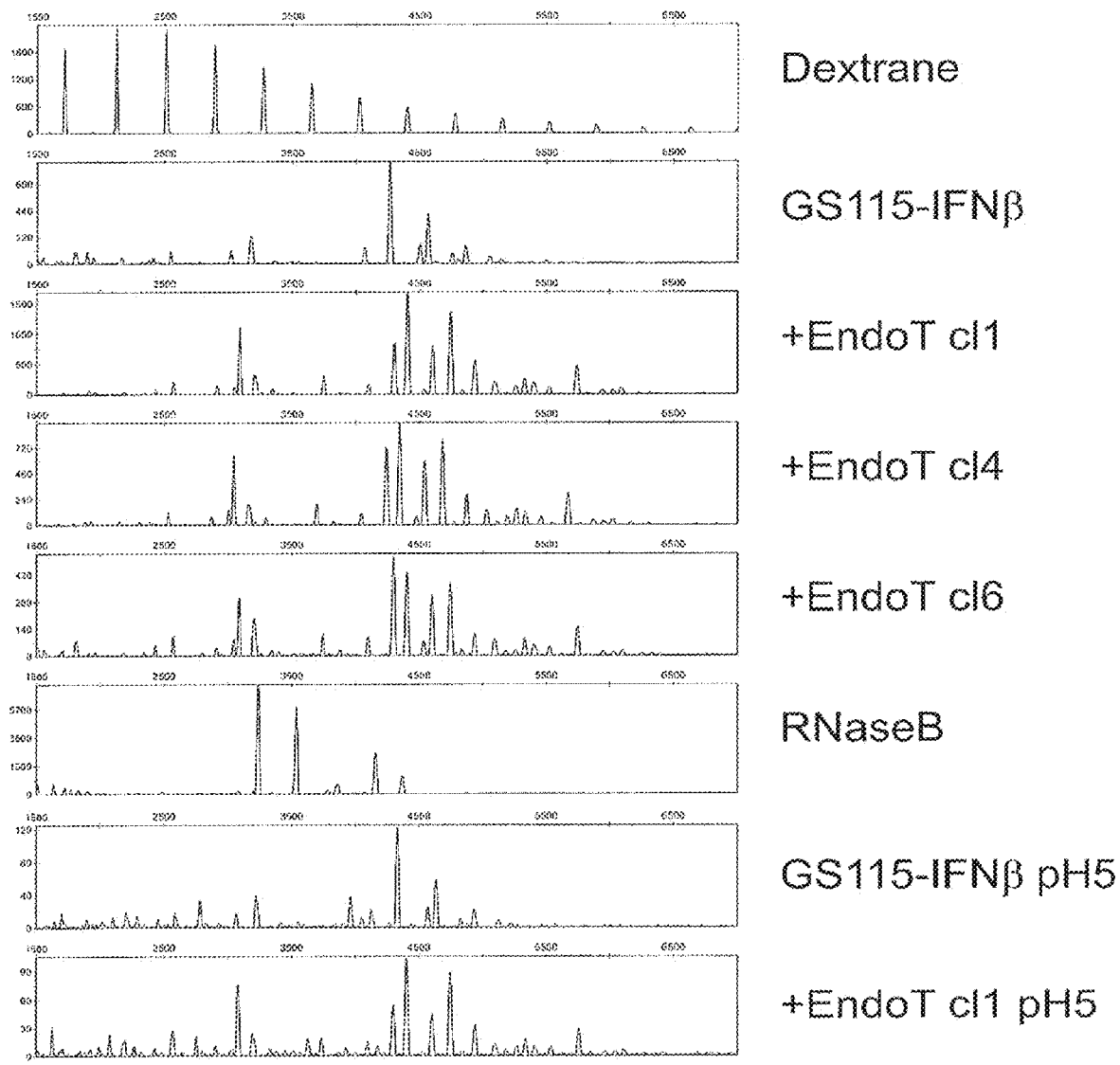
FIG. 3: Glycan profiles of a GS115 yeast strain overexpressing IFNβ (panel 2), different clones also expressing EndoT (panels 3-5), yeast treated with RNase B (panel 6), and the strains of panels 2 and 3 with lowering pH to 5 in the induced medium (panels 7-8). The vertical axis is presented in values of Relative Fluorescence Units.

Glycan profiles were analyzed from clones 1, 4 and 6 and compared to GS115, with and without lowering of the pH to 5 in the induced medium. Extracellular soluble overexpression of EndoT seemed to already alter the glycanprofile of the hIFNβ strains overexpressing EndoT compared to WT hIFNβ strains (FIG. 3). This might indicate cell stress.

Figure 4A:
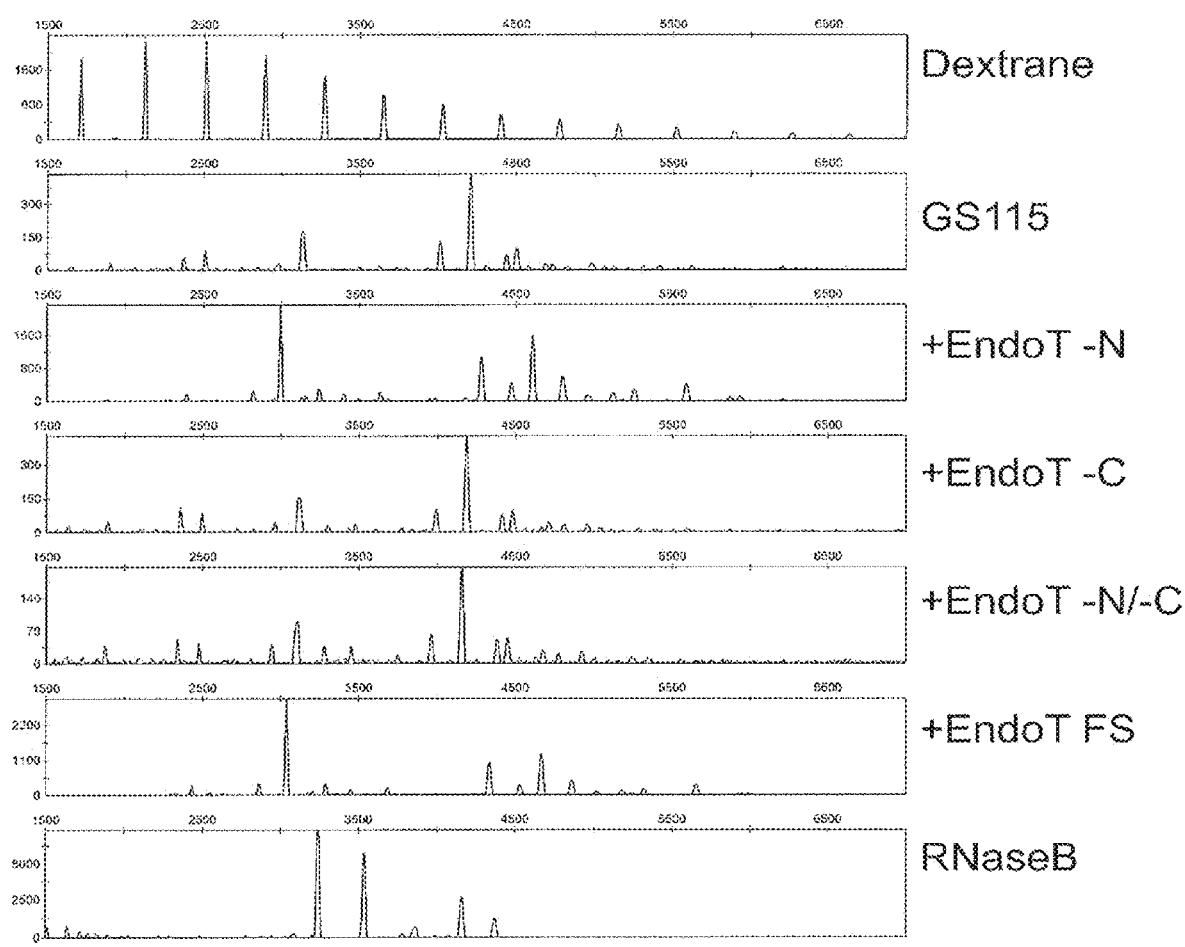
FIGS. 4A and 4B.
Figure 4B:
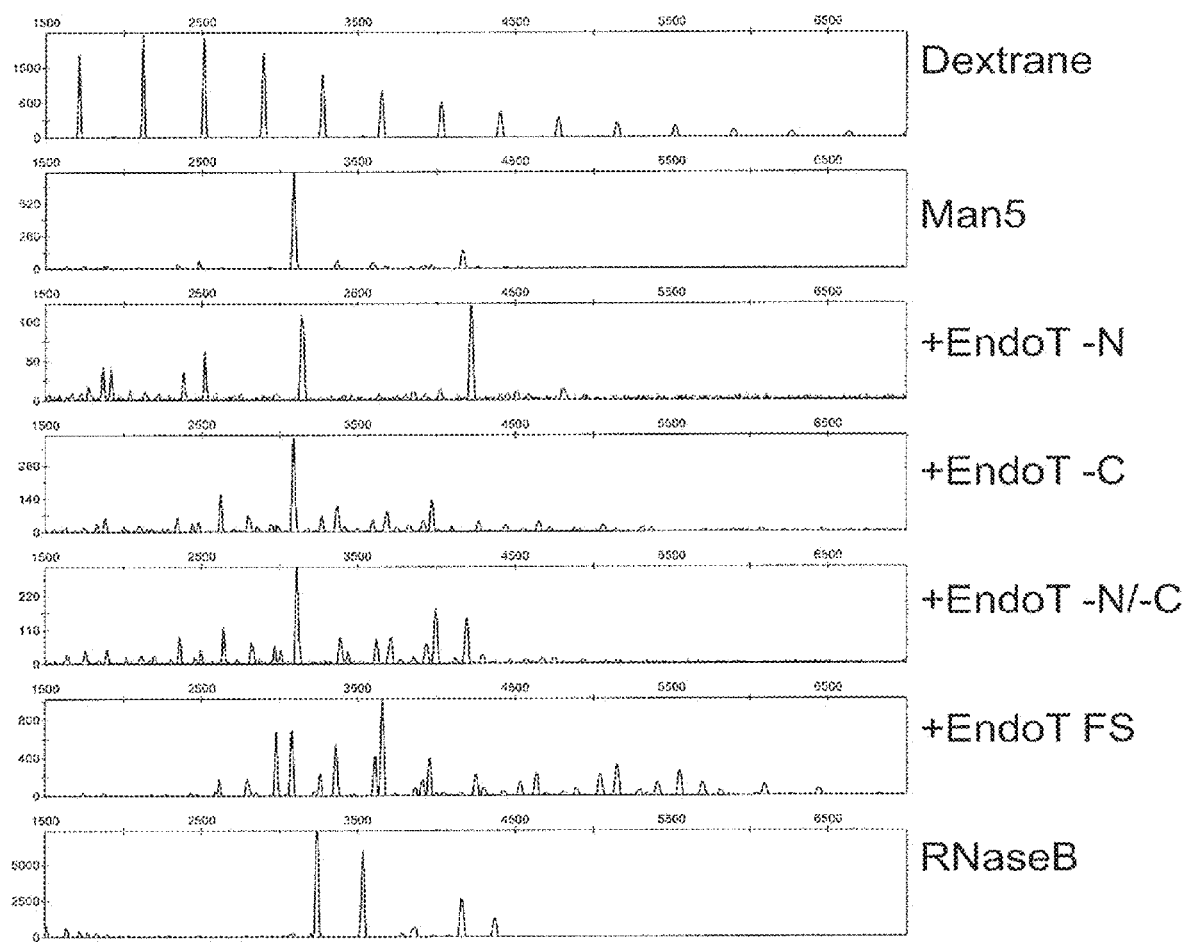
Figure 5A:
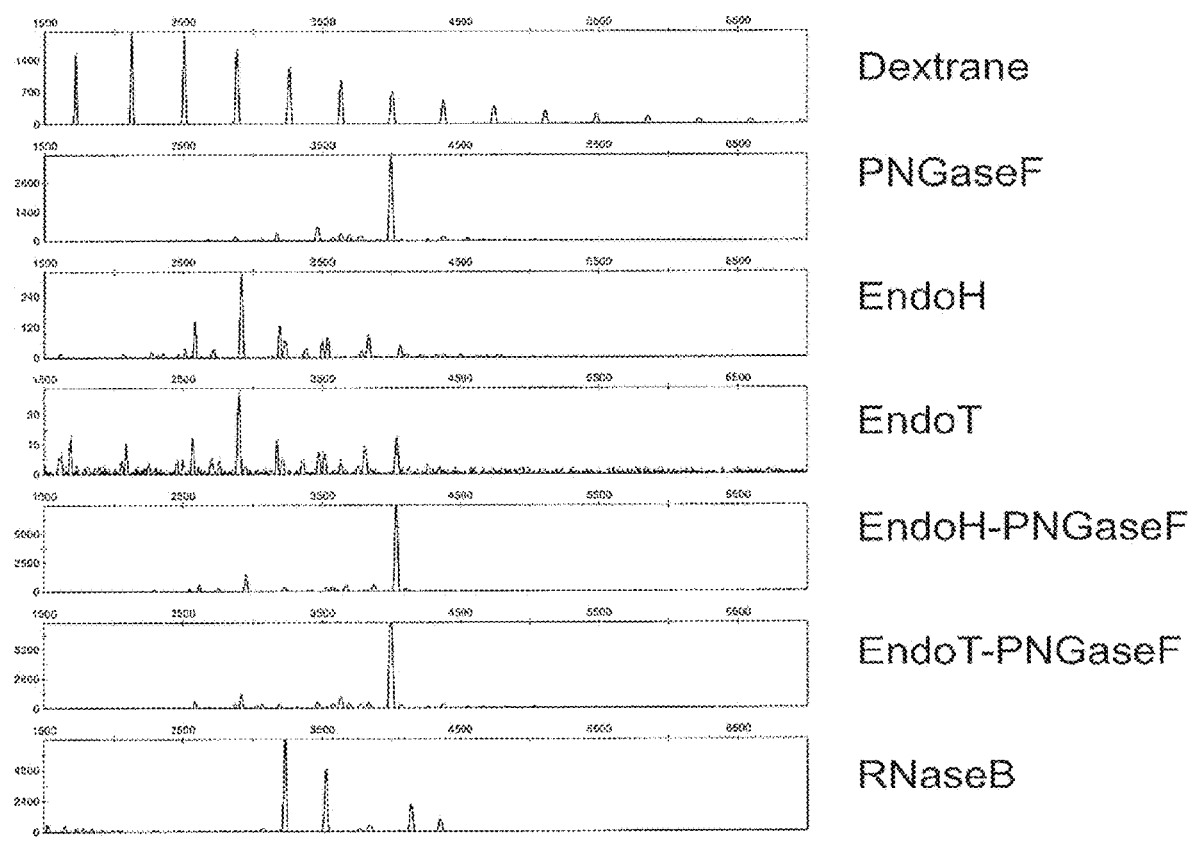
FIGS. 5A through 5F: Glycan profiles of different glyco-engineered yeast strains producing GM-CSF as glycoprotein.
Figure 5B:
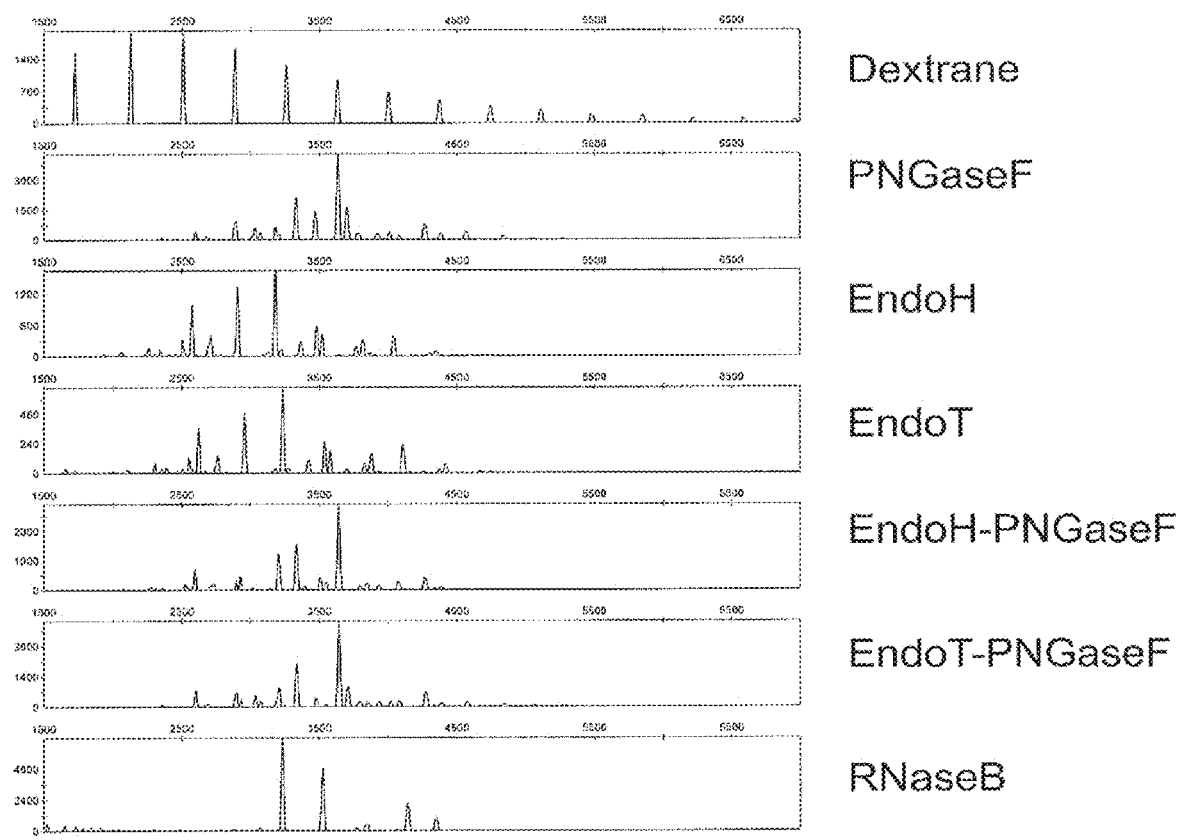
Figure 5C:
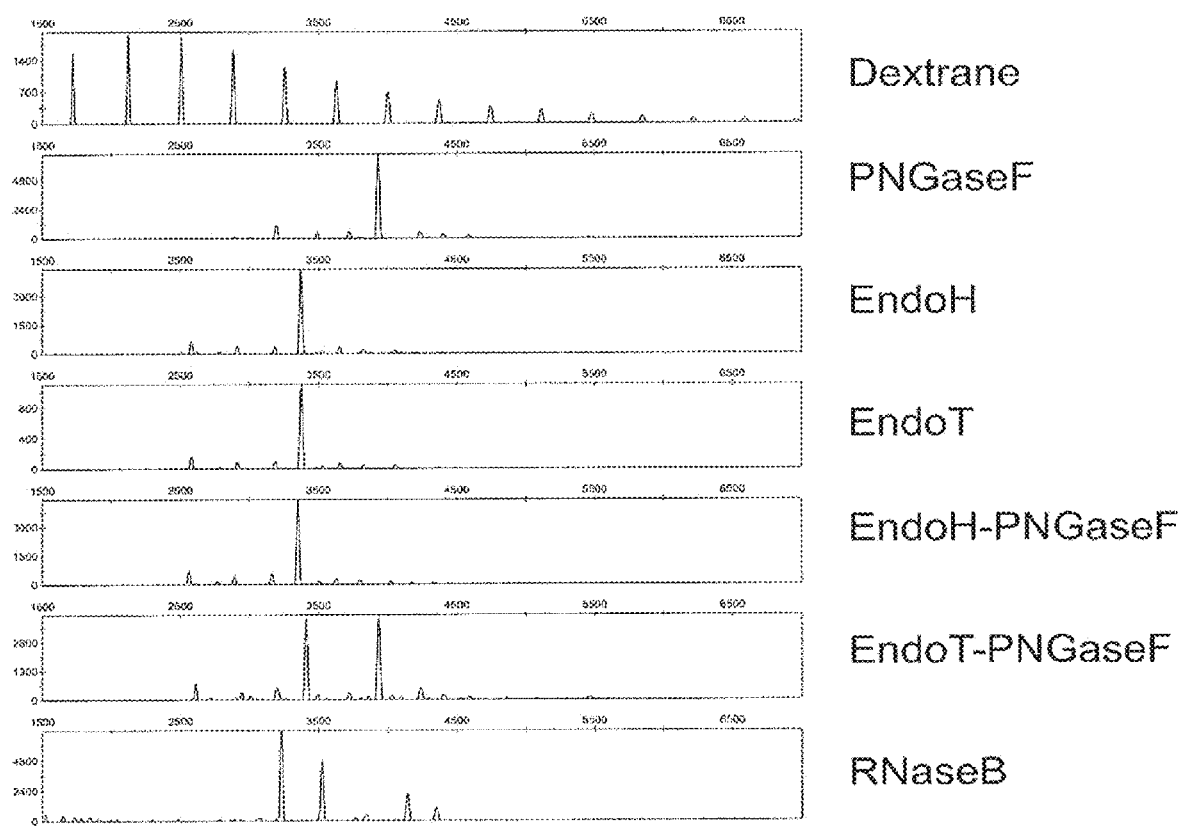
Figure 5D:
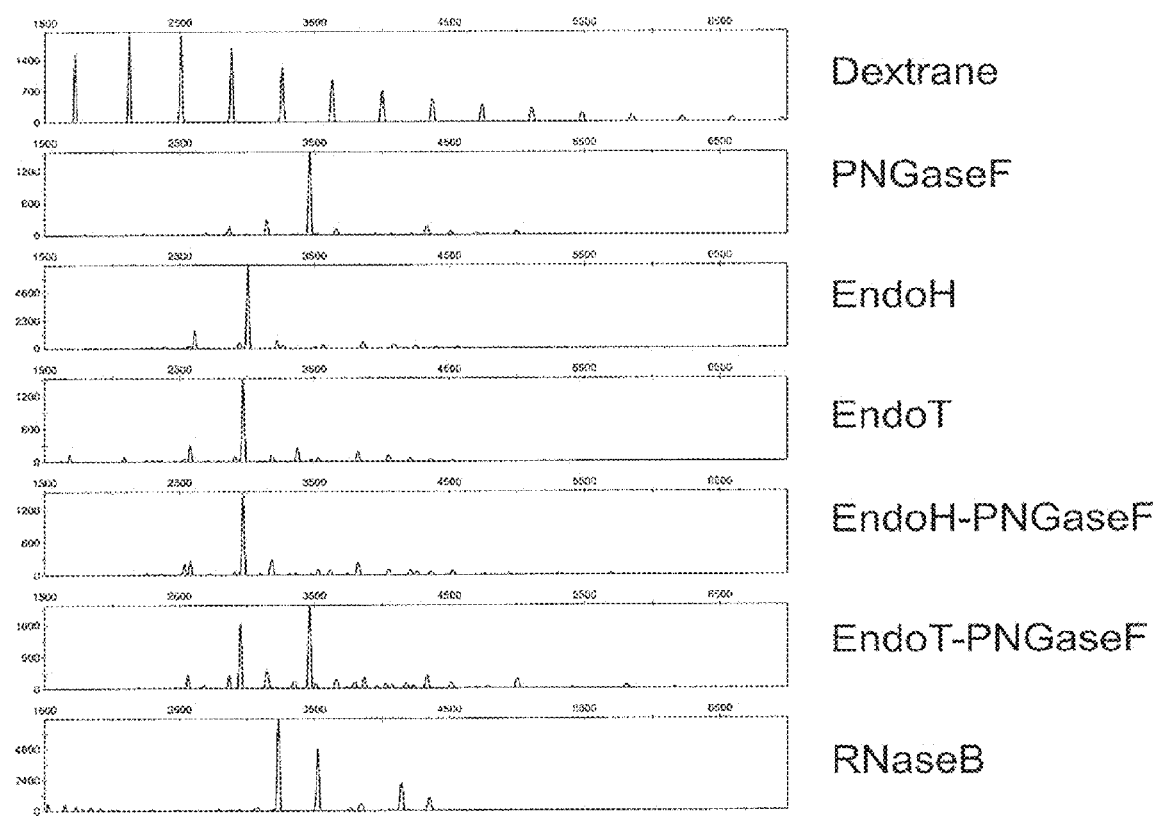
Figure 5E:
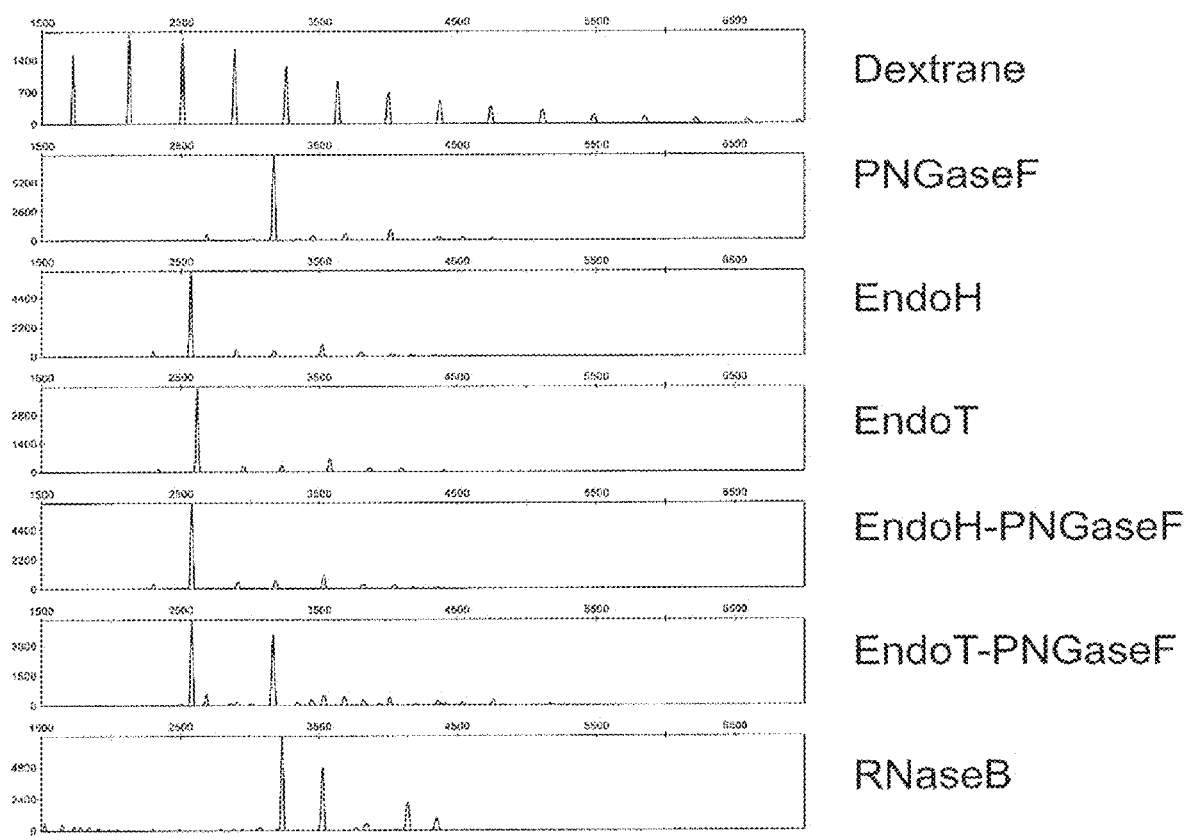
Figure 5F:
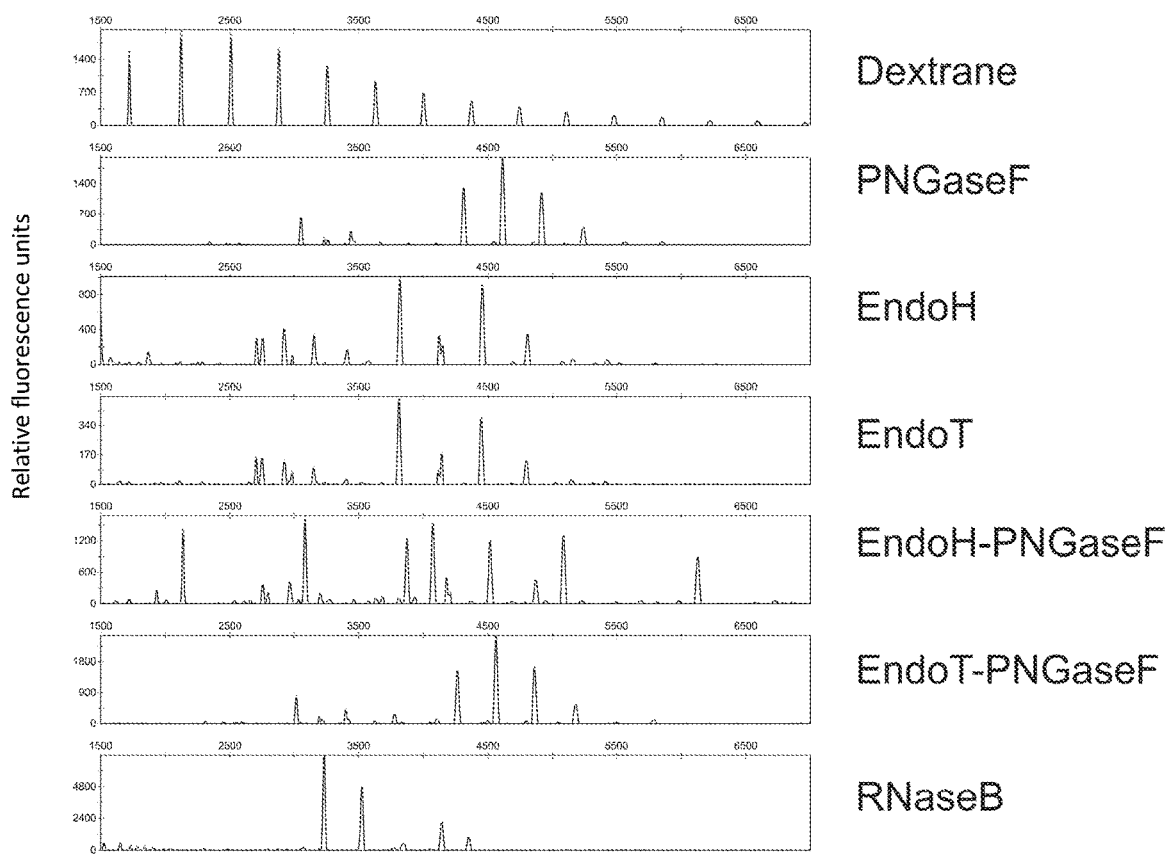

The glycan patterns of the Pichia strains (the WT strain GS115 and Man5-glycoengineered strain) soluble overexpressing the different EndoT forms, N-terminal truncated, C-terminal truncated, C- and N-terminal truncated or full size were also analyzed. The glycan profiles reveal that when overexpressing EndoT in the extracellular medium, the sugar composition of these strains is altered. Thus, the production of EndoT in the cells and its passage through the secretory pathway has an influence on the glycans of the strain (FIG. 4), so overexpressing EndoT in the yeast cells is not without consequences.

Next, the use of EndoT in the cleanup of glyco-engineered strains was tested. Since EndoT is able to trim high-mannose (and hybrid) N-glycans, its expression at the end of the Pichia secretion pathway should enable in vivo clean-up of only partially humanized N-glycans (so not yet of the complex type) on recombinant proteins produced in a glycoengineered strain. Since the amount of non-complex N-glycans is only a fraction of the total modified N-glycan pool, moderate intracellular EndoT expression might already be sufficient to obtain a complete in vivo clean-up of residual high-mannose and hybrid oligosaccharides.

Therefore, in vitro digests were performed on several different glycoengineered strains producing GmCSF as a test protein. The strains in order of engineering: GS115, Man5, GlcNAcMan5, GalGlcNAcMan5, GalGlcNAcMan3, Gal2GlcNAc2Man3 (named after glycosylation products).

These strains were methanol induced for 48 hours and sugars were prepared and labeled. To remove the sugars from the glycoproteins, EndoT was used in comparison with other glycosidases PNGaseF and EndoH. Like EndoH, but unlike PNGase F, EndoT indeed seems unable to cut the complex type glycan Gal2Gn2Man3. In the case of GalGn-Man3, the results are still inconclusive and further experiments need to be done to check whether EndoT could really help in cleaning up the heterogeneous glycosylation pattern. On the other hand, it is clear that EndoT acts on all the presented sugar structures that contain a 6' pentmannosyl group (FIG. 5). In panel 5 of the GMCSF-GS115 strain (FIG. 5F), a contaminating polymer is present, causing the aberrant glycan profile.

After EndoT/EndoH digest, another PNGaseF digest was performed on the immobilized glycoproteins on the membrane, to check if there was still some glycoprotein left that could be deglycosylated with PNGaseF (panels 5-6). Although some of these data are still inconclusive since product of an EndoT/H digest seems to still be present, it seems to confirm that EndoT and EndoH, unlike PNGase F, are unable to cut the complex type glycan Gal2Gn2Man3.

"Cleaning up" of the unwanted glycan structures thus evidently depends on the specificity of the endoglucosaminidase used. However, as EndoT hydrolyzes high mannose glycans, a wild-type strain (i.e., that produces only high mannose glycans) that overexpresses EndoT in large enough amounts yields a strain that makes single GlcNAc-residues as N-glycosylation structures.

Example 6

In Vivo De-N-Glycosylation by Targeting of the Fungal endoT Enzyme to the Golgi-Apparatus of HEK293S GnTI$^{-/-}$ Cells To avoid in vitro deglycosylation, in vivo de-N-glycosylation in a HEK293S cell-line was implemented. Identification and cloning of a fungal gene (Genbank Acc. No. CS423050) that encodes an endoH-type endoglycosidase, denoted as endoT because it was cloned from the filamentous fungi *Trichoderma reesei* (PhD thesis Ingeborg Stals, Ghent University, 2004), allows us to do so. The work is carried out in a glucosaminyltransferase I negative HEK cell-line (Reeves, Callewaert et al., *PNAS* (2002) 99:13419-13424). This cell-line almost exclusively produces Man$_5$GlcNAc$_2$-N-glycans, which are hydrolyzed in the chitobiose bond by endoH-type endoglycosidases.

EndoT is secreted by *T. reesei* (now designated as *Hypocrea jecorina*), which is indicative for the fact that it is adapted to folding in the eukaryotic secretion pathway. In order not to interfere with the function of N-glycans in protein folding, endoT is targeted to the trans-golgi/trans-golgi network.

Strategy

Targeting the endoT enzyme to the trans-golgi/TGN of the HEK293S cell-line is achieved by fusing the trans-golgi-targeting signal of a golgi-retained glycosyltransferase. Most golgi-resident glycosyltransferases are subject to proteolytic splicing in the stalk region to a lesser or greater extent (Jaskiewicz, *J. Biol. Chem.* 271(42):26395-26403 (1996)). The human β-galactoside-α-2,6-sialyltransferase (ST6GalI) or the human ganglioside-GM$_2$-synthase (GalNAcT) N-terminus is fused to the N-terminus of the full-length endoT enzyme. The β-galactoside-α-2,6-sialyltransferase (ST6GalI) has been characterized better and its N-terminus is retained in the trans-golgi, but it contains several cleavage sites and is probably subject to proteolytic processing (Kitazume-Kawaguchi et al., *Glycobiology* 9(12):1397-1406 (1999)).

The GM2-synthase N-terminus is shorter: only the first 27 amino acids seem to determine trans-golgi retention (Uliana et al., *Traffic* 7:604-612 (2006)) and only contains one cathepsin-D splice site between amino acids 22 and 23 (GL-LYAST) (Jaskiewicz, *J. Biol. Chem.* 271(42):26395-26403 (1996)). If too much cleaved, endoT fusion protein is secreted; these sequences are mutated to a non-spliced sequence.

To evaluate proteolytic cleavage and targeting on the one hand and the efficiency of the in vivo de-N-glycosylation on the other, expression constructs for transient mammalian expression are made, using the mammalian expression vector pCAGGS (Niwa et al., *Gene* 108:193-200 (1991)). MYC-tagged constructs for the two fusion proteins allow for subcellular localization experiments and to assess secretion. Subcellular localization experiments are carried out using an anti-MYC antibody immunofluoresence microscopy and a trans-golgi-targeting pHluorin construct (on the World Wide Web at bristol.ac.uk/synaptic/research/projects/mechanisms/phluorins.htm) as a positive control. Secretion of the MYC-tagged endoT protein is evaluated by Western blot with an anti-MYC antibody and by using a MYC-tagged endoT without an N-terminal golgi-targeting sequence as a negative control.

A soluble, secreted form of the glycoprotein hemagglutinin H3 is used to cotransfect to the HEK293S cell-line and allows evaluation of the de-N-glycosylating activity of the endoT fusion protein. Such a hemagglutinin coding sequence is also cloned into the pCAGGS vector. As hemagglutinin is intracellularly deglycosylated by endoT, a shift in molecular weight is observed on SDS-PAGE.

The best golgi-targeting signal is then used to make a final construct with the chosen fusion protein. Constitutive, as well as tetracycline-inducible, expression is envisaged.

For tetracycline-inducible expression, the pcDNA4/TO (Invitrogen) vector is used. A stable cell-line is thus produced by selection with zeocin. The HEK293S GnTI−/− cell-line already contains a pcDNA6/TR construct, which encodes the Tet-repressor protein. This is constitutively and stably expressed and represses transcription from the pcDNA4/TO plasmid (Invitrogen) until tetracycline is added.

For constitutive expression, any mammalian expression vector containing a constitutive promoter and a selection marker (not blasticidin, already in use for pcDNA6/TR) can be used.

Example 7

In Vivo De-N-Glycosylation of Glycoproteins by Targeting of the Fungal endoT Enzyme to the Secretory Pathway of Eukaryotic Organisms Strains, Culture Conditions and Reagents.

*Escherichia coli* strains MC1061 were used for the amplification of recombinant plasmid DNA and grown in a thermal shaker at 37° C. in Luria-Broth (LB) medium supplemented with 100 μg/ml of carbenicillin or 50 μg/ml of kanamycin, depending on the plasmids used.

Construction of pCAGGS-hST-endoT

The coding sequence for a fusion protein of which the N-terminal part consists of the first 100 amino acids of the human β-galactoside-α-2,6-sialyltransferase (Genbank Acc. No. NM_003032) and the C-terminal part consists of the full-size endoT, without signal sequence, was constructed as described (SEQ ID NO:14):

The endoT coding sequence with N- and C-terminus present, but without the signal sequence, was amplified from pUC19endoT (full size) (see, above) by PCR with oligonucleotides "endoT.fusion.fw.251007" (TABLE 1) and "endoT.Bsu36I.rev.231007" (TABLE 1) and purified by agarose gel electrophoresis.

The N-terminal part of the human β-galactoside-α-2,6-sialyltransferase was amplified from a HepG2 library (Hepatoma cDNA library) by PCR with oligonucleotides "hST-GalI.XhoI.fw.231007" (TABLE 1) and "hSTGalI.fusion.rev.251007" (TABLE 1) and purified by agarose gel electrophoresis.

The coding sequence for the fusion protein was amplified by fusion PCR, using these two PCR fragments as templates and with oligonucleotides "hSTGalI.XhoI.fw.231007" (TABLE 1) and "endoT.Bsu36I.rev.231007" (TABLE 1). The resulting fragment was digested with Bsu36I and XhoI, and ligated into a pCAGGS vector (Niwa et al., *Gene* 108:193-200 (1991)) that was also digested with Bsu36I and XhoI and treated with Calf Intestine Phophorylase (CIP). The insert in the resulting plasmid was sequenced using oligonucleotides "pCAGGSF" and "pCAGGSRMARCO."

Construction of pCAGGS-hST-endoT-myc

The coding sequence for a fusion protein of which the N-terminal part consists of the first 100 amino acids of the human β-galactoside-α-2,6-sialyltransferase (Genbank Acc. No. NM_003032) and the C-terminal part consists of the full-size endoT, without signal sequence and containing a C-terminal MYC-tag, was constructed as described (SEQ ID NO:16):

The sequence encoding the fusion protein with a C-terminal MYC-tag was amplified from pCAGGS-hST-endoT by PCR with oligonucleotides "hSTGalI.XhoI.fw.231007" (TABLE 1) and "endoT.Bsu36I.rev.231007" (TABLE 1). The resulting fragment was purified by agarose gel electrophoresis and cloned into a pCR-bluntII-topo plasmid by topo-cloning, resulting in the construct Topo-hST-endoT-myc. This construct was sequenced with oligonucleotides "SP6" (TABLE 1) and "T7" (TABLE 1) and the sequence of the fusion protein with C-terminal MYC-tag confirmed.

Topo-hST-endoT-MYC was digested with Bsu36I and XhoI, the fragment containing the endoT construct was purified from the mix by agarose gel electrophoresis and ligated into a pCAGGS vector (Niwa et al., Gene 108 (1991), 193-200) that was also digested with Bsu36I and XhoI and treated with CIP.

Construction of pCAGGS-hGalNAcT-endoT

The coding sequence for a fusion protein of which the N-terminal part consists of the first 27 amino acids of the human UDP-GalNAc:lactosylceramide/GM3/GD3 β-1,4-N-acetyl-galactosaminyltransferase (GalNAc-T or GA2/GM2/GD2 synthase) (Genbank Acc. No. NM_001478) and the C-terminal part consists of the full size endoT, without signal sequence, was constructed as described (SEQ ID NO:18):

The endoT coding sequence with N- and C-terminus present but without the signal sequence was amplified from pUC19endoT (full size) (see, above) by PCR with oligonucleotides "endoT.fushGalNacT.fw.231107" (TABLE 1) and "endoT.Bsu36I.rev.231007" (TABLE 1) and purified by agarose gel electrophoresis.

The N-terminal part of the human GM2 synthase was amplified from a fetal brain cDNA library (Dr. S. Ryckaert) by PCR with oligonucleotides "hGalNAcT.fw.XhoI.231107" (TABLE 1) and "hGalNacT.fus.rev.231107" (TABLE 1) and purified by agarose gel electrophoresis.

The coding sequence for the fusion protein was amplified by fusion PCR, using these two PCR fragments as templates and with oligonucleotides "hGalNAcT.fw.XhoI.231107" (TABLE 1) and "endoT.Bsu36I.rev.231007" (TABLE 1). The resulting fragment was purified by agarose gel electrophoresis and cloned into a pCR-bluntII-topo plasmid by topo-cloning, resulting in the construct Topo-GalNAcT-endoT. This construct was sequenced with oligonucleotides "SP6" (TABLE 1) and "T7" (TABLE 1) and the sequence of the fusion protein was confirmed.

Topo-hGalNAcT-endoT was digested with Bsu36I and XhoI, the fragment containing the endoT construct was purified from the mix by agarose gel electrophoresis and ligated into a pCAGGS vector (Niwa et al., Gene 108 (1991), 193-200) that was also digested with Bsu36I and XhoI and treated with CIP.

Construction of pCAGGS-hGalNACT-endoT-myc

The coding sequence for a fusion protein of which the N-terminal part consists of the first 27 amino acids of the human UDP-GalNAc:lactosylceramide/GM3/GD3 β-1,4-N-acetyl-galactosaminyltransferase (GalNAc-T or GA2/GM2/GD2 synthase) (Genbank Acc. No. NM_001478) and the C-terminal part consists of the full-size endoT, without signal sequence and containing a C-terminal MYC-tag, was constructed as described (SEQ ID NO: 20):

The sequence encoding the fusion protein with a C-terminal MYC-tag was amplified from Topo-hGalNAcT-endoT by PCR with oligonucleotides "hGalNAcT.fw.XhoI.231107" (TABLE 1) and "endoT.rev.myc.Bsu36I" (TABLE 1). The resulting fragment was purified by agarose gel electrophoresis and digested with XhoI and Bsu36I and ligated into a pCAGGS vector (Niwa et al., Gene 108 (1991), 193-200) that was also digested with Bsu36I and XhoI and treated with CIP.

Cell Lines, Buffers and Antibodies

The Hek293S-Flt3 cell-line was obtained from Prof. S. Savvides (Department of Biochemistry and Microbiology, Faculty of Sciences, UGent). Cells were grown in DMEM/F12 medium (Gibco BRL, Invitrogen), supplemented with the following sterile supplements: 10% fetal calf serum, L-glutamin (0.3 g/L), penicillin G (100 u/mL), streptomycin (100 µg/mL). Serum-free medium has the same formulation, with only the serum omitted. Lipofectamine 2000 was from Gibco BRL, Invitrogen. Tissue culture grade Tetracycline hydrochloride was from Sigma.

Phosphate buffered saline (PBS) is 137 mM NaCl, 2.7 mM KCl, 10 mM Na2HPO4.2H2O, 2 mM KH2PO4 and pH of 7.5. Chelating sepharose 6B beads were from Pharmacia LKB.

The mouse monoclonal Penta-His IgG$_1$ antibody (BSA free) was from Qiagen; the mouse monoclonal anti-c-myc IgG$_1$ antibody was produced in-house; the sheep anti-mouse IgG$_1$ HRP-linked whole antibody was from Amersham, GE healthcare.

Transient Transfection of endoT Constructs in Mammalian Cells pCAGGS-hST-endoT, pCAGGS-hST-endoT-myc, pCAGGS-hGalNAcT-endoT and pCAGGS-hGalNAcT-endoT-myc were produced as described. These plasmids, and also the empty pCAGGS plasmid, were used to transiently transfect the Hek293S-Flt3 cell-line. As a negative control, the cells were also transfected without DNA. Cells were seeded at 200,000 cells per well in a six-well plate two days prior to transfection so that they are at least 85%-90% confluent at the day of transfection. Six hours prior to transfection, half of the medium was replaced by serum-free medium and three hours prior to transfection, all medium (3 mL) was replaced by 2 mL of serum-free medium. DNA lipoplexes were prepared by combining 4 µg of plasmid DNA with 10 µL of lipofectamine 2000 in 500 µL serum-free medium and incubating for 20 minutes at room temperature. After incubation, the lipoplexes were added to the cells and incubated overnight. The next morning, 1 mL of medium containing 30% serum was added to each well, to make a total serum concentration of 10%.

At the same time of transfection, 2 µg/mL Tetracycline Hydrochloride was added to each well to induce production of the Flt3 extracellular domain (secreted). 0.5 ml of the medium (without cells) was collected 48 and 72 hours after transfection and stored at −20° C. for later analysis.

Sample Preparation of Medium Samples for Flt3 Detection

The medium samples containing BSA (from the fetal calf serum) were cleaned up using chelating sepharose 6B beads loaded with nickel ions.

Bead preparation: 500 µL beads were loaded with 1 mL of 100 mM nickel sulphate and incubated for 5 minutes at RT. They were spun down for 1 minute at 500 g in a microcentrifuge and the supernatant was discarded. After this, they were washed with 1 mL of PBS, spun down for 1 minute at 500 g and the supernatant was discarded. This wash step was repeated five times, and after the last wash, 500 µL of PBS was added.

Selective enrichment of his-tagged Flt3: to a sample of 250 µL, an equal amount of 2×PBS was added. 25 µL from the beads slurry (prepared as described above) was added to this, and the mix was incubated on a rotating platform for one hour.

After this, the beads were spun down for 1 minute at 500 g and the supernatant was discarded. 0.5 mL of PBS was added to the beads, they were spun down for 1 minute at 500 g and the supernatant was discarded. This wash step was done three times in total.

The beads were resuspended in 250 µL of PBS. Of the resulting samples, 20 µL was taken, to which 10 µL of 3× Laemlli buffer with β-mercapto ethanol was added and the samples were cooked for 5 minutes.

Detection of Secreted Flt3 by Western Blot

After sample preparation, 30 µL of each sample was loaded onto a 10% SDS-PAGE gel and run. The gel was blotted semi-dry to a nitrocellulose membrane and detection of the his-tagged Flt3 protein was performed with a primary penta-his antibody diluted 1/1000 and a secondary anti-mouse IgG1 diluted 1/5000.

Detection of Secreted endoT Constructs by Western Blot

The same medium samples were also used to assess secretion of (proteolytically cleaved) endoT fusion proteins. 10 µL of 3× Laemlli buffer with β-mercapto ethanol was added to 20 µL of the original samples, and these were run on a 10% SDS-PAGE gel. After blotting to a nitrocellulose membrane, detection was performed using an anti-myc primary antibody diluted 1/3000 and an anti-mouse secondary antibody diluted 1/5000.

Results

The Hek293S-Flt3 was generated by the group of Prof. S. Savvides from the parental cell-line Hek293S-RicR, which produces almost exclusively Man5GlcNAc2 N-glycans. It is a stable transfectant line for the his-tagged extracellular domain of the human Flt3 receptor; this protein goes through the secretory pathway.

Transient Transfection of endoT Constructs into Mammalian Cells

The transfection protocol used allows us to transfect the cells with an efficiency of about 30%-40% (assessed by FACS, results not shown). Daily microscopic observation showed no significant cell death or a slower growth than the negative control well (transfection with no DNA) after transfecting any of the endoT fusion proteins or the empty pCAGGS plasmid.

Sample Preparation of Medium Samples for Flt3 Detection

Figure 6:
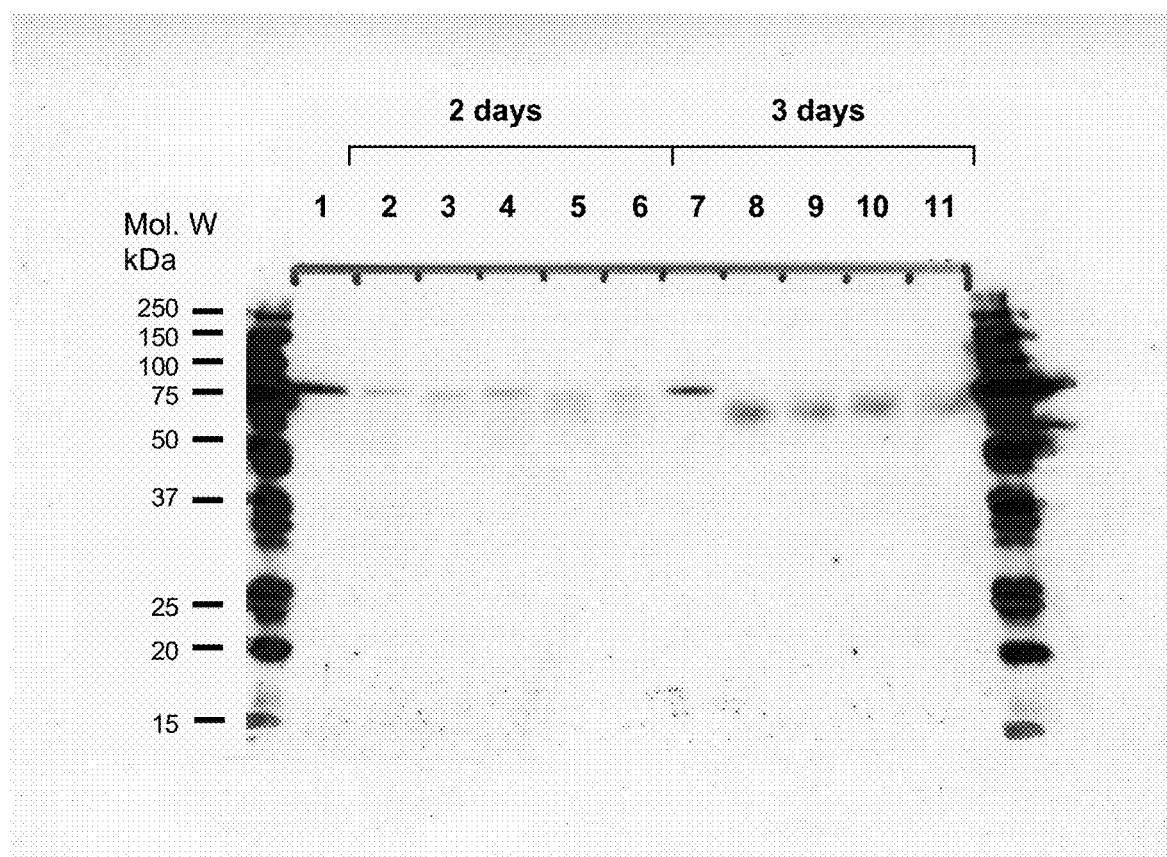
FIG. 6: Western blot for Flt3 expression in Hek293 cells, detection with penta-His primary antibody. Lane 1: positive control; lanes 2-6: 48 hours post-transfection; lanes 7-11: 72 hours post-transfection; lanes 2 and 7: supernatant from pCAGGS transfected cells (negative control); lanes 3 and 8: supernatant from pCAGGS-hGalNAcT-endoT transfected cells (i.e., with endoT fused to human GM2-synthase targeting domain); lanes 4 and 9: supernatant from pCAGGS-hGalNAcT-endoT-myc transfected cells (with myc-tag); lanes 5 and 10: supernatant from pCAGGS-hST-endoT transfected cells (i.e., with EndoT fused to human β-galactoside-α-2,6-sialyltransferase targeting domain); lanes 6 and 11: supernatant from pCAGGS-hST-endoT-myc transfected cells. After three days, fully glycosylated Flt3 is only detectable in the negative control (lane 7), indicating that EndoT is functional in all EndoT transfected cells.

Because of the presence of a high amount of bovine serum albumin (BSA) (runs at ~66 kDa) in the samples, and the fact that the secreted, non-deglycosylated Flt3 receptor runs at about 70 kDa, immunodetection of the Flt3 and especially detection of the deglycosylated forms of this protein, which run in the BSA area at a slightly lower molecular weight than 70 kDa, is obscured by a specific staining by the excess BSA and blocking of the actual Flt3 signal (see, FIG. 6). Therefore, it is convenient to purify the Flt3 from the samples to a certain extent, using a cleanup step with nickel-loaded chelating sepharose beads. This step selectively enriches the Flt3 molecules in the sample, since they are his-tagged, and detection becomes possible.

Flt3 Western Blot: Processing by endoT

The secreted Flt3 extracellular domain contains nine putative N-glycosylation sites (Rosnet et al., 1993). Up to this date, seven of these sites have been confirmed to be modified with N-glycans (personal communication, K. Verstraete). It is expected that removal of at least some of the glycans by the endoT fusion proteins will cause a band-shift on Western blot. FIG. 6 shows that this is indeed the case. Two days post-transfection and induction, some processing of the Flt3 produced by the pCAGGS-hST-endoT and pCAGGS-hST-endoT-myc transfected cells can be observed. After three days, no more fully glycosylated Flt3 can be observed in any of the samples produced by endoT transfected cells (see, FIG. 6). The fact that the Flt3 bands originating from the cells transfected with the myc-tagged endoT fusion proteins show the same behavior as the ones from the non-myc-tagged endoT fusion protein transfected cells, in both cases, is indicative for the fact that the c-myc tag does not seriously interfere with the function of the fusion proteins.

Detection of endoT Constructs by Western Blot

Both endoT fusion protein constructs were also tagged C-terminally with a c-myc tag. This allows for assessment of proteolytic processing and subsequent secretion of the golgi-luminal domain of the endoT fusion proteins, which should then be detected in the supernatant by Western blot. This is indeed the case for the endoT fused N-terminally to the targeting domain of the human GM2-synthase (pCAGGS-hGalNAcT-endoT-myc) (not shown). Processing at a cathepsin D-like splice site (GL-LYAST) between amino acids 22 and 23 would give rise to a secreted fragment of ~39.1 kDa (non-glycosylated, myc-tagged form). The secreted fragment has about this size. The Coomassie stained SDS-PAGE gel shows small but clearly defined bands in the lanes loaded with supernatant samples from pCAGGS-hGalNAcT-endoT and pCAGGS-hGalNAcT-endoT-myc transfected cells, with a slight difference in MW, attributed to the presence or absence of the myc-tag (1.2 kDa) (not shown).

The endoT fused to the targeting domain of the human β-galactoside-α-2,6-sialyltransferase (hST) does not seem to be secreted in significant amounts, since no fragment can be detected on Western blot three days after transfection with the pCAGGS-hST-endoT-myc plasmid. The first 27 amino acids of the fusion protein make up for the cytoplasmic and transmembrane domains. This means that, theoretically, anywhere between amino acid 27 and 100 (this is the portion of the hST used), proteolytic splicing could occur and give rise to a fragment of 38.6 kDa to 46.5 kDa. Even if N-glycans are present (four sites on endoT, no sites on hST targeting domain), taking into account that N-glycans are of the Man5GlcNAc2 form, the protein would be outside of the BSA occluded area around 66 kDa (~60-70 kDa) and thus would be detected on Western blot. Also, the Coomassie stained SDS-PAGE gel shows no extra bands not present in the negative control lanes (transfection with empty pCAGGS) (not shown). All this indicates that the endoT protein indeed remains inside the cell and thus is efficiently targeted.

TABLE 1

| Primers: | Name: | Use: |
|---|---|---|
| GCACTCGAGATGATTCACAC CAACCTGAAGA (SEQ ID NO: 22) | hSTGalI.XhoI.fw.231007 | Amplification hST6GalI N-terminal fragment, includes start codon and XhoI site |

TABLE 1-continued

| Primers: | Name: | Use: |
|---|---|---|
| TTAACGGGTACGTCCTTGTT CCACACCTG (SEQ ID NO: 23) | hSTGalI.fusion.rev.251007 | Amplification of hST6GalI N-terminal fragment, includes sequence for fusion PCR to endoT fragment |
| GCACTCGAGATGTGGCTGGG CCGCCGGG (SEQ ID NO: 24) | hGalNAcT.fw.XhoI.231107 | Amplification of hGalNAcT N-terminal fragment, includes start codon and XhoI site |
| TTAACGGGTACGGTGCTCGC GTACAGGAGCC (SEQ ID NO: 25) | hGalNacT.fus.rev.231107 | Amplification of hGalNAcT N-terminal fragment, includes sequence for fusion PCR to endoT fragment |
| GAACAAGGACGTACCCGTT AAAGAACTGCA (SEQ ID NO: 26) | endoT.fusion.fw.251007 | Amplification of endoT fragment, includes sequence for fusion PCR to hST6GalI N-terminal fragment |
| CGCGAGCACCGTACCCGTTA AAGAACTGCA (SEQ ID NO: 27) | endoT.fushGalNacT.fw.231107 | Amplification of endoT fragment, includes sequence for fusion PCR to hGalNAcT N-terminal fragment |
| GCACCTGAGGTTAAGCGTTA ACCATAGCGTAG (SEQ ID NO: 28) | endoT.Bsu36I.rev.231007 | Amplification of endoT fragment, includes stop codon and Bsu36I site |
| GCACCTGAGGTTACAGATCT TCTTCAGAAATAAGCTTTTG TTCAGCGTTAACCATAGCGT AGTAGTTGATGG (SEQ ID NO: 29) | endoT.rev.myc.Bsu36I | Amplification of endoT fragment, includes sequence for MYC-tag, stop codon and Bsu36I site |
| ACGTGCTGGTTATTGTGCTG (SEQ ID NO: 30) | pCAGGSF | Forward sequencing primer for endoT construct in pCAGGS vector |
| GCCAGAAGTCAGATGCTCA AGG (SEQ ID NO: 31) | pCAGGSRMARCO | Reverse sequencing primer for endoT construct in pCAGGS vector |
| ATTTAGGTGACACTATAG (SEQ ID NO: 32) | SP6 | Forward sequencing primer for inserts in the pCR-bluntII-topo plasmid |
| AATACGACTCACTATAGGG (SEQ ID NO: 33) | T7 | Reverse sequencing primer for inserts in the pCR-bluntII-topo plasmid |

SEQ ID NO: 14
XhoI site-Start codon-fusion protein-Stop codon-Bsu36I site
ctcgagatgattcacaccaacctgaagaaaaagttcagctgctgcgtcctggtctttcttctgtttgcagtcatctgtgtgtggaaggaaaagaagaaagg gagttactatgattcctttaaattgcaaaccaaggaattccaggtgttaaagagtctggggaaattggccatgggtctgattcccagtctgtatcctcaa gcagcacccaggaccccacaggggccgccagaccctcggcagtctcagaggcctagccaaggccaaaccagaggcctccttccaggtgtggaacaaggac gtacccgttaaagaactgcagttgagagctgaaccaactgatttgcctaggcttatcgtttacttccagactactcacgactcttccaacagaccaatctc catgttgccattgatcactgagaagggtatcgctttgactcacttgatcgtttgttccttccacattaaccagggtggtgttgttcacttgaacgacttcc caccagatgatccacacttctacactttgtggaacgagactatcactatgaagcaggctggtgttaaggttatgggaatggttggtggtgctgctcctggt tctttcaacactcagactttggactctccagactctgctactttcgagcactactacggtcaattgagagatgctatcgttaacttccagttggagggaat ggatttggacgttgagcaaccaatgtcccaacaaggtatcgacagattgatcgctagattgagagctgatttcggtccagacttcttgattactttggctc cagttgcttctgctttggaggactcctctaacttgtctggtttctcctacactgctttgcaacagactcagggtaacgacattgactggtacaacactcag ttctactctggtttcggttctatggctgacacttccgactacgacagaatcgttgctaacgtttcgctccagctaaagttgttgctggtcagttgactac tcctgaaggtgctggatggattccaacttcctccttgaacaacactatcgtttccttggtttccgagtacggtcaaatcggtggtgttatgggatgggagt -continued acttcaattccttgccaggtggtactgctgaaccatgggagtgggctcaaatcgttactgagatcttgagaccaggattggttccagagctcaagattact gaggatgacgctgctagattgactggtgcttacgaagaatccgttaaggctgctgctgctgataacaagtccttcgttaagaggccttccatcaactacta cgctatggttaacgcttaacctcagg SEQ ID NO: 16
XhoI site-Start codon-fusion protein-MYC tag-Stop codon-Bsu36I site
<u>ctcgag</u>atgattcacaccaacctgaagaaaaagttcagctgctgcgtcctggtctttcttctgtttgcagtcatctgtgtgtggaaggaaaagaagaaagg gagttactatgattcctttaaattgcaaaccaaggaattccaggtgttaaagagtctggggaaattggccatggggtctgattcccagtctgtatcctcaa gcagcacccaggaccccacaggggccgccagaccctcggcagtctcagaggcctagccaaggccaaaccagaggcctccttccaggtgtggaacaaggac gtaccccgttaaagaactgcagttgagagctgaaccaactgatttgcctaggcttatcgtttacttccagactactcacgactcttccaacagaccaatctc catgttgccattgatcactgagaagggtatcgctttgactcacttgatcgtttgttccttccacattaaccagggtggtgttgttcacttgaacgacttcc caccagatgatccacacttctacactttgtggaacgagactatcactatgaagcaggctggtgttaaggttatgggaatggttggtggtgctgctcctggt tctttcaacactcagactttggactctccagactctgctactttcgagcactactacggtcaattgagagatgctatcgttaacttccagttggagggaat ggatttggacgttgagcaaccaatgtcccaacaaggtatcgacagattgatcgctagattgagagctgatttcggtccagacttcttgattactttggctc cagttgcttctgctttggaggactcctctaacttgtctggtttctcctacactgctttgcaacagactcagggtaacgacattgactggtacaacactcag ttctactctggtttcggttctatggctgacacttccgactacgacagaatcgttgctaacggtttcgctccagctaaagttgttgctggtcagttgactac tcctgaaggtgctggatggattccaacttcctccttgaacaacactatcgtttccttggtttccgagtacggtcaaatcggtggtgttatgggatgggagt acttcaattccttgccaggtggtactgctgaaccatgggagtgggctcaaatcgttactgagatcttgagaccaggattggttccagagctcaagattact gaggatgacgctgctagattgactggtgcttacgaagaatccgttaaggctgctgctgctgataacaagtccttcgttaagaggccttccatcaactacta cgctatggttaacgct*gaacaaaagcttatttctgaagaagatctg*taacctcagg SEQ ID NO: 18
XhoI site-Start codon-fusion protein-Stop codon-Bsu36I site
<u>Ctcgag</u>atgtggctgggccgccgggccctgtgcgctctggtcctttctgctcgcctgcgcctcgctggggctcctgtacgcgagcaccgtacccgttaaaga actgcagttgagagctgaaccaactgatttgcctaggatatcgtttacttccagactactcacgactcttccaacagaccaatctccatgttgccattgat cactgagaagggtatcgctttgactcacttgatcgtttgttccttccacattaaccagggtggtgttgttcacttgaacgacttccaccagatgatccac acttctacactttgtggaacgagactatcactatgaagcaggctggtgttaaggttatgggaatggttggtggtgctgctcctggttctttcaacactcag actttggactctccagactctgctactttcgagcactacacggtcaattgagagatgctatcgttaacttccagttggagggaatggatttggacgttga gcaaccaatgtcccaacaaggtatcgacagattgatcgctagattgagagctgatttcggtccagacttcttgattactttggctccagttgcttctgatt ggaggactcctctaacttgtctggtttctcctacactgctttgcaacagactcagggtaacgacattgactggtacaacactcagttctactctggtttcg gttctatggctgacacttccgactacgacagaatcgttgctaacggtttcgctccagctaaagttgttgctggtcagttgactactcctgaaggtgctgga tggattccaacttcctccttgaacaacactatcgtttccttggtttccgagtacggtcaaatcggtggtgttatgggatgggagtacttcaattccttgcc aggtggtactgctgaaccatgggagtgggctcaaatcgttactgagatcttgagaccaggattggttccagagctcaagattactgaggatgacgctgcta gattgactggtgcttacgaagaatccgttaaggctgctgctgctgataacaagtccttcgttaagaggccttccatcaactactacgctatggttaacgct taa<u>cctcagg</u>

SEQ ID NO: 10
XhoI site-Start codon-fusion protein-MYC tag-Stop codon-Bsu36I site
<u>ctcgag</u>atgtggctgggccgccgggccctgtgcgctctggtcctttctgctcgcctgcgcctcgctggggctcctgtacgcgagcaccgtacccgttaaaga actgcagttgagagctgaaccaactgatttgcctaggatatcgtttacttccagactactcacgactcttccaacagaccaatctccatgttgccattgat cactgagaagggtatcgctttgactcacttgatcgtttgttccttccacattaaccagggtggtgttgttcacttgaacgacttccaccagatgatccac acttctacactttgtggaacgagactatcactatgaagcaggctggtgttaaggttatgggaatggttggtggtgctgctcctggttctttcaacactcag actttggactctccagactctgctactttcgagcactactacggtcaattgagagatgctatcgttaacttccagttggagggaatggatttggacgttga gcaaccaatgtcccaacaaggtatcgacagattgatcgctagattgagagctgatttcggtccagacttcttgattactttggctccagttgcttctgctt tggaggactcctctaacttgtctggtttctcctacactgctttgcaacagactcagggtaacgacattgactggtacaacactcagttctactctggtttc ggttctatggctgacacttccgactacgacagaatcgttgctaacggtttcgctccagctaaagttgttgctggtcagttgactactcctgaaggtgctgg -continued atggattccaacttcctccttgaacaacactatcgtttccttggtttccgagtacggtcaaatcggtggtgttatgggatgggagtacttcaattccttgc caggtggtactgctgaaccatgggagtgggctcaaatcgttactgagatcttgagaccaggattggttccagagctcaagattactgaggatgacgctgct agattgactggtgcttacgaagaatccgttaaggctgctgctgctgataacaagtccttcgttaaggaggccttccatcaactactacgctatggttaacgc tgaacaaaagcttatttctgaagaagatctgtaacctcagg

---

What is claimed is:

1. An eukaryotic cell comprising:
   an exogenous endoglucosaminidase enzyme which endohydrolyzes a N,N'-diacetylchitobiosyl unit in an N-glycan linked to an exogenous glycoprotein; and
   the exogenous glycoprotein;
   wherein the endoglucosaminidase enzyme is retained in or passes through a secretory pathway and deglycosylates the exogenous glycoprotein;
   wherein the exogenous glycoprotein comprises, attached to an Asn glycosylation site, an N-glycan containing a single N-acetylglucosamine residue of a N,N'-diacetylchitobiosyl unit;
   wherein the N-glycan does not comprise a N,N'-diacetylchitobiosyl unit; and
   wherein the exogenous glycoprotein is produced by the cell with a uniform glycoprofile.

2. The eukaryotic cell of claim 1, which does not express an endogenous endoglucosaminidase enzyme.

3. The eukaryotic cell of claim 1, which is selected from the group consisting of a yeast cell, a plant cell, a mammalian cell, an insect cell, an Hek293 cell, and a *Pichia* cell.

4. The eukaryotic cell of claim 1, further comprising:
   at least one enzyme needed for complex glycosylation, said enzyme selected from the group consisting of mannosidases and glycosyltransferases, other than mannosyltransferases and phosphomannosyltransferases; and
   wherein the cell is a glyco-engineered yeast cell.

5. The eukaryotic cell of claim 4,
   wherein the at least one enzyme needed for complex glycosylation is selected from the group consisting of N acetylglucosaminyl transferase I, N acetylglucosaminyl transferase II, mannosidase II, galactosyltransferase, and sialyltransferase.

6. The eukaryotic cell of claim 4, which is deficient in the functional expression of at least one enzyme involved in the production of high mannose structures.

7. The eukaryotic cell of claim 1, wherein the endoglucosaminidase is a mannosyl glycoprotein endo beta N acetylglucosaminidase (E.C. 3.2.1.96).

8. The eukaryotic cell of claim 1, wherein the glycoprotein is secreted by the cell.

9. The eukaryotic cell of claim 1, wherein the endoglucosaminidase is operably linked to an endoplasmic reticulum or Golgi localization signal.

10. The eukaryotic cell of claim 9, wherein the endoplasmic reticulum or Golgi localization signal is from a protein selected from the group consisting of Kre2p, Ste13p, GM2 synthase, α2,6, glycosyltransferase, and α2,6, sialyltransferase.

11. The eukaryotic cell of claim 1,
    wherein the eukaryotic cell is an animal cell or a plant cell, and
    wherein the cell is deficient in an enzymatic activity needed for complex glycosylation, wherein the enzyme is selected from the group consisting of ER mannosidase I, glucosidase I, glucosidase II, N acetylglucosaminyl transferase I, N acetylglucosaminyl transferase II, mannosidase II, and wherein the cell is not capable of complex glycosylation of glycoproteins.

* * * * *